US009943590B2

(12) United States Patent
Harn, Jr. et al.

(10) Patent No.: US 9,943,590 B2
(45) Date of Patent: Apr. 17, 2018

(54) USE OF *LISTERIA* VACCINE VECTORS TO REVERSE VACCINE UNRESPONSIVENESS IN PARASITICALLY INFECTED INDIVIDUALS

(71) Applicants: The Trustees of the University of Pennsylvania, Philadelphia, PA (US); University of Georgia Research Foundation, Inc., Athens, GA (US)

(72) Inventors: Donald A. Harn, Jr., Athens, GA (US); Yvonne Paterson, Philadelphia, PA (US); Lisa McEwen, Athens, GA (US)

(73) Assignees: The Trustees of the University of Pennsylvania, Philadelphia, PA (US); University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 14/877,601

(22) Filed: Oct. 7, 2015

(65) Prior Publication Data
US 2016/0256538 A1 Sep. 8, 2016

Related U.S. Application Data

(62) Division of application No. 13/876,810, filed as application No. PCT/US2011/054613 on Oct. 3, 2011, now Pat. No. 9,226,958.

(60) Provisional application No. 61/388,822, filed on Oct. 1, 2010, provisional application No. 61/409,730, filed on Nov. 3, 2010.

(51) Int. Cl.
*A61K 39/21* (2006.01)
*A61K 39/00* (2006.01)
*A61K 39/12* (2006.01)

(52) U.S. Cl.
CPC .............. *A61K 39/21* (2013.01); *A61K 39/00* (2013.01); *A61K 39/0003* (2013.01); *A61K 39/12* (2013.01); *A61K 2039/523* (2013.01); *A61K 2039/54* (2013.01); *A61K 2039/577* (2013.01); *C12N 2710/20034* (2013.01); *C12N 2740/16034* (2013.01)

(58) Field of Classification Search
CPC ...................................................... A61K 39/21
See application file for complete search history.

(56) References Cited

U.S. PATENT DOCUMENTS

| | | | |
|---|---|---|---|
| 4,458,066 A | 7/1984 | Caruthers et al. |
| 4,521,382 A | 6/1985 | Kessick |
| 4,816,567 A | 3/1989 | Cabilly et al. |
| 5,204,253 A | 4/1993 | Sanford et al. |
| 5,262,177 A | 11/1993 | Brown et al. |
| 5,580,859 A | 12/1996 | Felgner et al. |
| 5,589,466 A | 12/1996 | Felgner et al. |
| 5,679,647 A | 10/1997 | Carson et al. |
| 5,681,570 A | 10/1997 | Yang et al. |
| 5,736,524 A | 4/1998 | Content et al. |
| 5,739,118 A | 4/1998 | Carrano et al. |
| 5,804,566 A | 9/1998 | Carson et al. |
| 5,824,538 A | 10/1998 | Branstrom et al. |
| 5,830,702 A | 11/1998 | Portnoy et al. |
| 5,858,682 A | 1/1999 | Gruenwald et al. |
| 5,922,583 A | 7/1999 | Morsey et al. |
| 5,922,687 A | 7/1999 | Mann et al. |
| 6,004,815 A | 12/1999 | Portnoy et al. |
| 6,015,567 A | 1/2000 | Hudziak et al. |
| 6,017,705 A | 1/2000 | Lurquin et al. |
| 6,051,237 A | 4/2000 | Paterson et al. |
| 6,099,848 A | 8/2000 | Frankel et al. |
| 6,287,556 B1 | 9/2001 | Portnoy et al. |
| 6,306,404 B1 | 10/2001 | LaPosta et al. |
| 6,329,511 B1 | 12/2001 | Vasquez et al. |
| 6,479,258 B1 | 11/2002 | Short |
| 6,504,020 B1 | 1/2003 | Frankel et al. |
| 6,521,449 B1 | 2/2003 | Polack et al. |
| 6,599,502 B2 | 7/2003 | Portnoy et al. |
| 6,635,749 B2 | 10/2003 | Frankel et al. |
| 6,740,516 B2 | 5/2004 | Savitzky et al. |
| 6,767,542 B2 | 7/2004 | Paterson et al. |
| 6,773,900 B2 | 8/2004 | Short et al. |
| 6,855,320 B2 | 2/2005 | Paterson et al. |
| 6,991,785 B2 | 1/2006 | Frey, II |
| 7,135,188 B2 | 11/2006 | Paterson et al. |
| 7,375,091 B2 | 5/2008 | Cheever et al. |
| 7,488,487 B2 | 2/2009 | Frankel et al. |
| 7,488,802 B2 | 2/2009 | Collins et al. |

(Continued)

FOREIGN PATENT DOCUMENTS

| | | |
|---|---|---|
| EP | 0902086 | 3/1999 |
| EP | 1408048 | 4/2004 |

(Continued)

OTHER PUBLICATIONS

Abachin et al., Formation of D-alanyl-lipoteichoic acid is required for adhesion and virulence of Listeria monocytogenes 2002, *Mol Microbiol* 43:1-14.

Adams et al., 1992, "Cre-lox recombination in *Escherichia coli* cells Mechanistic differences from the in vitro reaction", J. Mol. Biol. 226:661-673.

Ahmadzadeh et al. Tumor antigen-specific CD8 T cells infiltrating the tumor express high levels of PD-1 and are functionally impaired. Blood (2009) 114: 1537-1544.

(Continued)

*Primary Examiner* — Albert M Navarro
*Assistant Examiner* — Mark Navarro
(74) *Attorney, Agent, or Firm* — Mark S. Cohen; Pearl Cohen Zedek Latzer Baratz LLP

(57) ABSTRACT

This invention relates to methods of using a *Listeria* vaccine vector to induce a Th1 immune response in subjects having persistent Th2 immune response profiles.

24 Claims, 17 Drawing Sheets

(56) References Cited

U.S. PATENT DOCUMENTS

| | | | |
|---|---|---|---|
| 7,521,051 B2 | 4/2009 | Collins et al. |
| 7,588,930 B2 | 9/2009 | Paterson et al. |
| 7,635,479 B2 | 12/2009 | Paterson et al. |
| 7,655,238 B2 | 2/2010 | Paterson et al. |
| 7,662,396 B2 | 2/2010 | Paterson et al. |
| 7,691,393 B2 | 4/2010 | Dubensky et al. |
| 7,700,344 B2 | 4/2010 | Paterson et al. |
| 7,786,288 B2 | 8/2010 | Karp |
| 7,790,177 B2 | 9/2010 | Karp |
| 7,794,729 B2 | 9/2010 | Paterson et al. |
| 7,820,180 B2 | 10/2010 | Paterson et al. |
| 7,842,289 B2 | 11/2010 | Dubensky et al. |
| 7,855,064 B2 | 12/2010 | Paterson et al. |
| 7,858,097 B2 | 12/2010 | Paterson et al. |
| 7,871,604 B1 | 1/2011 | Curtiss, III et al. |
| 7,887,822 B2 | 2/2011 | Ferrone et al. |
| 7,935,804 B2 | 5/2011 | Dubensky et al. |
| 8,008,449 B2 | 8/2011 | Korman et al. |
| 8,114,414 B2 | 2/2012 | Paterson et al. |
| 8,168,757 B2 | 5/2012 | Finnefrock et al. |
| 8,287,883 B2 | 10/2012 | Dubensky et al. |
| 8,354,509 B2 | 1/2013 | Carven et al. |
| 8,383,796 B2 | 2/2013 | Korman et al. |
| 8,771,702 B2 | 7/2014 | Paterson et al. |
| 9,012,141 B2 | 4/2015 | Paterson et al. |
| 9,017,660 B2 | 4/2015 | Shahabi et al. |
| 9,226,958 B2 * | 1/2016 | Harn, Jr. et al. ... A61K 39/0003 |
| 2002/0025323 A1 | 2/2002 | Paterson et al. |
| 2002/0165172 A1 | 11/2002 | Sallberg et al. |
| 2003/0219802 A1 | 11/2003 | Dhaini et al. |
| 2003/0220239 A1 | 11/2003 | Simard et al. |
| 2004/0013685 A1 | 1/2004 | Andersen et al. |
| 2004/0013690 A1 | 1/2004 | Portnoy et al. |
| 2004/0058342 A1 | 3/2004 | Yousef et al. |
| 2004/0228877 A1 | 11/2004 | Dubensky et al. |
| 2005/0048081 A1 | 3/2005 | Frankel et al. |
| 2005/0281783 A1 | 12/2005 | Kinch et al. |
| 2006/0051380 A1 | 3/2006 | Schulick et al. |
| 2006/0073170 A1 | 4/2006 | Papierok |
| 2006/0093582 A1 | 5/2006 | Paterson et al. |
| 2006/0104991 A1 | 5/2006 | Paterson et al. |
| 2006/0121053 A1 | 6/2006 | Sweeney et al. |
| 2006/0205067 A1 | 9/2006 | Paterson et al. |
| 2006/0210540 A1 | 9/2006 | Paterson et al. |
| 2006/0233835 A1 | 10/2006 | Paterson et al. |
| 2007/0154953 A1 | 7/2007 | Brunner et al. |
| 2007/0207170 A1 | 9/2007 | Dubensky et al. |
| 2007/0207171 A1 | 9/2007 | Dubensky et al. |
| 2007/0253976 A1 | 11/2007 | Paterson et al. |
| 2007/0264279 A1 | 11/2007 | Paterson et al. |
| 2008/0124354 A1 | 5/2008 | Paterson et al. |
| 2008/0131456 A1 | 6/2008 | Paterson et al. |
| 2008/0213295 A1 | 9/2008 | Cheever et al. |
| 2008/0241069 A1 | 10/2008 | Paterson |
| 2009/0202587 A1 | 8/2009 | Paterson et al. |
| 2010/0069344 A1 | 3/2010 | Wang et al. |
| 2010/0233212 A1 | 9/2010 | Dubensky |
| 2011/0129499 A1 | 6/2011 | Maciag et al. |
| 2011/0142791 A1 | 6/2011 | Shahabi et al. |
| 2011/0223187 A1 | 9/2011 | Shahabi et al. |
| 2011/0271358 A1 | 11/2011 | Freeman et al. |
| 2012/0014984 A1 | 1/2012 | Shahabi |
| 2012/0135033 A1 | 5/2012 | Wallecha |
| 2014/0186387 A1 | 7/2014 | Lauer et al. |
| 2014/0234370 A1 | 8/2014 | Shahabi |
| 2015/0196628 A1 | 7/2015 | Mason et al. |
| 2015/0297702 A1 | 10/2015 | Shahabi et al. |
| 2015/0366955 A9 | 12/2015 | Shahabi et al. |

FOREIGN PATENT DOCUMENTS

| | | |
|---|---|---|
| WO | WO 90/12594 | 11/1990 |
| WO | WO 92/20356 | 11/1992 |
| WO | WO 93/15212 | 8/1993 |
| WO | WO 94/17192 | 8/1994 |
| WO | WO 96/14087 A1 | 5/1996 |
| WO | WO 96/34631 | 11/1996 |
| WO | WO 96/39154 | 12/1996 |
| WO | WO 97/03211 | 1/1997 |
| WO | WO 98/04720 | 2/1998 |
| WO | WO 98/48026 | 10/1998 |
| WO | WO 99/07861 | 2/1999 |
| WO | WO 99/25376 | 5/1999 |
| WO | WO 01/72329 | 10/2001 |
| WO | WO 01/79274 | 10/2001 |
| WO | WO 03/045318 A2 | 6/2003 |
| WO | WO 03/092600 | 11/2003 |
| WO | WO 03/102168 | 12/2003 |
| WO | WO 2004/004771 | 1/2004 |
| WO | WO 2004/006837 | 1/2004 |
| WO | WO 2004/056875 | 7/2004 |
| WO | WO 2004/072286 | 8/2004 |
| WO | WO 2004/110481 A2 | 12/2004 |
| WO | WO 2005/037233 | 4/2005 |
| WO | WO 2005/061534 | 7/2005 |
| WO | WO 2005/071088 | 8/2005 |
| WO | WO 2006/017856 | 2/2006 |
| WO | WO 2006/036550 | 4/2006 |
| WO | WO 2007/061848 | 5/2007 |
| WO | WO 2007/103225 | 9/2007 |
| WO | WO 2007/137258 A2 | 11/2007 |
| WO | WO 2008/019131 A2 | 2/2008 |
| WO | WO 2008/045148 A2 | 4/2008 |
| WO | WO 2008/109155 | 9/2008 |
| WO | WO 2008/130551 | 10/2008 |
| WO | WO 2009/110950 | 9/2009 |
| WO | WO 2009/143085 | 11/2009 |
| WO | WO 2009/0143085 | 11/2009 |
| WO | WO 2009/143167 | 11/2009 |
| WO | WO 2010/011870 | 1/2010 |
| WO | WO 2010/027827 | 3/2010 |
| WO | WO 2010/077634 | 7/2010 |
| WO | WO 2011/060260 A2 | 5/2011 |
| WO | WO 2011/066342 | 6/2011 |
| WO | WO 2011/100754 A1 | 8/2011 |
| WO | WO 2012/125551 | 9/2012 |
| WO | WO 2013/019906 | 2/2013 |
| WO | WO 2014/100079 | 6/2014 |

OTHER PUBLICATIONS

Ahmed, Nabil et al., "Immunotherapy for Osteosarcoma: Genetic Modification of T cells Overcomes Low Levels of Tumor Antigen Expression", Molecular Therapy, vol. 17, No. 10, Jun. 16, 2009 (Jun. 16, 2009), pp. 1779-1787.

Alexander et al, Characterization of an Aromatic Amino Acid-Dependent Listeria monocytogenes Mutant: Attenuation, Persistence, and Ability to Induce Protective Immunity in Mice 1993, Infection and Immunity 10 61 :2245-2248.

Al-Lazikani et al. JMB Standard Conformations for the Canonical Structures of Immunoglobulins., J. Mol. Biol. 273:927-948 (1997).

Allision et al., 1997, "Cloning and characterization of a Prevotella melaninogenica hemolysin", Infect. Immun. 65(7):2765-71.

Altschul et al., Basic Local Alignment Search Tool Basic Local Alignment Search Tool; J. Mol. Biol. 215:403-410 (1990).

Altschul, S.F. Amino Acid Substitution Matrices from an Information Theoretic Perspective; J. Mol. Biol. 219:555-565 (1991).

Altschul et al. A Protein Alignment Scoring System Sensitive at all Evolutionary Distances; J. Mol. Evol. 36:290-300 (1993).

Altschul et al., "Gapped BLAST and PSI-BLAST: a new generation of protein database search programs" (1997) Nucleic Acids Res. 25:3389-3402.

Amersham Introduction to Glutathione S-transferase (GST) Gene Fusion System , Pharmacia Biotech; BioDirectory, Piscataway, N.J., ( pp. 384-391) (2001).

An et al., 1996, "A recombinant minigene vaccine containing a nonameric cytotoxic-T Lymphocyte epitope confers limited protection against Listeria monocytogenes infection", Infect. Immun., vol. 64, No. 5, p. 1685-1693.

Anderson, 1998, "Human gene therapy ", Nature, Apr. 30; 392 (6679 Suppl):25-30.

(56) References Cited

OTHER PUBLICATIONS

Angelakopoulos et al., "Safety and shedding of an attenuated strain of listeria monocytogenes with a delection of actA/plcB in adult volunteers: a dose escalation study of oral innoculation", Infection and Immunity 2002, 70(7): 3592-3601.

Anthony "Precursor Lesions for Liver Cancer in Humans" Cancer Res. (1976) 36:2579-2583.

Attwood et al., "The Babel of Bioinformatics", Science, vol. 290, No. 5491: 471-473, 2000.

Auchtung et al "Regulation of a Bacillus subtilis mobile genetic element by intercellular signaling and the global DNA damage response". Proc Natl Acad Sci USA. Aug 30, 2005;102 (35):12554-9.

Auerbuch et al. "Development of a Competitive Index Assay to Evaluate the Virulence of Listeria monocytogenes actA Mutants during Primary and Secondary Infection of Mice " (2001) Infect. Immunity 69:5953-5957.

Awwad, 1989, "Cyclophosphamide-induced immunologically mediated regression of a cyclophosphamide-resistant murine tumor: a consequence of eliminating precursor L3T4+ suppresor T-cells", Cancer Res., 49(7):1649-1654.

Baca et al. "Protein Chemistry and Structure: Antibody humanization using monovalent phage display", (1997) J. Biol. Chem. 272:10678-10684.

Baert et al. "Influence of Immunogenicity on the Long-Term Efficacy of Infliximab in Crohn's Disease " (2003) New Engl. J. Med. 348:601-608.

Baloglu et al. "Immune Responses of Mice to Vaccinia Virus Recombinants Expressing Either Listeria Monocytogenes Partial Listeriolysin or *Brucella abortus* Ribosomal L7/L12 Protein" Vet Microbiol.; 109(1-2) M, Aug. 10, 2005.

Barbas. Synthetic Human Antibodies ; Nature Medicine, 1:837-839 (1995).

Bargmann et al. "The neu oncogene encodes an epidermal growth factor receptor related protein" Nature 319, 226-230, Jan. 16, 1986.

Bear, 1986, "Tumor-specific suppressor T-cells which inhibit the in vitro generation of cytolytic T-cells from immune and early tumor-bearing host spleens", Cancer Res., Apr.; 46(4 Pt 1):1805-12.

Beattie et al. "Cloning and charcterization of T-cell-reactive protein antigens from Listeria monocytogenes", infect. Immune. Sep. 1990, 58(9):2792-803.

Beatty et al.IFN-gamma-dependent inhibition of tumor angiogenesis by tumor infiltrating CD4+ T cells requires tumor responsiveness to IFN-gamma.J Immunol. Feb. 15, 2001;166(4):2276-82.

Beaucage et al. "Deoxynucleoside Phosphoramidites—A New Class of Key Intermediates for Deoxypolynucleotide Synthesis" Tetra. Lett. 22:1859-1862, (1981).

Becker at al., The changes in the T helper 1 (Th1) and T helper 2 (Th2) cytokine balance 3,4during HIV-1 infection are indicative of an allergic response to viral proteins that may bereversed by Th2 cytokine inhibitors and immune response modifiers—a review and hypothesis; Viruses Genes 28:5-18 (2004).

Belt et al (1991) Efficient cDNA cloning by direct phenotypic correction of a mutant human cell line (HPRT2) using an Epstein-Barr virus-derived cDNA expression vector. Nucleic Acids Res. 19, 4861-4866.

Beniaminovitz et al. "Prevention of Rejection in Cardiac Transplantation by Blockade of the Interleukin-2 Receptor With a Monoclonal Antibody " (2000) New Engl. J. Med. 342:613-619.

Benvegnu et al. Space Occupying lesions of the liver detected by ultrasonography and their relation to hypatocellular Carcinoma in Cirrhosis; Liver 12:80-83 (1992).

Bernhard et al., 2002, "Vaccination against the HER-2/neu oncogenic protein", Endocrine-Related Cancer, 9:33-44.

Bielecki et al. "Bacillus subtilis expressing a haemolysin gene from Listeria monocytogenes can grow in mammalian cells", Nature 1990, 354:175-176.

Billaut-Mulot et al. Interleukin-18 modulates immune responses induced by HIV-1 Nef DNA prime/protein boost vaccine; Vaccine 19:95-102 (2000).

Billington et al., 1997, "The Arcanobacterium (Actinomyces) pyogenes hemolysin, pyolysin, is a novel member of the thiol-activated cytolysin family", J. Bacteriol. Oct.; 179(19):6100-6.

Bird et al. "An autologous dendritic cell canine mammary tumor hybrid-cell fusion vaccine", Cancer Immunol Immunother. Jan. 2011;60(1):87-97.

Bodmer et al., 1988, "Enhanced recognition of a modified peptide antigen by cytotoxic T cells specific for influenza nucleoprotein", Cell 52:253-258.

Boon et al., 2006, "Human T-cell responses against melanoma" Annu. Rev. Immunol. 24:175-208.

Bishop et al. Adoptive Transfer of Immunity to Listeria Monocytogenes the Influence of in Vitro Stimulationon Lymphocyte Subset Requirements; J. Immunol. 139: 2005-2009 (1987).

Bourquin et al., 2000, "Myelin oligodendrocyte glycoprotein-DNA vaccination induces antibody-mediated autoaggression in experimental autoimmune encephalomyelitis" Eur. J. Immunol. 30:3663-3671.

Bouwer et al. Acquired immunity to an intracellular pathogen: immunologic recognition of L. monocytogenes-infected cells, Immunol. Rev. Aug. 1997; 158:137-46.

Bouwer et al. Cytotoxic-T-lymphocyte responses to epitopes of listeriolysin O and p60 following infection with Listeria monocytogenes, Infect. Immune. Jul. 1996; 64(7):2515-22.

Boyer et al., "DNA prime Listeria boost induces a cellular immune response to SIV antigens in the Rhesus Macaque model that is capable of limited suppression of SIV239 viral replication", Virology. 333: 88-101, 2005.

Brantl et al, "Molecular analysis of the replication region of the conjugative *Streptococcus agalactiae* plasmid pIP501 in Bacillus subtilis. Comparison with plasmids pAM31 and pSM1 9035" Nucleic Acid Res 18: 4783-4790, 1990.

Brett et al. "Comparison of antigen presentation of influenza a nucleoprotein expressed in attenuated AroA—*Salmonella typhimurium* with that of live virus", J Immunol. Apr. 1, 1993;150(7):2869-84.

Brockstedt et al, "Listeria-based cancer vaccines that segregate immunogenicity from toxicity" 2004, PNAS, 101:13832-13837.

Bron et al, "Use of the air Gene as a Food-Grade Selection Marker in Lactic Acid Bacteria" 2002, Appl Environ Microbiol, 68: 5663-70.

Bron et al., 2004, "Identification of Lactobacillus plantarum genes that are induced in the gastrointestinal tract of mice", J. Bacteriol. Sep.; 186(17):5721-9.

Brown et al., 1988, "Site-specific integration in Saccharopolyspora erthraea and multisite integration in Streptomyces lividans of actinomycete plasmid pSE101", J. Bacteriology 170: 2287-2295.

Brown et al. "Chemical synthesis and cloning of a tyrosine tRNA gene" 1979, Meth. Enzymol. 68:109-151.

Bruder et al. "Efficient induction of cytotoxic CD8+ T cells against exogenous proteins: establishment and characterization of a T cell line specific for the membrane protein ActA of Listeria monocytogenes", Eur. J. Immunol. Sep. 1998; 28(9):2630-9.

Bruhn et al., 2005, "Characterization of anti-self CD8 T-cell responses stimulated by recombinant Listeria monocytogenes expressing the melanoma antigen TRP-2", Vaccine, Jul. 21; 23(33):4263-72.

Bruhn et al., 2007, "Listeria as a Vaccine Vector", Microbes and Infection, vol. 9, No. 10, pp. 1226-1235.

Brundage et al, 1993. Expression and phosphorylation of the Listeria monocytogenes ActA protein in mammalian cells, Proc. Natl. Acad. Sci., USA, 90:11890-11894.

Bubert et al., 1997, "The Listeria monocytogenes iap gene as an indicator gene for the study of PrfA-dependent regulation", Mol. Gen. Genet. Sep.; 256(1):54-62.

Calendar et al., Poster presented at the ISOPOL Meeting 2001, http://64.233.169.104/search?q=cache:mA_uJpQsCrcJ:www.ma.uni-heidelberg.de/inst/imh/download/isopol.doc+Portnoy+isopol+2001&hl=en&ct=clnk&cd=3&gl=us.

(56) References Cited

OTHER PUBLICATIONS

Camilli et al, 1991, Listeria monocytogenes mutants lacking phosphatidylinositol-specific phospholipase C area virulent, J. Exp. Med., 173:751-754.

Camilli et al., 1993, "Dual roles of plcA in Listeria monocytogenes pathogenesis", Mol. Microbiol. 8:143-157.

Camilli et al. "Insertional mutagenesis of Listeria monocytogenes with a novel Tn917 derivative that allows direct cloning of DNA flanking transposon insertions", J Bacteriol, Jul. 1990;172(7):3738-44.

Carbone, 1989, "Induction of ovalbumin-specific cytotoxic T cells by in vivo peptide immunization" J. Exp. Med. 169:603-612.

Carbone, 1990, "Class I-restricted processing and presentation of exogenous cell-associated antigen in vivo", J. Exp. Med. 171:377-387.

Carpenter et al. Non-Fc Receptor-Binding Humanized Anti-CD3 Antibodies Induce Apoptosis of Activated Human T Cells; J. Immunol. 165:6205-6213 (2000).

Catic et al. "Introduction of protein or DNA delivered via recombinant Salmonella typhimurium into the major histocompatibility complex class I presentation pathway of macrophages", Microbes Infect., Feb. 1999, 1(2):113-21.

Cenatiempo et al. "Prokaryotic gene expression in vitro: transcription-translation coupled systems" Biochimie 68:505-515 (1986).

Chen, B.J. et al., "PD-L1 Expression Is Characteristic of a Subset of Aggressive B-cell Lymphomas and Virus-Associated Malignancies" Clin Cancer Res 19: 3462-3473 (2013).

Chen et al. "Episomal Expression of Truncated Listeriolysin O in LmddA-LLO—E7 Vaccine Enhances Antitumor Efficacy by Preferentially Inducing Expansions of CD4FoxP3_andCD8 T Cells", Cancer Immunol Res; 2(9) Sep. 2014, pp. 911-922.

Chothia et al. Canonical Structures for the Hypervariable Regions of Immunoglobulins; J Mol. Biol. 196:901-917 (1987).

Chothia et al. Confirmations of immunoglobulin hypervariable Regions; Nature 342:878-883 (1989).

Ciesielski et al. "Therapeutic Effect of a T Helper Cell Supported CTL Response Induced by a Survivin Peptide Vaccine against Murine Cerebral Glioma"; Cancer Immunol Immunother; 57(12): 1827-1835 (2008).

Clackson et al. Making Antibody Fragments Using Phage Display Libraries; Nature 352: 624-628 (1991).

Clark et al., "Clinical use of streptolysin-O to facilitate antisense oligodeoxyribonucleotide delivery for purging autografts in chronic myeloid leukaemia", Bone Marrow Transplantation, vol. 23, No. 12, 1999, pp. 1303/1308.

Clifton Guy et al., "Overcoming cancer immune tolerance and escape", Clinical Cancer Research : An Official Journal of the American Association for Cancer Research 2009, vol. 15, No. 3, pp. 749-751.

Collins et al. "Directional cloning of DNA fragments at a large distance from an initial probe: a circularization method", Proc Natl Acad Sci U S A. Nov. 1984;81(21):6812-6.

Courvalin et al. 1995, "Gene transfer from bacteria to mammalian cells", C R Acad Sci III, Dec.; 318(12):1207-12.

Coynault et al. "Virulence and vaccine potential of Salmonella typhimurium mutants deficient in the expression of the RpoS (sigma S) regulon", Mol Microbiol. Oct. 1996;22(1):1 49-60.

Cunto-Amesty et al. 2003, "Strategies in cancer vaccines development", Int. J. Parasitol. 33(5-6):597-613.

Da'Dara et al., "Helminth infection suppresses T-cell immune response to HIV-DNA-based vaccine in mice", Vaccine 2006, vol. 24, No. 24, pp. 5211-5219.

Da'Dara et al. Elimination of helminth infection restores HIV-1C vaccine-specific T cellresponses independent of helminth-induced IL-10; Vaccine; 3;28(5)1310-7 (2010).

Dakappagari et al., 2000, "Prevention of mammary tumors with a chimeric HER-2 B-cell epitope peptide vaccine", Cancer Res. Jul. 15; 60(14):3782-9.

Darji et al. The role of the bacterial membrane protein ActA in immunity and protection against Listeria monocytogenes, J. Immunol. Sep. 1, 1998 161(5):2414-20.

Darji et al. "Antigen-specific T cell receptor antagonism by antigen-presenting cells treated with the hemolysin of Listeria monocytogenes: a novel type of immune escape", Eur. J. Immunol. Jul. 1997; 27(7):1696-703.

Darji et al. T-cell anergy induced by antigen presenting cells treated with the hemolysin of Listeria monocytogenes, Immunol. Lett. Jun. 1, 1997 57(1-3):33-7.

Darji et al., 1995, "Hyperexpression of listeriolysin in the nonpathogenic species Listeria innocua and high yield purification", J. Biotechnol. Dec. 15; 43(3):205-12.

Darji et al., 1995, "Listeriolysin generates a route for the presentation of exogenous antigens by major histocompatibility complex class I", Eur. J. Immunol. Oct.; 25(10):2967-71.

Darji et al., 1997, "Oral somatic transgene vaccination using attenuated S. typhimurium" Cell 91:765-775.

Darji et al., 1997, "TAP-dependent major histocompatibility complex class I presentation of soluble proteins using listeriolysin", Eur. J. Immunol. Jun.; 27(6):1353-9.

Darji et al., 2003, "Induction of immune responses by attenuated isogenic mutant strains of Listeria monocytoge" Vaccine 1; 21 Suppl. 2:S102-9.

De Boer et al, "A division inhibitor and a topological specificity factor coded for by the minicell locus determine proper placement of the division septum in E. coli" 1989, Cell 56:641-649.

De Bruin et al. Selection of high-affinity phage antibodies from phage display libraries; Nature Biotechnol. 17:397-399 (1999).

Decatur et al., "A PEST-Like Sequence in Listeriolysin O Essential for Listeria monocytogenes Pathogenicity", Science 2000, 290:992-995.

De Las Mulas et al. "Oncogene HER-2 in canine mammary gland carcinomas." Breast cancer research and treatment 80.3 (2003): 363-367.

Dell'Erba et al., "Immunohistochemical reactivity of anti-melanoma monoclonal antibody 225.28S in Human Breast Cancer Biopsies", Anticancer Res. 2001, vol. 21, No. 2A, pp. 925-930.

De Maria, Raffaella, et al. "Spontaneous feline mammary carcinoma is a model of HER2 overexpressing poor prognosis human breast cancer." Cancer research 65.3 D (2005): 907-912.

Dembo et al. Limit Distribution of Maximal Non-Aligned Two-Sequence Segmental Score Ann. Prob. 22:2022-2039; (1994).

Dermime et al. 2004, "Vaccine and antibody-directed T cell tumour immunotherapy" Biochim Biophys Acta. 1704(1):11-35.

Deshpande et al., 1997, "Isolation of a contact-dependent haemolysin from Mycobacterium tuberculosis", J. Med. Microbiol. Mar.; 46(3):233-8.

Dietrich et al., 1998, "Delivery of antigen-encoding plasmid DNA into the cytosol of macrophages by attenuated suicide Listeria monocytogenes" Nature Biotechnology 15:181-185.

Dietrich et al., 2001, "From evil to good: a cytolysin in vaccine development", Trends Microbiol. Jan.; 9(1):23-8.

Disis, "Generation of immunity to the HER-2/neu oncogenic protein in patients with breast and ovarian cancer using a peptide-based vaccine" Clin Cancer Res. 5(6):1289-97, Jun. 1999.

Doling et al. Cytotoxic T-lymphocyte epitopes fused to anthrax toxin induce protective antiviral immunity, Infect. Immun. Jul. 1999; 67(7):3290-6.

Dominiecki et al. Tumor sensitivity to IFN-γ is required for successful antigen-specific immunotherapy of a transplantable mouse tumor model for HPV-transformed tumors; Cancer Immunol Immunother ;54(5):477-88 (2005).

Dons et al. "Cloning and characterization of a gene encoding flagellin of Listeria monocytogenes", Mol Microbiol. Oct. 1992;6(20):2919-29.

Dramsi et al., 1995, "Entry of Listeria monocytogenes into hepatocytes requires expression of inIB, a surface protein of the internalin multigene family", Mol. Microbiol. 16(2):251-61.

Dunn et al., 1991, "Selective radiation resistance of immunologically induced T cells as the basis for irradiation-induced T-cell-mediated regression of immunogenic tumor", J. Leukoc Biol. 49(4):388-396.

(56) References Cited

OTHER PUBLICATIONS

Dustoor, "Antitumor activity of listeria monocytogenes on a guinea pig fibrosarcoma", Infection and Immunity, 1979, vol. 23, No. 1, pp. 54-60.
Dzojic H et al "Adenovirus-mediated CD40 ligand therapy induces tumor cell apoptosis and systemic immunity in the TRAMP-C2 mouse prostate cancer model" The Prostate 66: 831-838 (2006).
Ebbeson et al. "Rhabdomyolysis, acute renal failure, and compartment syndrome in a child with parainfluenza type 1 infection", The Pediatric Infectious Disease Journal vol. 28, No. 9, Sep. 2009.
Ebert et al., 1990, "Selective immunosuppressive action of a factor produced by colon cancer cells", Cancer Res. 50(19):6158-6161.
Edman et al. A Protein Sequenator; Eur. J. Biochem . 80: 116-132, (1967).
Eisenhauer et al. New response evaluation criteria in solid tumours: Revised RECIST guideline (version 1.1), Eur. J Cancer 45:228-247 (2009).
Emond et al. "A ribosomal DNA fragment of Listeria monocytogenes and its use as a genus-specific probe in an aqueous-phase hybridization assay", Appl Environ Microbiol. Aug. 1993;59(8):2690-7.
Ercolini et al., "Identification and characterization of the immunodominant rat HER-2/neu MHC class I epitope presented by spontaneous mammary tumors from Her-2/neu transgenic mice", Journal of Immunology, 2003, vol. 170, No. 8, pp. 4273-4280.
European Search Report Application No. 12758350 dated Aug. 14, 2014.
European Search report Application No. 09751395.6 dated Jul. 11, 2012.
European Search report Application No. 10830785.1 dated Dec. 10, 2013.
Everts et al. Selective Intracellular Delivery of Dexamethasone into Activated Endothelial Cells Using an E-Selectin-Directed Immunoconjugate; J. Immunol. 168:883-889 (2002).
Ezzel, 1995, "Cancer Vaccines: An Idea Whose Time Has Come?" J. NIH Res., 7:46-49.
Falk et al., 1991, "Identification of naturally processed viral nonapeptides allows their quantification in infected cells and suggests an allele-specific T cell epitope forecast" J. Exp. Med. 174(2):425-434.
Ferrari et al. "Isolation of an Alanine Racemase Gene from Bacillus subtilis and its Use for Plasmid Maintenance in B. subtilis", Nature Biotechnology 3, 1003-1007 (1985).
Finn et al., 2003, "Cancer vaccines: between the idea and the reality" Nature Reviews Immunology 3:630-641.
Flint et al., "Overexpression of the erbB-2 proto-oncogene in canine osteosarcoma cell lines and tumors", Vet. Pathol. 41: 291-296, 2004.
Foote et al. Antibody Framework Residues Affecting the Conformation of the Hypervariable Loops; J. Mol. Biol. 224:487-499 (1992).
Fouts et al. "Construction and immunogenicity of *Salmonella typhimurium* vaccine vectors that express HIV-1 gp120", Vaccine. Dec. 1995;13(17):1697-705.
Frankel et al. "Induction of cell-mediated immune responses to human immunodeficiency virus type 1 Gag protein by using Listeria monocytogenes as a live vaccine vector", J Immunol. Nov. 15, 1995;155(10):4775-82.
Frankel et al., "Induction of a cell-mediated immune response to HIV gag using Listeria monocytogenes as a live vaccine vector", J. Immunol. 155: 4766-4774. 1995.
Frey, 1993, "Rat adenocarcinoma 13762 expresses tumor rejection antigens but tumor-bearing animals exhibit tumor-specific immunosuppression", Clin. Immunol. Immunopath. 69(2):223-233.
Friedman et al., 2000, "Induction of human immunodeficiency virus (HIV)-specific CD8 T-cell responses by Listeria monocytogenes and a hyperattenuated Listeria strain engineered to express HIV antigens" J. Virology 74 9987-9993.
Fu et al., 1990, "Expansion of Immunoregulatory macrophages by granulocyte-macrophage colony-stimulating factor derived from a murine mammary tumor", Cancer Res. 50(2):227-234.
Fuji, 1987, "Significance of suppressor macrophages for immunosurveillance of tumor-bearing mice" J. Natl. Cancer Inst. 78(3):509-517.
Furukawa, 1993, "Nude mouse metastatic models of human stomach cancer constructed using orthotopic implantation of histologically intact tissue" Cancer Res. 53(5):1204-1208.
Gadiot et al., "Overall survival and PD-L1 expression in metastasized malignant melanoma" Cancer 117:2192-2201 (2011).
Galakatos et al. "Biosynthetic alr alanine racemase from *Salmonella typhimurium*: DNA and protein sequence determination", Biochemistry. Jun. 3, 1986;25(11):3255-60.
Galen et al., 2001, "Can a 'flawless' live vector vaccine strain be engineered?", Trends Microbiol. 9(8):372-6.
Gao et al. Overexpression of PD-L1 significantly associates with tumor aggressiveness and postoperative recurrence in human hepatocellular carcinoma. Clinical Cancer Research (2009) 15: 971-979.
Garay-Malpartida et al. Bioinformatics. Jun. 2005.;21 Suppl 1 :i169-76.
Gentschev et al. "*Salmonella* Strain Secreting Active Listeriolysin Changes Its Intracellular Localization", Infect. Immun., 1995, 63:4202-4205.
Gentschev et al. 1996, "Development of antigen-delivery systems, based on the *Escherichia coli* hemolysin secreatiohn pathway" Gene 179:133-140.
Ghebeh et al. The B7-H1 (PD-L1) T lymphocyte-inhibitory molecule is expressed in breast cancer patients with infiltrating ductal carcinoma: correlation with important high-risk propgnostic factors. Neoplasia (2006) 8: 190-198.
Ghebeh H. Foxp3+ tregs and B7-H1+/PD-1+ T lymphocytes co-infiltrate the tumor tissues of high-risk breast cancer patients: implication for immunotherapy. BMC Cancer. Feb. 23, 2008;8:57.
Ghosh et al. "Natalizumab for Active Crohn's Disease " (2003) New Engl. J. Med. 348:24-32.
Giannini et al. Morphological Precursors of Hepatocellular Carcinoma: A Morphometrical Analysis; Hepatogastroenterol. 34:95-97 (1987).
Gibellini et al. Extracellular HIV-1 Tat Protein Induces the Rapid Ser 133 Phosphorylation and Activation of CREB Transcription Factor in Both Jurkat Lymphoblastoid T Cells and Primary Peripheral Blood Mononuclear Cells; J. Immunol. 160:3891-3898 (1998).
Gilbert et al. Enhanced CD8 T cell immunogenicity and protective efficacyin a mouse malaria model using a recombinant adenoviral vaccine in heterologous prime—boost immunization regimes; Vaccine 20:1039-45 (2002).
Gilman et al. "Isolation of sigma-28-specific promoters from Bacillus subtilis DNA" 1984, Gene 32:11-20.
Gilmore et al., 1989, "A Bacillus cereus cytolytic determinant, cereolysin AB, which comprises the phospholipase C and sphingomyelinase genes: nucleotide sequenc and genetic linkage", J. Bacteriol. Feb.; 171(2):744-53.
Gish et al. Identification of protein coding regions by database similarity search; Nature Genet. 3:266-272 (1993).
Glick (1987). Factors affecting the expression of foreign proteins in *Escherichia coli*, J. Ind. Microbiol. 1:277-282.
Glomski et al., 2002, "The Listeria monocytogenes hemolysin has an acidic pH optimum to compartmentalize activity and pevent damage to infected host cells" J. Cell Biol. Mar. 18; 156(6):1029-38.
Goebel et al., 1993, "Listeria monocytogenes—a model system for studying the pathomechanisms of an intracellular microorganism", Zbl. Bakt. 278:334-347.
Gold et al., "Translational initiation in prokaryotes." 1981, Ann. Rev. Microbiol. 35:365-404.
Gonzalo, R. M. et al. A heterologous prime—boost regime using DNA and recombinant vaccinia virus expressing the Leishmania infantum P36/LACK antigen protects BALB/c mice from cutaneous leishmaniasis; Vaccine 20:1226-31 (2002).
Goossens et al., 1992, "Induction of protective CD8+ T lymphocytes by an attenuated Listeria monocytogenes actA mutant" Int. Immunol. Dec.; 4(12):1413-8.

(56) References Cited

OTHER PUBLICATIONS

Goossens et al., 1995, "Attenuated Listeria monocytogenes as a live vector for induction of CD8+ T cells in vivo: a study with the nucleoprotein of the lymphocytic choriomeningitis virus", Int. Immunol. May; 7(5):797-805.
Gottesman, (1984). Bacterial regulation: global regulatory networks Annu Rev Genet, Ann. Rev. Genet. 18:415-442.
Gouin et al. "The Listeria monocytogenes InlC protein interferes with innate immune responses by targeting the I B kinase subunit IKK ", Proceedings of the National Academy of Sciences, vol. 107, No. 40, Sep. 20, 2010 (Sep. 20, 2010), pp. 17333-17338.
Graham et al. "Candidate AIDS vaccines", N Engl J Med. Nov. 16, 1995;333(20):1331-9.
Gregory et al., 1997, "Internalin B promotes the replication of Listeria monocytogenes in mouse hepatocytes" Infect. Immun. 65(12):5137-41.
Gunn et al., 2002, "Recombinant Intra-cellular Bacteria as Carriers for Tumor Antigens", In Vaccine Delivery Strategies, Chapter 14, Eds. Guido Dietrich and Werner Goebel, Horizon Scientific Press, UK.
Gunn et al., "Two Listeria monocytogenes vaccine vectors that express different molecular forms of human papilloma virus-16 E7 induce qualitatively different T cell immunity that correlated with their avility to induce regression of established tumors immortalized by HPV-16", Journal of Immunology, vol. 167, No. 11, 2001, pp. 6471-6479.
Guzman et al. "Attenuated Listeria monocytogenes carrier strains can deliver an HIV-1 gp120 T helper epitope to MHC class II-restricted human CD4+ T cells", European Journal of Immunology, vol. 28, No. 6, Jun. 1998, pp. 1807-1814.
Hamanishi J et al. Programmed cell death 1 ligand 1 and tumor-infiltrating CD8+ T lymphocytes are prognostic factors of human ovarian cancer. Proceeding of the National Academy of Sciences (2007): 104: 3360-3365.
Hancock, J.M. et al. SIMPLE34: An Improved and Enhanced Implementation for VAX and Sun computers of the Simple algorithm for analysis of clustered repetitive motifs in nucleotide sequences; Comput. Appl. Biosci. 10:67-70 (1994).
Harty et al. "CD8 T lymphocytes specific for the secreted p60 antigen protect against Listeria monocytogenes infection", J. Immunol. May 1, 1995; 154(9):4642-50.
Harty et al. "CD8+ T cells specific for a single nonamer epitope of Listeria monocytogenes are protective in vivo", J Exp Med. Jun. 1, 1992;175(6):1531-8.
Hassan et al., 2004, "Mesothelin: a new target for immunotherapy" Clin. Cancer Res. 10(12 Pt 1):3937-42.
Hauf et al., 1997, "Listeria monocytogenes infection of P388D1 macrophages results in a biphasic NF-kappaB (RelA/p50) activation induced by lipoteichoic acid and Bacterial phospholipases and mediated by IkappaBalpha and IkappaBbeta degradation", Proc. Natl. Acad. Sci. U.S.A. Aug. 19; 94(17):9394-9.
Haynes et al. "Update on the issues of HIV vaccine development", Ann Med. Feb. 1996;28(1):39-41.
Haynes et al. "Scientific and social issues of human immunodeficiency virus vaccine development", Science. May 28, 1993;260(5112):1279-86.
He et al. Humanization and Pharmacokinetics of a Monoclonal Antibody with Specificity for Both E- and P-Selectin; J. Immunol. 160:1029 (1998).
Heinrich Je et al (Vaccination against prostate cancer using a live tissue factor deficient cell line in Lobund-Wistar rats. Cancer Immunol Immunother 2007;56(5):725-30).
Henikoff et al., "Amino acid substitution matrices from protein blocks " (1992) Proc. Natl. Acad. Sci. USA 89:10915-10919.
Herold et al. "Anti-Cd3 Monoclonal Antibody in New-Onset Type 1 Diabetes Mellitus" (2002) New Engl. J. Med. 346:1692-1698.
Hess et al., 1995, "Listeria monocytogenes p60 supports host cell invasion by and in vivo survival of attenuated *Salmonella typhimurium*" Infect. Immun. May; 63(5):2047-53.

Hess et al., 1996, "*Salmonella typhimurium* aroA-infection in gene-targeted immunodeficient mice: major role of CD4+ TCR-alpha beta cells and IFN-gamma in bacterial clearance independent of intracellular location" J. Immunol. May 1; 156(9):3321-6.
Hess et al., 1996, "Superior efficacy of secreted over somatic antigen display in recombinant *Salmonella* vaccine induced protection against listeriosis" Proc. Nat. Acad. Sci. 93:1458-1463.
Hess et al., 1997, "Protection against murine listeriosis by an attenuated recombinant *Salmonella typhimurium* vaccine strain that secretes the naturally somatic antigen superoxide dismutase", Infect. Immun. Apr.; 65(4):1286-92.
Hess et al, "*Mycobacterium bovis* Bacille Calmette-Guerin strains secreting listeriolysin of Listeria monocytogenes", Proc. Natl. Acad. Sci. U.S.A. Apr. 28, 1998; 95(9):5299-304.
Hess et al. Abstract, "Live antigen carriers as tools for improved anti-tuberculosis vaccines", FEMS Immunol. Med. Microbiol. Feb. 1999; 23(2):165-73.
Higgins et al., Abstract, "Delivery of protein to the cytosol of macrophages using *Escherichia coli* K-12", Mol. Microbiol. Mar. 31, 1999(6):1631-41.
Higgins et al., 1998, "Bacterial delivery of DNA evolves" Nat. Biotechnol. Feb.; 16(2):138-9.
Hiltbold et al. "The presentation of class I and class II epitopes of listeriolysin O is regulated by intracellular localization and by intracelluar spread of Listeria monocytogenes", J. Immunol. Aug. 1, 1996; 157(3):1163-75.
Hiltbold et al. "Mechanisms of processing and presentation of the antigens of Listeria monocytogenes", Infect. Agents Dis. Oct. 1993; 2(5):314-23.
Hino et al. Tumor cell expression of programmed cell death-1 is a prognostic factor for malignant melanoma. Cancer (2010 116(7):1757-66.
Hjortland et al., "Immunotoxin treatment targeted to the higher-molecular weight melanoma-associated antigen prolonging the survival of immunodeficient rats with invasive intracranial human glioblastoma multiforme", J. Neurosurg. 2004, vol. 100, No. 2, pp. 320-327.
Hodgson, 2000, "Generalized transduction of serotype 1/2 and serotype 4b strains of Listeria monocytogenes", Mol. Microbiol. 35(2):312-23.
Hoogenboom et al. Natural and designer binding sites made by phage display technology; Immunol. Today 21:371-377 (2000).
Hsing et al. Requirement for Nuclear Factor-kB Activation by a Distinct Subset of CD40-Mediated Effector Functions in B Lymphocytes; J. Immunol. 162:2804-2811 (1999).
Huang et al., 1994, "Role of bone marrow-derived cells in presenting MHC class I-restricted tumor antigens" Science 264:961-965.
Hussain et al., 2004, "CD4+CD25+ regulatory T cells that secrete TGFbeta and IL-10 are preferentially induced by a vaccine vector" J. Immunother. Sep.-Oct.; 27(5):339-46.
Hussain et al., "What is needed for effective antitumor immunotherapy? Lessons learned using Listeria Monocytogenes as a live vector for HPV-associated tumors", Cancer Immunology, Immunotherapy, vol. 54, No. 6, 2005, pp. 577-586.
Ikonomidis et al., 1994, Abstract E-90, Abstracts, 94th General Meeting of the American society for Microbiology, May 23-27.
Ikonomidis et al. "Delivery of a viral antigen to the class I processing and presentation pathway by Listeria monocytogenes", J Exp Med. Dec. 1, 1994;180(6):2209-18.
Ikonomidis et al. "Influenza-specific immunity induced by recombinant Listeria monocytogenes vaccines"; Vaccine, 15:433-440. (1997).
Inman et al. PD-L1 (B7-H1) expression by urothelial carcinoma of the bladder and BCG-induced granulomata: associations with localized stage progression. Cancer (2007): 109: 1499-1505.
International Search report Application No. PCT/US 10/56534 dated Jun. 27, 2011.
International Search report Application No. PCT/US2012/051187 dated Jan. 23, 2013.
International Search report Application No. PCT/US2009/44538 dated Aug. 14, 2009.
International Search Report Application No. PCT/US2012/028757 dated Aug. 27, 2012.

(56) References Cited

OTHER PUBLICATIONS

Jensen et al., 1997, "Recombinant Listeria monocytogenes as a live vaccine vehicle and a probe for studying-cell-mediated immunity" Immunological Review 158:147-157.
Jensen, 1997, "Recombinant Listeria monocytogenes vaccination eliminates papillomavirus-induced tumors and prevents papilloma formation from viral DNA", J. Virol. 71(11):8467-8474.
Jiang et al. "Characterization of a mutant Listeria monocytogenes strain expressing green fluorescent protein" Acta. Biochim. Biophys Sin (Shanghai), 37(1): 19-24, (2005).
Johnson et al., "Kabat database and its applications: 30 years after the first variability plot", Nucleic Acids Research, 2000, vol. 28, No. 1, pp. 214-218.
Jones et al. "Characterization of Listeria monocytogenes pathogenesis in a strain expressing perfringolysin O in place of listeriolysin O." (1994) Infect. Immunity 65: 5608-5613.
Kabat, et al., "Unusual distributions of amino acids in complementarity-determining (hypervariable) segments of heavy and light chains of immunoglobulins and their possible roles in specificity of antibody-combining sites" (1977) J. Biol. Chem. 252:6609-6616.
Kabat The Structural Basis of Antibody Complementarity; Adv. Prot. Chem. 32:1-75 (1978).
Kaithamana et al. Induction of Experimental Autoimmune Graves' Disease in BALB/c Mice; J. Immunol. 163:5157-5164 (1999).
Karlin, S., et al., "Methods for assessing the statistical significance of molecular sequence features by using general scoring schemes " (1990) Proc. Natl. Acad. Sci. USA 87:2264-2268.
Karlin, S., et al., "Applications and statistics for multiple high-scoring segments in molecular sequences" (1993) Proc. Natl. Acad. Sci. USA 90:5873-5877.
Kaufman et al., "Impact of intracellular location of and antigen display by intracellular bacteria:implications for vaccine development", J. Immunol. Lett. 1999, 65(1-2):81-84.
Kaufmann "Immunity to intracellular bacteria", Annu Rev Immunol. 1993;11:129-63.
Kawashima et al. "Identification of HLA-A3-restricted cytotoxic T lymphocyte epitopes from carcinoembryonic antigen and HER-2/neu by primary in vitro immunization with peptide-pulsed dendritic cells" Cancer Res. Jan. 15, 1999;59(2):431-5.
Kim "Coexpression of BiP increased antithrombotic hirudin production in recombinant *Saccharomyces cerevisiae*", Journal of Biotechnology, vol. 101, No. 1, pp. 81-87, 2003.
King et. al., "Amplification of a novel v-erbB-related gene in a human mammory carcinoma" (1985). Science 229:974-976.
Knutson et al., "Immunization with a HER-2/neu helper peptide vaccine generates HER-2/neu CD8 T-cell immunity in cancer patients." The Journal of Clinical Investegation, 107:477-484, 2001.
Kocks et al., 1992, "L monocytogenes-induced act in assembly requires the actA gene product", Cell, vol. 68, No. 3, p. 521-531.
Kohler et al. Continuous Cultures of Fused Cells Secreting Antibody of Predefined Specificity; Nature 256: 495 (1975).
Kohler et al, "Expression of the iap gene coding for protein p60 of Listeria monocytogenes is controlled on the posttranscriptional level" J Bacteriol 173: 4668-74, 1991.
Kovacsovics-Bankowski et al., 1993, "Efficient major histocompatibility complex class I peresentation of exogenous antigen upon phagocytosis by macrophages", Proc. Natl. Acad. Sci. USA 90:4942-4946.
Kucera et al., "Prostate Specific Antigen (PSA) in Breat and Ovarian Cancer", Anticancer Res 1997, vol. 17, No. 60, pp. 4735-4737.
Kyte et al., "A simple method for displaying the hydropathic character of a protein", J. Mol. Biol. 157, 105 (1982).
Lampson et al., 1993, "Exploiting the lacZ reporter gene for quantitative analysis of disseminated tumor growth within the brain: use of the lacZ gene product as a tumor antigen, for evaluation of antigenic modulation, and to facilitate image analysis of tumor growth in situ", Cancer Research 53:176-182.
Landy, A., Mechanistic and structural complexity in the site-specific recombination pathways of Int and FLP Current Opinion in Genetics & Development 3:699-707; (1993).

Lasa et al., 1997, "Identification of two regions in the N-terminal domain of ActA involved in the actin comet tail formation by Listeria monocytogenes" EMBO 16(7):1531-40.
Lauer et al., "Characterization of the Attachment Site of Bacteriophage U153 within the Listeria monocytogenes comK Gene " ASM Meeting, Abstract 1999.
Lauer et al., "Systematic mutational analysis of the amino-terminal domain of the Listeria monocytogenes ActA protein reveals novel functions in actin-based motility" Molecular Microbiology 42(5):1163-1177, 2001.
Lauer, et al., "Construction, characterization, and use of two LM site-specific phageintegration vectors", 2002 J Bacteliol, 184:4177-4186.
Leao et al., 1995, "A species-specific nucleotide sequence of *Mycobacterium tuberculosis* encodes a protein that exhibts hemolytic activity when expressed in *Escherichia coli*" Infect. Immun. Nov.; 63(11):4301-6.
Lebrun et al., Aug. 1996, "Internalan must be on the Bacterial Surface to mediate Entry of Listeria monocytogenes into Epilhalial Cells", Molecullar Microbiology 21:579-592.
Le Doussal et al. Enhanced In Vivo Targeting of an Asymmetric Bivalent Hapten Antibody Conjugate CocktailsTo Double-Antigen-Positive Mouse B Cells With Monoclonal ; J. Immunol. 146:169-175 (1991).
Lee et al., 1991, "Construction of single-copy integration vectors for *Staphylococcus aureus*", Gene 103:101-5.
Lee et al. Delivery of macromolecules into cytosol using liposomes containig hemolysin from Listeria monocytogenes, J. Biol. Chem., Mar. 29, 1996 271(13):7249-52.
Lehner et al., 1996, "Processing and delivery of peptides presented by MHC class I molecules", Curr. Opin. Immunol. 8(1):59-67.
Lejeune, 1994, "Nitric oxide involvement in tumor-induced immunosuppression" J. Immunol. 152(10):5077-5083.
Lenz, "Stable integration vector for nutrient broth-based selection of attenuated Listeria monocytogenes strains with recombinant antigen expression" Clin Vaccine Immunol. 15(9):1414-1419. Sep. 2008.
Li et al., "Conditional lethality yields a new vaccine strain of listeria monocytogenes for the induction of cell-mediated immunity", Infection and Immunity, 2005, 73(8): 5065-5073.
Liau et al., 2002, "Tumor immunity within the central nervous system stimulated by recombinant Listeria monocytogenes vaccination", Cancer Res., 62(8):2287-93.
Lieberman et al. "Engineered Listeria monocytogenes as an AIDS vaccine", Vaccine. May 6, 2002;20(15):2007-10.
Lin et al., "Treatment of Established Tumors with a Novel Vaccine that Enhances Major Histocompatibility Class II Presentation of Tumor Antigen", Cancer Res. 1996, 56:21-26.
Lin et al., 2002, "Oral vaccination with recombinant Listeria monocytogenes expressing human papillomavirus type 16 E7 can cause tumor growth in mice to regress" Int. J. Cancer, Dec. 20; 102(6):629-37.
Lingnau et al., 1995, "Expression of the Listeria monocytogenes EGD inlA and inlB genes, whose products mediate bacterial entry into tissue culture cell lines, by PrfA-dependent and independent mechanisms" Infect. Immun. Oct.; 63(10):3896-903.
Lipford et al. "Vaccination with immunodominant peptides encapsulated in Quil A-containing liposomes induces peptide-specific primary CD8+ cytotoxic T cells", Vaccine Jan. 1994; 12(1):73-80.
Lipsky et al. "Infliximab and Methotrexate in the Treatment of Rheumatoid Arthritis" (2000) New Engl. J. Med. 343:1594-1602.
Liu et al. "Randomised, double blind, placebo controlled study of interferon beta-1a in relapsing-remitting multiple sclerosis analysed by area under disability/time curves" (1999) J. Neurol. Neurosurg. Psych. 67:451-456.
Lobocka et al. "Organization and expression of the *Escherichia coli* K-12 dad operon encoding the smaller subunit of D-amino acid dehydrogenase and the catabolic alanine racemase", J Bacteriol. Mar. 1994;176(5):1500-10.
Loeffler et al., 2006, "Comparison of different live vaccine strategies in vivo for delivery of protein antigen or antigen-encoding DNA and mRNA by virulence-attenuated Listeria monocytogenes" Infect. Immun. Jul.; 74(7):3946-57.

(56) References Cited

OTHER PUBLICATIONS

Loessner et al., 1995, "Heterogeneous endolysins in Listeria monocytogenes bacteriophages: a new class of enzymes and evidence for conserved holin genes within the siphoviral lysis cassettes", Mol. Microbiol. Jun.; 16(6):1231-41.
Loessner et al., 2000, "Complete nucleotide sequence, molecular analysis and genome structure of bacteriophage A118 of Listeria monocytogenes: implications for phage evolution", Molecular Microbiology 35(2):324-40.
Loessner et al. 1994. Structural proteins and DNA characteristics of 14 Listeria typing bacteriophages. J. Gen. Virol. 75:701-710.
Ma et al. "Expression of HER-2 in Human Osteosarcoma" Science Technology and Engineering. 2011;13:037.
Maciag et al. "The First clinical use of a live-attenuated Listeria monocytogenes vaccine: A Phase I safety study of Lm-LLO E7 in patients with advanced carcinoma of the cervix", Vaccine, Elsevier LTD, GB, vol. 27, No. 30, pp. 3975-3983. (2009).
Madden et al. Applications of Network BLAST Server; Meth. Enzymol. 266:131-141 (1996).
Makela et al., Hand book of Experimental Immunology vol. 1, Chapter 3—"Haptens and carriers", pp. 3.1-3.13; 1987.
Manjili et al., 2003, "HSP110-HER2/neu chaperone complex vaccine induces protective immunity against spontaneous mammary tumors in HER-2/neu trangenic mice" J. Immunol. Oct. 15; 171(8):4054-61.
Marks et al. By-passing Immunization Human Antibodies from V-gene Libraries Displayed on Phage; J. Mol. Biol. 222: 581-597 (1991).
Marquis et al., 1997, "Proteolytic pathways of activation and degradation of a bacterial phospholipase C during intracellular infection by Listeria monocytogenes" J. Cell Biol. 137:1381-1392.
Marquis et al. "Intracytoplasmic growth and virulence of Listeria monocytogenes auxotrophic mutants", Infect Immun. Sep. 1993;61(9):3756-60.
Martin et al., 1986, "Nucleotide sequence of the tetM tetracycline resistance determinant of the streptococcal conjugative shuttle transposon Tn1545", Nucleic Acid Res. 14:7047-7058.
Marx et al., 2002, "Broad-host-range cre-lox system for antibiotic marker recycling in gramnegativ bacteria" Biotechniques, Nov.; 33(5):1062-7.
Mata et al. Th1 T.cell responses to HIV-1 Gag protein delivered by Listeria monocytogenes vaccine are similar to those induced by endogenous listerial antigen's; J. Immunol 163:1449-1456. (1999).
Mata et al. Evaluation of a recombinant Listeria monocytogenes expressing an HIV protein that protects mice against viral challenge; Vaccine 19:1435-45, (2001).
Mata (1997). A hexameric phosphorothioate oligonucleotide telomerase inhibitor arrests growth of Burkitt's lymphoma cells in vitro and in vivo. Toxicol. Appi. Pharmacol. 144:189-197.
Mazda, O., et al. (1997) Extremely efficient gene transfection into lympho-hematopoietic cell lines by Epstein-Barr virus-based vectors. J. Immunol. Methods 204, 143-151.
Mazzaccaro et al. "Major histocompatibility class I presentation of soluble antigen facilitated by Mycobacterium tuberculosis infection", Proc. Natl. Acad. Sci. U.S.A. Oct. 15, 1996; 93(21):11786-91.
McLaughlan et al., 1998, "Molecular characterization of an autolytic amidase of Listeria monocytogenes EGD", Microbiology, May; 144(Pt 5):1359-67.
Mendez et al. Functional Transplant of Megabase Humanimmunoglobulin Loci Recapitulates Human Antibody Response in Mice; Nature Genetics 15:146-156 (1997).
Mengaud et al., 1988, "Expression in Escherichia coli and sequence analysis of the listeriolysin O determinant of listeria monocytogenes", Infect. Immun., vol. 56, No. 4, 766-772.
Mengaud et al., "Transcriptional mapping and nucleotide sequence of the Listeria monocytogenes hlyA region reveal structural features that may be involved in regulation" Infect. Immun. 1989 57, 3695-3701.

Menne, et al. "A comparison of signal sequence predition methods using a test set of signal peptides" (2000) Bioinformatics 16: 741-742.
Merrifield et al., "Solid phase peptide synthesis. 1. The synthesis of a tetrapeptide" J. Am. Chem. Soc., 85:2149-2156 (1963).
Meyaard et al. "LAIR-1, a Novel Inhibitory Receptor Expressed on Human Mononuclear Leukocytes" (1997) Immunity 7:283-290.
Mikayama et al. "Molecular cloning and functional expression of a cDNA encoding gycosylation-inhibiting factor", Nov. 1993, Pro Natl. Acad. Sci., USA, vol. 90:10056-10060.
Milgrom et al. "Treatment of Allergic Asthma With Monoclonal Anti-Ige Antibody" (1999) New Engl. J. Med. 341:1966-1973.
Miller et al. Targeted vectors for gene therapy, FASEB J. 9, 190-199 (1995).
Milligan et al. Current Concepts in Antisence Drug Design; J. Med Chem 36 1923-1937; (1993).
Mkrtichyan et al. "Anti-PD-1 antibody significantly increases therapeutic efficacy of Listeria monocytogenes (Lm)-LLO immunotherapy", Journal for ImmunoTherapy of Cancer 2013, 1:15.
Mlynarova et al., 2002, "The promiscuity of heterospecific lox sites increases dramatically in the presence of palindromic DNA", Gene, Aug. 21; 296(1-2):129-37.
Mollet et al., 1993, "Directed genomic integratoin, gene replacement, and integrative gene expression in Streptococcus thermophilus" J. Bacteriology 175:4315-4324.
Moriishi et al., 1998, "Sequence analysis of the actA gene of Listeria monocytogenes isolated from human", Microbiol. Immunol., vol. 42, No. 2, p. 129-132.
Mustafa et al., "Listeria Monocytogenes delivery of HPV-16 major capsid protein L1 induces systemic and mucosal cell-mediated CD4+ and CD8+ T-cell responses after oral immunization", Viral Immunology, 2009, vol. 22, No. 3, pp. 195-204.
Nagai et al. 1991 Isolation and partial characterization of major protein antigens in the culture fluid of Mycobacterium tuberculosis. Infect Immun. Jan. 1991;59(1):372-82.
Nakanuma, et al. Anatomic and molecular pathology of intrahepatic cholangiocarcinoma, J. Hepatobiliary Pancreat. Surg. 10:265-281 (2003).
Narang et al. (1979). Improved Phosphotriester Method for the Synthesis of Gene Fragments, Meth. Enzymol. 68: 90-99.
Naruishi et al (Adenoviral vector-mediated RTVP-1 gene-modified tumor cell-based vaccine suppresses the development of experimental prostate cancer. Cancer Gene Ther. Jul. 2006;13(7):658-63).
Ngo et al., 1994, "The Protein Folding Problem and Tertiary Structure Prediction", pp. 492-495.
Nielsen Pe,(1999). Peptide nucleic acids as therapeutic agents Current Opin Struct Biol 9:353-57.
Nikodinovic et al., A second generation snp-derived Escherichia coli-Streptomyces shuttle expression vector that is generally transferable by conjugation. Plasmid. Nov. 2006;56(3):223-7.
Nitcheu-Tefit et al. Listeriolysin O Expressed in a Bacterial Vaccine Suppresses CD4+ CD25high Regulatory T Cell Function in Vivo, J. Immunol. 179(3):1532-41(2007).
Nomi et al. Clinical significance and therapeutic potential of the programmed death-1 ligand/programmed death-1 pathway in human pancreatic cancer. Clinical Cancer Research (2007);13:2151-2157.
Noriega et al. "Engineered deltaguaB-A deltavirG Shigella flexneri 2a strain CVD 1205: construction, safety, immunogenicity, and potential efficacy as a mucosal vaccine", Infect Immun. Aug. 1996;64(8):3055-61.
Ochsenbein et al., 1999, "A comparison of T cell memory against the same antigen induced by virus versus intracellular bacteria" Proc. Natl. Acad Sci U.S.A. Aug. 3; 96(16):9293-8.
Offit et al. "Addressing Parents' Concerns: Do Multiple Vaccines Overwhelm or Weaken the Infant's Immune System?", Pediatrics vol. 109 No. 1 Jan. 2002.
Ogasawara Database EMBL, Oct. 13, 1997, "Bacillus subtilis Genome Sequence".
Ogasawara et al A strategy for making synthetic peptide vaccines Proc. Nati. Acad. Sci. USA vol. 89, pp. 8995-8999, Oct. (1992).

(56) References Cited

OTHER PUBLICATIONS

Ohigashi et al. Clinical significance of programmed death-1 ligand-1 and programmed death-1 ligand 2 expression in human esophageal cancer. Clin. Cancer Research (2005): 11: 2947-2953.

O'Riordan et al. Listeria Intracellular Growth and Virulence Require Host-Derived Lipoic Acid, Science 302: 462-464(2003).

Oscarsson et al., 1996, "Induction of haemolytic activity in *Escherichia coli* by the slyA gene product" Mol. Microbiol. Apr.; 20(1):191-9.

Paglia et al., 1997, "The defined attenuated Listeria monocytogenes delta mp12 mutant is an effective oral vaccine carrier to trigger a long-lasting immune response against a mouse fibrosarcoma" Eur. J. Immunol. 27:1570-1575.

Palmeros et al., 2000, "A family of removable cassettes designed to obtain antibiotic-resistance-free genomic modifications of *Escherichia coli* and other bacteria" Gene, Apr. 18; 247(1-2):255-64.

Pamer et al. "Precise prediction of a dominant class I MHC-restricted epitope of Listeria monocytogenes", Nature. Oct. 31, 1991;353(6347):852-5.

Pan et al., "Regression of Established Tumors in Mice Mediated by the Oral Administration of a Recombinant Listeria monocytogenes Vaccine", Cancer Res., 1995, 55:4776-4779.

Pan et al., 1995, "A recombinant Listeria monocytogenes vaccine expressing a model tumour antigen protects mice against lethal tumour cell challenge and causes regression of established tumours" Nature Med. 1:471-477.

Parida et al., 1998, "Internalin B is essential for adhesion and mediates the invasion of Listeria monocytogenes into human endothelial cells" Mol. Microbiol. Apr.; 28(1):8193.

Parsa et al., "Engineering bacterial vectors for delivery of genes and proteins to antigen-presenting cells", Molecular Pharmaceutics, vol. 4, No. 1, 2007, pp. 4-17.

Passos et al. Recombinant Leishmania Antigens for Serodiagnosis of Visceral Leishmaniasis Clinical and Diagnostic Laboratory Immunology, Oct. 2005, p. 1164-1167, vol. 12, No. 10.

Paterson et al., "Listeria-based vaccines for cancer treatment", Current Opinion in Molecular Therapeutics, vol. 7, No. 5, 2005, pp. 454-460.

Paterson, "Rational approaches to immune regulation", Immunologic Research, 2003; 27/2-3:451-462.

Paterson et al. "Recombinant Listeria monocytogenes cancer vaccines", Curr Opin Immunol. Oct. 1996;8(5):664-9.

Paul et al., 1989, "Fundamental Immunology", Second Edition, Raven Press, 987-988.

Paul et al. Frequent associations between CTl and T-Helper epitopes in HIV-1 genomes and 12, 13 implications for multi-epitope vaccine designs. BMC Microbiology 10:1-16 (2010).

Paul, W. E. et al. An IL-4 Receptor Region Containing an Insulin Receptor Motif Is Important for IL+Mediated IRS-1 Phosphorylation and Cell Growth, Cell 76 241-251 (1994).

Pawelek et al. "Tumor-targeted *Salmonella* as a novel anticancer vector", Cancer Res. Oct. 15, 1997;57(20):4537-44.

Peng et al. "Adjuvant properties of listeriolysin O in a DNA vaccine strategy", Cancer Immunol Immunother, Jun. 2007;56(6):797-806.

Penichet et al., 2001, "Antibody-cytokine fusion proteins for the therapy of cancer" J. Immunological Methods 248:91-101.

Peters et al. "Tailoring host immune responses to Listeria by manipulation of virulence genes—the interface between innate and acquired immunity", FEMS Immunol Med Microbiol. Apr. 1, 2003;35(3):243-53.

Peters,C et al. The Induction of HIV Gag-Specific CD8+ T Cells in the Spleen and Gut-Associated Lymphoid Tissue by Parenteral or Mucosal monocytogenes HIV Gag Immunization with Recombinant Listeria; J Immunol; 170:5176-5187 ( 2003).

Peters, C and Y. Paterson. Enhancing the immunogenicity of bioengineered Listeria monocytogenes by passaging through live animal hosts. Vaccine. 21.:1187-94. (2003).

Pfeifer et al., 1993, "Phagocytic processing of bacterial antigens for class I MHC presentation to T cells" Nature, Jan. 28; 361(6410):359-62.

Portielji et al. IL-12: a promising adjuvant for cancer vaccination, Cancer Immunol. Immunother. 52:133-144 (2003).

Portnoy et al. "Molecular determinants of Listeria monocytogenes pathogenesis", Infect Immun. Apr. 1992;60(4):1263-7.

Presta "Selection, design, and engineering of therapeutic antibodies" (2005) J. Allergy Clin. Immunol. 116:731.

Pucci et al, "*Staphylococcus haemolyticus* Contains Two D-Glutamic Acid Biosynthetic Activities, a Glutamate Racemase and a D-Amino Acid Transaminase" 1995, J Bacteriol. 177: 336-342.

Pupa et al., 2001, "Prevention of spontaneous neu-expressing mammary tumor development in mice transgenic for rat proto-neu by DNA vaccination" Gene Ther. Jan.; 8(1):75-9.

Purchio et al. "Methods in Enzymology: Methods for molecular cloning in eukaryotic cells", (2003).

Quenee et al., 2005, "Combined sacB-based negative selection and cre-lox antibiotic marker recycling for efficient gene deletion in pseudomonas aeruginosa", Biotechniques, Jan.; 38(1):63-7.

Raveneau et al., 1992, "Reduced virulence of a Listeria monocytogenes phospholipase-deficient mutant obtained by transposon insertion into the zinc metalloproteas gene" Infect. Immune., 60:916-921.

Realini et al., "Proposed roles in protein-protein association and presentation of peptides by MHC Class I receptors", FEBS Lett., 1994, 348:109-113.

Rechsteiner et al (PEST sequences and regulation by proteolysis. Trends Biochem Sci 1996; 21(7):267-71.

Reiter et al., 1989, "Transfer RNA genes frequently serve as integration sites for porkaryotic genetic elements", Nucleic Acids Research 17(5):1907-14.

Renard et al., "HER-2 DNA and protein vaccines containing potent Th cell epitopes induce distinct protective and therapeutic antitumor responses in HER-2 transgenic mice", The Journal of Immunology, 171(3):1588-1595, 2003.

Repique, 1992, "Immunosuppression derived from human B-lymphoblastoid and melanoma cell lines" Cancer Invest. 10(3):201-208.

Riegler, J. Preneoplastic Conditions of the Liver; Seminars in Gastrointestinal Disease vol. 7, No. 2:pp. 74-87 (1996).

Riera et al. Evaluation of a latex agglutination test (KAtex) for detection of Leishmania antigen in urine of patients with HIV-Leishmania coinfection: value in diagnosis and post-treatment follow-up. Eur J Clin Microbiol Infect Dis. Dec.;23 (12):899-904 (2004).

Robinson, H. L., New Hope for an Aids Vaccine; Nat. Rev. Immunol. 2:239-50 (2002).

Rocken et al. Pathology and Pathogenesis of Hepatocellular, Digestive Diseases 19:269-278 (2001).

Roden et al., 2004, "Vaccination to prevent and treat cervical cancer", Hum. Pathol. 35(8):971-82.

Rogers S et al. Amino acid sequences common to rapidly degraded proteins: the PEST hypothesis. Science; 234(4774):364-8(1986).

Rongcun et al. "Identification of new HER2/neu-derived peptide epitopes that can elicit specific CTL against autologous and allogeneic carcinomas and melanomas." The Journal of Immunology 163.2 (1999): 1037-1044.

Rothman et. al. "The use of living listeria monocytogenes as an active immunotherapy for the treatment of cancer", Emerging Cancer Therapy: Microbial Approaches and Biotechnological Tools, Edited by Arsénio M. Fialho and Ananda M. Chakrabarty Copyright © 2010 John Wiley & Sons, Inc.

Rubin et al. "Cloning, sequence determination, and regulation of the ribonucleotide reductase subunits from Plasmodium falciparum: a target for antimalarial therapy", Proc Natl Acad Sci U S A. Oct. 15, 1993;90(20):9280-4.

Russmann et al., 1998, "Delivery of epitopes by the *Salmonella* type III secretion system for vaccine system for vaccine development", Science, Jul. 24; 281(5376):565-8.

(56) References Cited

OTHER PUBLICATIONS

Safley et al. "Role of listeriolysin-O (LLO) in the T lymphocyte response to infection with Listeria monocytogenes. Identification of T cell epitopes of LLO" J. Immunology 146(10):3604-3616; May 1991.
Sambrook et al. "Molecular cloning: a laboratory manual", Cold Spring Harbor Laboratory Press, Cold Spring Harbor, New York 2 (2001).
Samstag (1996). Synthesis and properties of new antisense oligodeoxynucleotides containing benzylphosphonate linkages. Antisense Nucleic Acid Drug Dev. 6:153-156.
Schafer et al. "Induction of a cellular immune response to a foreign antigen by a recombinant Listeria monocytogenes vaccine", J Immunol. Jul. 1, 1992;149(1):53-9.
Scheirlinck et al., 1989, "Integration and expression of alpha-amylase and endoglucanase genes in the Lactobacillus plantarum chromosome", Appl. Environ Microbiol. 55(9):2130-7.
Scher et al., (2008) "Design and End Points of Clinical Trials for Patients With Progressive Prostate Cancer and Castrate Levels of Testosterone: Recommendations of the Prostate Cancer Clinical Trials Working Group" J. Clin. Oncol. 26(7):1148-159.
Schmidt et al., 1995, "Molecular Analysis of the Plasmid-Encoded Hemolysin of *Escherichia coli* O157:H7 Strain EDL 933", Infection and Immunity, 63(3):1055-1061.
Schneider et al. Induction of CD8+ T cells using heterologous prime-boost immunisation strategies, Immunol.Rev. 170:29-38 (1999).
Schnupf et al., "Phosphorylation, ubiquitination and degradation of listeriolysic O in mammalian cells: role of the PEST-like sequence" Cellular microbiology 8(2):353-364, 2006.
Schnupf et al. "ListeriolysinO: a phagosome-specific lysine", Microbes & Infect. 2007, 9:1176-1187.
Scortti et al., 2007, "The PrfA virulence regulon", Microbes Infect. Aug.; 9(10):1196-207.
Scott et al. Amino Acid Sequences Common to Rapidly Degraded Proteins: The PEST Hypothesis; Immunol. Today vol. 234 364-348.,(1991).
Seavey MM. "A novel human Her-2/neu chimeric molecule expressed by Listeria monocytogenes can elicit potent HLA-A2 restricted CD8-positive T cell responses and impact the growth and spread of Her-2/neu-positive breast tumors" Clin Cancer Res. 15(3):924-32, Feb. 1, 2009.
Sehgal et al "Prostate cancer cells show elevated urokinase receptor in a mouse model of metastasis" Cancer Cell Int. Aug. 23, 2006;6:21.
Sewell et al., "Recombinant Listeria Vaccines Containing PEST Sequences are potent immune adjuvants for the tumor-associates antigen human pappilomavirus-16 E7", Cancer Research, American Association for Cancer Research, vol. 64, No. 24, 2004, pp. 8821-8825.
Sewell et al. Regression of HPV-Positive Tumors Treated with a New Listeria monocytogenes Vaccine Arch Otolaryngol., Head Neck Surg., Jan. 2004, vol. 130, pp. 92-97.
Shahabi et al. Development of a live and highly attenuated Listeria monocytogenes-based vaccine for the treatment of Her2/neu-overexpressing cancers in human; Nature America, Inc, Cancer Gene Therapy (2010), 1-10 (2010).
Shahabi et al. Development of a Listeria monocytogenes based vaccine against prostate cancer, Cancer Immunol Immunother; 57:1301-1313 (2008).
Shahabi et al. "A live, attenuated Listeria-based immunotherapeutic for the treatment of breast cancer", 2009 ASCO Breast cancer Symposium, Oct. 8, 2009, abstract.
Shahabi et al. "Development of a live and highly attenuated Listeria monocytogenes based vaccine for the treatment of Her2/neu-overexpressing cancers in human", Cancer Gene Therapy, vol. 18, No. 1, Jan. 1, 2011, pp. 53-62.
Shahabi et al., "Live, attenuated strains of Listeria and *Salmonella* as vaccine vectors in cancer treatment", Bioeng. Bugs, 2010, vol. 1, No. 4, pp. 235-243.
Sharpe et al. The function of programmed cell death 1 and its ligands in regulating autoimmunity and infection. Nature Immunology ; 8:239-245 (2007).
Shaw et al. "Complete nucleotide sequence of macrolide-lincosamide-streptogramin B-resistance transposon Tn917 in *Streptococcus faecalis*", J Bacteriol. Nov. 1985; 164(2):782-96.
Shen et al., 1995, "Recombinant Listeria monocytogenes as a live vaccine vehicle for the induction of protective anti-viral cell-mediated immunity" Proc. Nat'l Acad Sci U.S.A., 92(9):3987-91.
Shen et al., 1998, "Compartmentalization of bacterial antigens: diffrential effects on priming of CD8 T cells and protective immunity" Cell., Feb. 20; 92(4):535-45.
Shetron-Rama et al., 2002, "Intracellular induction of Listeria monocytogenes actA expression" Infect. Immun. 70:1087-1096.
Shimauchi T et al. Augmented expression of programmed death-1 in both neoplasmatic and nonneoplastic CD4+ T-cells in adult T-cell Leukemia/ Lymphoma. Int. J. Cancer (2007): 121:2585-2590.
Shimizu et al., 1994, "Effects of CD4+ and CD8+ T cells in tumor-bearing mice on antibody production" Cancer Immunol. Immunother 38(4):272-276.
Shiver J. W. et al., Replication-incompetent adenoviral vaccine vector elicits effective antiimmunode ®ciency-virus immunity, Nature 415: 331-5 (2002).
Sin et al. DNA Priming—Protein Boosting Enhances Both Antigen-Specific Antibody and Th1-Type Cellular Immune Responses in a Murine Herpes Simplex Virus-2 gD Vaccine Model, DNA Cell Biol. 18:771-9 (1999).
Singh et al. "Immunoediting Sculpts Tumor Epitopes during Immunotherapy" Cancer Res;67:1887-1892.(2007).
Singh et al., "Cancer immunotherapy using recombinant Listeria monocytogenes transition from bench to clinic", Human Vaccines, 2011, vol. 7(5), pp. 497-505.
Singh et al., "Fusion to Listeriolysin O and Delivery by Listeria monocytogenes Enhances the Immunogenicity of HER-2/neu and Reveals Subdominant Epitopes in the FVB/N Mouse", The Journal of Immunology 2005, vol. 175, No. 6, pp. 3663-3673.
Sirard et al., 1997, "Intrtracytoplasmic delivery of Lidteriolysin O by vaccinal strain of Bacillus anthracis induces CD8-mediated protection against listeria monocytogenes", J. Immunology, vol. 159, p. 4435-4443.
Sizemore et al. "Attenuated Shigella as a DNA delivery vehicle for DNA-mediated immunization", Science. Oct. 13, 1995;270(5234):299-302.
Skoble, et al. "Three Regions within ActA Promote Arp2/3 Complex-mediated Actin Nucleation and Listeria monocytogenes Motility" 2000, J. Cell Biol. 150: 527-538.
Skolnick et al. "Form genes to protein structure and function: novel applications of computational approaches in the genomic era", Jan. 2000, Trends in Biotech., 18(1):34-39.
Slamon et al. "Use of Chemotherapy Plus a Monoclonal Antibody Against Her2 for Metastatic Breast Cancer That Overexpresses Her2" 2001, New Engl. J. Med. 344:783-792.
Slifka et al., 1996, "Antiviral cytotoxic T-cell memory by vaccination with recombinant Listeria monocytogenes" J. Virol. 70(5):2902-10.
Smith et al., 1995, "The two distinct phospholipases C of Listeria monocytogenes have overlapping roles in escape from a vacuole and cell-to-cell spread", Infect. Immun. 63:4231-4237.
Smith et al., Sep. 1995, "Asymmetric Distribution of the Listeria monocytogenes ActA Protein is Required and Sufficient to Direct Actin-Based Motility", Molecular Microbiology 17:945-951.
Smith et al. Biochimie. 1992. Use of a new integrational vector to investigate comparement-specific expression of the Bacillus subtilis spoIIM gene; 74 (7-8) p. 705-711.
Souders et al., 2006, "In vivo bactofection: listeriacan function as a DNA-cancer vaccine" DNA Cell Biol. Mar.; 25(3):142-51.
Soussie et al., "Listeria monocytogenes as a short lived delivery system for the induction of type 1 cell-mediated immunity againdt the p36/LACK antigen of Leishmania major", Infection and Immunity, vol. 68, No. 3, 2000, pp. 1498-1506.
Stahl et al., 1984, "Replacement of the Bacillus subtilisin structural gene with an in vitro-derived deletion mutation", J. Bacteriol. 158:411-418.

(56) References Cited

OTHER PUBLICATIONS

States et al. Improved Sensitivity of Nucleic Acid Database Searches Using Application-Specific Scoring Matrices, Methods 3:66-70 (1991).
Stitz et al., 1990, "Characterization and immunological properties of influenza a virus nucleoprotein (NP): cell-associated NP isolated from infected cells or viral NP expressed by vaccinia recombinant virus do not confer protection" J. Gen. Virol., 71(Pt 5):1169-1179.
Strauss-Soukup, "Effects of Neutralization Pattern and Stereochemistry on DNA Bending by Methylphosphonate Substitutions ", 1997, Biochemistry 36:8692-8698.
Strungnell et al., 1990, "Stable expression of forgein antigens from the chromosome of *Salmonella typhimurium* vaccine strains", Gene 88:57-63.
Strych et al. "Characterization of the alanine racemases from two mycobacteria", FEMS Microbiol Lett. Mar. 15, 2001;196(2):93-8.
Strych et al, "Mutant Analysis Shows that Alanine Racemases from Pseudomonas aeruginosa and *Escherichia coli* Are Dimeric" 2002, J. Bacteriol. 184:4321-4325.
Stryer et al., "Levels of structure in protein architecture", Biochemistry, Third Edition, W H Freeman Company, New York, pp. 31-33, 1998.
Su et al., "Relevance of Hepatic Preneoplasia for Human Hepatocarcinogenesis" (2003) Toxicol. Pathol. 31:126-133.
Sun et al. Isolation of Listeria monocytogenes Small-Plaque Mutants Defective for Intracellular Growth and Cell-to-Cell Spread, Nov., Infection and Immunity, vol. 58, No. 11, p. 3770-3778 (1990).
Supplementary European Search Report for European Application No. 11863004.5 dated Nov. 10, 2015.
Szalay et al. "Presentation of Listeria monocytogenes antigenes by major histocompatibility complex class I molecules to CD8 cytotoxic T lymphocytes independent of listeriolysin secretion and virulence", Eur. J. Immunol. Jul. 1994; 24(7):1471-7.
Tanabe et al., "Induction of Protective T Cells against Listeria monocytogenes in Mice by Immunization with a Listeriolysin O-Negative Avirulent Strain of Bacteria and Liposome-Encapsulated Listeriolysin O", Infect. Immun., 1999, 67(2):568-575.
Tang et al., "Protein Chemistry and Structure: Use of a Peptide Mimotope to Guide the Humanization of MRK-16, an Anti-P-glycoprotein Monoclonal Antibody", 1999 J. Biol. Chem. 274:27371-27378.
Tanghe, A., "Improved Immunogenicity and Protective Efficacy of a Tuberculosis DNA Vaccine Encoding Ag85 by Protein Boosting" Infect. Immun. 69:3041-7 (2001).
Tanizawa et al. "The primary structure of thermostable D-amino acid aminotransferase from a thermophilic Bacillus species and its correlation with L-amino acid aminotransferases", J Biol Chem. Feb. 15, 1989;264(5):2450-4.
Tanizawa et al. "Thermostable alanine racemase from Bacillus stearothermophilus: DNA and protein sequence determination and secondary structure prediction", Biochemistry. Feb. 23, 1988;27(4):1311-6.
Taube et al. Colocalization of Inflammatory Response with B7-H1 Expression in Human Melanocytic Lesions Supports an Adaptive Resistance Mechanism of Immune Escape, Sci Transl Med 4, 127ra37 (2012).
Tauch et al, "The alanine racemase gene alr is an alternative to antibiotic resistance genes in cloning systems for industrial Corynebacterium glutamicum strains" 2002, J. Biotechnol 99:79-91.
Teitelbaum et al. "Mycobacterial infection of macrophages results in membrane permeable phagosomes", Proc. Natl. Acad. Sci. U.S. A, Dec. 21, 1999, 96(26):15190-5.
Terracciano et al. Cytogenetic alterations in liver cell tumors as detected by Comparitive Genomic Hybridization, Pathologica 95:71-82 (2003).
The Merck Index: An Encyclopedia of Chemicals, Drugs, and Biologicals. Fifteenth Edition, (2013) Item No. 4561. Gonadotropin. pp. 835-836.

Thomas-Kaskel et al (Vaccination of advanced prostate cancer patients with PSCA and PSA peptide-loaded dendritic cells induces DTH responses that correlate with superior overall survival. Int J Cancer. Nov. 15, 2006;119(10):2428-34).
Thompson et al., "Costimulatory B7-H1 in renal cell carcinoma patients: Indicator of tumor aggressiveness and potential therapeutic target" PNAS 101 (49); 17174-17179 (2004).
Thompson et al., "Overall Survival and PD-L1 Expression in Metastasized Malignant Melanoma" Cancer Res. 66:3381-3385 (2006).
Thompson et al. "PD-1 is expressed by tumor infiltrating cells and is associated with poor outcome for patients with renal carcinoma" Clinical Cancer Research (2007) 15: 1757-1761.
Tilney et al., 1989, "Actin filaments and the growth, momvement, and speard of the intracellular bacterial parasite, Listeria monocytogenes" J. Cell Biol., Oct.; 109(4 Pt 1):1597-608.
Toplian et al., "Safety, Activity, and Immune Correlates of Anti-PD-1 Antibody in Cancer" New Eng. J Med. 366 (26): 2443-2454 (2012).
Triglia et al. "A procedure for in vitro amplification of DNA segments that lie outside the boundaries of known sequences", Nucleic Acids Res. Aug. 25, 1988;16(16):8186.
Uenaka et al (T cell immunomonitoring and tumor responses in patients immunized with a complex of cholesterol-bearing hydrophobized pullulan (CHP) and NY-ESO-1 protein. Cancer Immun. Apr. 19, 2007;7:9).
Ulmanen et al, "Transcription and Translation of Foreign Genes in Bacillus subtilis by the Aid of a Secretion Vector" 1985. J. Bacteriol. 162:176-182.
Vasil et al., 1982, "Cloning of a phosphate-regulated hemolysin gene (phospholipase C) from Pseudomonas aeruginosa" J. Bacteriol. Oct.; 152(1):431-40.
Vaughan et al. Human Antibodies with Sub-nanomolar Affinities Isolated from a Large Non-immunized Phage Display Library, Nature Biotechnol. 14:309-314 (1996).
Vazquez et al. Differential regulation of la expression and antigen presentation by listeriolysin-producing versus non-producing strains of Listeria monocytogenes, J. Leukoc Biol. May 1996; 59(5):683-90.
Vazquez-Boland et al., 1992, "Nucleotide sequence of the lecithinase operon of Listeria monocytogenes and possible role of lecithinase in cell-to-cell spread" Infect. Immun. 60:219-230.
Verch et al., Listeria monocytogenes-Based Antibiotic Resistance Gene-Free Antigen Delivery System Applicable to Other Bacterial Vectors and DNA Vaccines. Infect Immun, 2004. 72(11):6418-25.
Verma et al., 1995, "Delivery of class I and class II MHC-restricted T-cell epitopes of listeriolysin of listeria monocytogenes by attenuated *Salmonella*", Vacine, vol. 13, No. 2, p. 142-150.
Villanueva et al. "Listeriolysin is processed efficiently into an MHC class I-associated epitope in Listeria monocytogenes-infected cells", J. Immunol. Dec. 1, 1995; 155(11):5227-33.
Vines et al. "Identfication and characterization of nucleotide sequence difference in three virulence-associate genes of listeria monocytogenes strains representing clinically important serotypes", Current Microbiology, May 1998, vol. 36, No. 5, pp. 309-318.
Von Heijne. Patterns of Amino Acids near Signal-Sequence Cleavage Sites Eur. J. Biochem. 133:17-21 (1983).
Von Heijne, "A new method for predicting signal sequence cleavage sites" (1986) Nucleic Acids Res. 14:4683-4690.
Walker et al., 1994, "Tumor growth Alters T cell and macrophage production of and responsiveness to granulocyte-macrophage colony-stimulating factor: partial dysregulation through interleukin-10" Cell Immunol. 154(1):342-357.
Wallecha et al. "Construction and characterization of an attenuated Listeria monocytogenes strain for clinical use in cancer immunotherapy" Clin Vaccine Immunol. 16(1):96-103, Jan. 2009.
Wallecha et al., "Multiple effector mechanisms induced by recombinant listeria monocytogenes anticancer immunotherapeutics", Advances in Applied Microbiology, vol. 66, 2009, pp. 1-27.
Ward et al. 1986. Construction and characterisation of a series of multi-copy promoter-probe plasmid vectors for Streptomyces using the aminoglycoside phosphotransferase gene from Tn5 as indicator, Mol. Gen. Genet. 203:468-478.

(56) References Cited

OTHER PUBLICATIONS

Wasserman et al. "Catabolic alanine racemase from *Salmonella typhimurium*: DNA sequence, enzyme purification, and characterization", Biochemistry. Oct. 23, 1984;23(22):5182-7.
Watson et al., 1991, "Splenic macrophages from tumor-bearing mice co-expressing MAC-1 and MAC-2 antigen exert immunoregulatory functions via two distinct mechanisms" J. Leukoc Biol. 49(2):126-138.
Weber, "Assessing Tumor Response to Therapy" Nucl. Med. 50:1S-10S (2009).
Wei et al., 2005, "Listeria monocytogenes phosphatidylinositol-specific phospholipase C has evolved for virulence by greatly reduced activity on GPI anchors" Proc. Natl. Acad. Sci. U.S.A. 102:12927-12931.
Weidt et al., 1994, "CD8+ T lymphocyte-mediated antiviral immunity in mice as a result of injection of recombinant viral proteins", J. Immunol. Sep. 15; 153(6):2554-61.
Weiskirch "Listeria monocytogenes: a potent vaccine vector for neoplastic and infectious disease" Immunol. Rev., vol. 158, Aug. 1997, p. 159-169.
Welch et al., Jul. 3, 1998, "Interaction of Human Arp2/3 Complex and the Listeria monocytogenes ActA Protein in Actin Filament Nucleation" Science 281:105-108; pa-998020.
Wilson et al. "Transient expression of bacterial gene fragments in eukaryotic cells: implications for CD8(+) T cell epitope analaysis", J. Immunol. Methods, Feb. 3, 2000; 234 (1-2):137-47.
Wipke et al. "Variable binding affinities of listeriolysin O peptides for the H-2Kd class I molecule", Eur J Immunol. Aug. 1993;23(8):2005-10.
Wirth et al, "Highly efficient protoplast transformation system for *Streptococcus faecalis* and a new *Escherichia coli*-S. faecalis shuttle vector", J Bacteriol, 165: 831, 1986.
Wolff et. al., Direct Gene Transfer into Mouse Muscle in Vivo, Science 247:1465(1990).
Wood et al. "Cancer immunotherapy using Listeria monocytogenes and listerial virulence factors" Immunol Res. ; 42(1-3):233-45. (2008).
Wootton, J.C, et al. Statistics of Local Complexity in Amino Acid Sequences and Sequence Databases, Comput. Chem. 17:149-163 (1993).
Wright et al. "Lymphoid/Neuronal Cell Surface OX2 Glycoprotein Recognizes a Novel Receptor on Macrophages Implicated in the Control of Their Function", (2000) Immunity 13:233-242.
Wu et al. "Engineering an itracellular pathway for major histrocompatibility complex class II presentation of antigens", Proc. Natl. Acad. Sci. USA, 1995, 92:11671-5.
Yang et al. "A Randomized Trial of Bevacizumab, an Anti-Vascular Endothelial Growth Factor Antibody, for Metastatic Renal Cancer" (2003) New Engl. J. Med. 349:427-434.
Yeung et al., "Heat-killed Listeria Monocytogenes as an adjuvant converts established murine TH2-domincated immune responses into TH1-dominated responses", The Journal of Immunology, 1998, vol. 161, No. 8, pp. 4146-4152.
Young et al., 1992, "Tumor-derived cytokines induce bone marrow suppressor cells that mediate immunosuppression through transforming growth factor beta", Cancer Immunol. Immunother. 35(1):14-18.
Young et al., 1995, "Holins: form and function in bacteriophage lysis" FEMS Microbiol Rev., Aug. 17 (1-2):191-205.
Zhang et al., 1993, "Functional replacement of the hemolysin A transport signal by a different primary sequence", Proc. Natl. Acad. Sci. U.S.A May 1; 90(9):4211-5.
Zhang, J., et al., "PowerBLAST: A New Network BLAST Application for Interactive or Automated Sequence Analysis and Annotation " (1997) Genome Res. 7:649-656.
Zhao et al. "Pathogenicity and immunogenicity of a vaccine strain of Listeria monocytogenes that relies on a suicide plasmid to supply an essential gene product", Infect Immun. Sep. 2005;73(9):5789-98.
Zwickey et al. "Antigen secreted from noncytosolic Listeria monocytogenes is processed by the classical MHC class I processing pathway", J. Immunol. Jun. 1, 1999; 162(11):6341-50.
Zwickey et al. "Peptide epitopes from noncytosolic Listeria monocytogenes can be presented by major histocompatibility complex class I molecules", Infect. Immun. May 1996; 64(5):1870-2.
Ma et al. "Expression of HER 2 in Human Osteosarcoma", Sci. Tech. Engng. vol. 11 No. 13 May 2011, 1671 1815( 2011), pp. 3045-3048; abstract.
Broad et al. "The case of the unmentioned malignancy" Science 1980. 210:1229-1230.
Lucey et al. "Henrietta Lacks, HeLa cells, and cell culture contamination" Archives of pathology & laboratory medicine. Sep. 2009;133(9):1463-7.
Gaudy, Amy a., et al. "Fragile X-related protein and Vig associate with the Rna interference machinery." Genes & development 16.19 (2002): 2491-2496. 0.
GenBank [Internet]. Bethesda (Md): National Library of Medicine (US), National Center for Biotechnology Information; Accession No. AF103807.1, Listeria monocytogenes actin nucleator protein ActA (actA) gene; [cited 31-Oct-1998]. Available from:.
GenBank [Internet]. Bethesda (Md): National Library of Medicine (US), National Center for Biotechnology Information; Accession No. NC_003210.1, Listeria monocytogenes Egd-e chromosome, complete genome; [cited 06-Jun-2001]. Available from:.
GenBank [Internet]. Bethesda (Md): National Library of Medicine (US), National Center for Biotechnology Information; Accession No. DQ054588.1, Listeria monocytogenes isolate H4 Hly (hly) gene, complete cds; [cited 07-May-2005]. Available from:.
GenBank [Internet]. Bethesda (Md): National Library of Medicine (US), National Center for Biotechnology Information; Accession No. DQ054589.1, Listeria monocytogenes strain 10403S Hly (hly) gene, complete cds; [cited 07-May-2005]. Available from: https://www.ncbi.nlm.nih.gov/nuccore/66737337 0.
GenBank [Internet]. Bethesda (Md): National Library of Medicine (US), National Center for Biotechnology Information; Accession No. AY878649.1, Listeria monocytogenes strain HCC23 listeriolysin positive regulatory protein (prfA), phosphatidylinositol-specific phospholipase C (plcA), and listeriolysin 0 precursor (hly) genes, complete cds; [cited 06-Jan-2005]. Available from: https://www.ncbi.nlm.nih.gov/nuccore/AY878649 ci.
GenBank [Internet]. Bethesda (Md): National Library of Medicine (US), National Center for Biotechnology Information; Accession No. U25452.1, Listeria monocytogenes F6789 listeriolysin 0 (hly) gene, complete cds; [cited 21-Apr-1995]. Available from:.
Naz, Rajesh K., Ramasamy Santhanam, and Neetu Tyagi. "Novel human prostate-specific cDNA: molecular cloning, expression, and immunobiology of the recombinant protein." Biochemical and biophysical research communications 297.5 (2002): 1075 1084.
Soussi, Neirouz, et al. "Effect of intragastric and intraperitoneal immunisation with attenuated and wild-type Lack-expressing Listeria monocytogenes on control of murine Leishmania major infection." Vaccine 20.21 (2002): 2702-2712.
Wada, Takuro, "Development of Cancer Vaccine Therapy for Bone and Soft Tissue Sarcomas", the Journal of the Japanese Orthopaedic Association, vol. 78(8), S950, English Translation, (2004).

\* cited by examiner

Vaccination (prime±boost) with Listeria expressing HIV gag ± S.mansoni infection

- no schisto, 2X 0.1 LD50
- schisto, unvaccinated
- schisto, 1X i.p. 0.2LD50
- schisto, 2X i.p. 0.1 LD 50 y-axis: IFN-g producing cells per million
x-axis: Restimulation (medium, gag-c, gag-h)

Fig. 7

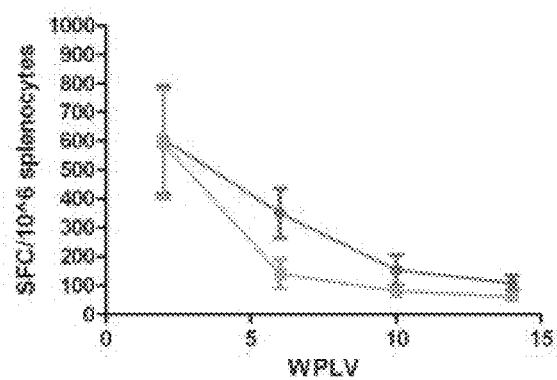
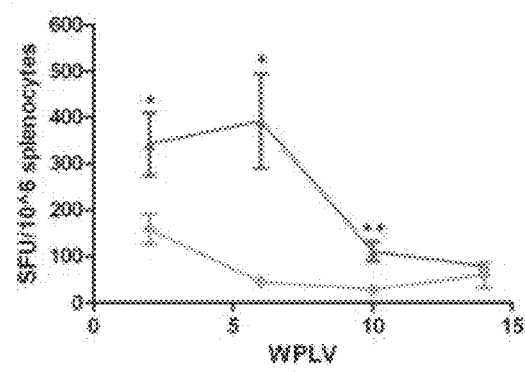
Fig. 13A
Fig. 13B

SEQUENCE LISTING

<160> NUMBER OF SEQ ID NOS: 3

<210> SEQ ID NO 1
<211> LENGTH: 9
<212> TYPE: PRT
<213> ORGANISM: Human immunodeficiency virus

<400> SEQUENCE: 1

Ala Met Gln Met Leu Lys Glu Thr Ile
1               5

<210> SEQ ID NO 2
<211> LENGTH: 9
<212> TYPE: PRT
<213> ORGANISM: Artificial Sequence

```
<220> FEATURE:
<223> OTHER INFORMATION: influenza nucleoprotein peptide

<400> SEQUENCE: 2

Thr Tyr Gln Arg Thr Arg Ala Leu Val
1               5

<210> SEQ ID NO 3
<211> LENGTH: 20
<212> TYPE: PRT
<213> ORGANISM: Human immunodeficiency virus

<400> SEQUENCE: 3

Asn Pro Pro Ile Pro Val Gly Glu Ile Tyr Lys Arg Trp Ile Ile Leu
1               5                   10                  15

Gly Leu Asn Lys
            20
```

USE OF *LISTERIA* VACCINE VECTORS TO REVERSE VACCINE UNRESPONSIVENESS IN PARASITICALLY INFECTED INDIVIDUALS

CROSS-REFERENCE TO RELATED APPLICATIONS

This application is a Divisional application of U.S. patent application Ser. No. 13/876,810, filed Jun. 13, 2013, now U.S. Pat. No. 9,226,958, issued Jan. 5, 2016, which is a National Phase Application of PCT International Application No. PCT/US11/54613, International Filing Date Oct. 3, 2011, claiming priority to U.S. provisional application No. 61/388,822, filed Oct. 1, 2010, and to U.S. provisional application No. 61/409,730, filed Nov. 3, 2010. These applications are hereby incorporated in their entirety by reference herein.

GOVERNMENT INTEREST STATEMENT

This invention was made with government support under grant number(s) AI071883 and AI036657 awarded by National Institute of Health. The government has certain rights in the invention.

FIELD OF THE INVENTION

This invention relates to methods of using a *Listeria* vaccine vector to induce a Th1 immune response in subjects having persistent Th2 immune response profiles due to persistent parasitic infections.

BACKGROUND OF THE INVENTION

Malaria, TB and HIV-1 remain tremendous disease burdens in much of the world's population. Despite decades of effort, there are no vaccines for malaria or HIV-1. Sub-Saharan populations are those that will benefit most from vaccines for malaria, TB and HIV-1. The majority of individuals in sub-Saharan countries, with prevalence exceeding 90% in many areas of Africa, are infected with one or more species of parasitic helminths that suppress immune responses, skew the host immune system of human and animals to T-helper type 2 (Th2), and suppress vaccine-specific responses. Therefore, there is a potential that helminth infected populations may not generate the desired immune responses to vaccines designed to drive Th1-type and cytotoxic T-cell responses. Previous work has shown that a naked DNA vaccine for HIV-1 was unable to generate antigen-specific T cell mediated immune responses unless helminth infection was eliminated prior to vaccination (Da'dara et al., Vaccine. 2010 Feb. 3; 28(5):1310-7. Epub 2009 Nov. 24, incorporated herein by reference in its entirety).

It is clearly important to HIV and other prevalent infectious diseases vaccine development for the developing world, to find a vaccine that will drive significant vaccine-specific Th1 immune responses in parasitically infected recipients.

SUMMARY OF THE INVENTION

In one aspect, the invention relates to a method of inducing a Th1 immune response in a subject having a persistent Th2 phenotypic profile, the method comprising the step of administering to said subject a therapeutically effective dose of a *Listeria* vaccine vector.

In another aspect, the invention relates to a method of inducing a Th1 immune response against an infectious disease in a subject having a persistent Th2 phenotypic profile, the method comprising the step of administering to said subject a therapeutically effective dose of a *Listeria* vaccine vector, wherein the *Listeria* vaccine vector expresses and secretes an infectious disease antigen fused to an additional immunogenic polypeptide, thereby inducing a Th1 immune response in said subject.

In one aspect, the invention relates to a method of treating an infectious disease in a subject having a persistent Th2 phenotypic profile, the method comprising the step of administering to said subject a therapeutically effective dose of a *Listeria* vaccine vector, wherein the *Listeria* vaccine vector expresses and secretes an infectious disease antigen fused to an additional immunogenic polypeptide, thereby treating said infectious disease in said subject.

In another aspect, the invention relates to a method of treating a cancer in a subject having a persistent Th2 phenotypic profile, the method comprising the step of administering to said subject a vaccine comprising a recombinant *Listeria* strain, wherein said vaccine shifts the Th2 phenotype to a Th1 phenotype, allowing for a cell-mediated anti-cancer response to take place.

BRIEF DESCRIPTION OF THE DRAWINGS

The subject matter regarded as the invention is particularly pointed out and distinctly claimed in the specification. The invention, however, may best be understood by reference to the following detailed description when read with the accompanying drawings in which:

FIG. 7 shows that administration of a *Listeria* vector-HIV-1 gag vaccine to mice chronically infected with the helminth parasite *Schistosoma mansoni*, drives significant immune responses to HIV-1 gag CTL and T helper epitopes. The numbers of IFN-γ-producing CD8+ T cells in cells per million from mice immunized with the *Listeria* vector-HIV-1 gag vaccine with or without prior *S. mansoni* infection were compared to unvaccinated controls using IFN-γ ELISPOT assay (mean±S.E.M.). Splenocytes from individual mice (four mice/group) were harvested at 2 weeks after the final vaccination, and stimulated with H2-d-restricted immunodominant CTL and helper peptides for HIV-1 ME gag for 20 h. No spots were detected in cells stimulated with RPMI.

FIGS. 13A-B show cell-mediated immune responses are durable and unaltered by pre-existing chronic helminth infection. Mice were sacrificed at various times post last vaccination and responses of uninfected (green) or schistosome-infected (orange) mice to immunodominant CTL (FIG. 13A) and helper (FIG. 13B) epitopes are shown. Within the effector cell responses to the immunodominant CTL epitope (FIG. 13A), no significant differences ($p<0.05$) were found when comparing each time point±Schistosomiasis with a t-test analysis, indicating the effector cell response to the vaccine is unchanged over time between the groups. For Th1 responses to the helper epitope (B), *$p<0.05$ and **$p<0.01$, when comparing±Schistosomiasis at each time point using t-test analysis.

(FIG. 16A) Graphic representation of in vivo CTL assay. (FIG. 16B) Specific killing by vaccinated groups was plotted and analyzed by one-way ANOVA and Bonferroni. If <100 targets were recovered, data points were removed from analysis. *$p<0.05$, ***$p=0.001$. No significant difference was observed between Lm-gag vaccinated groups with and without chronic Schistosomiasis.

Figure 17A:
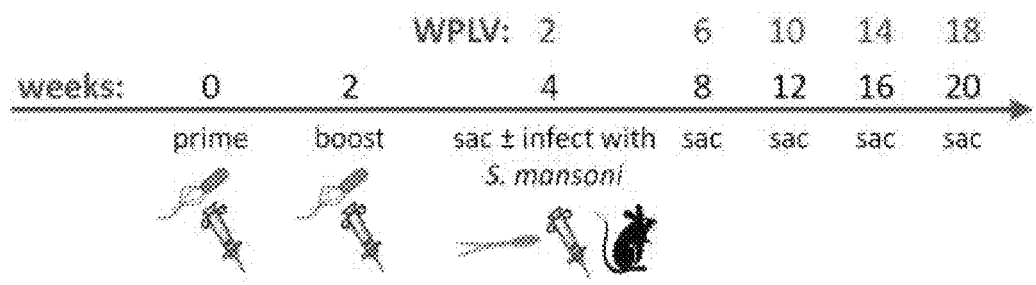
FIGS. 17A-C show that established HIV-1 vaccine responses are altered by subsequent Schistosome infection.
Figure 17B:
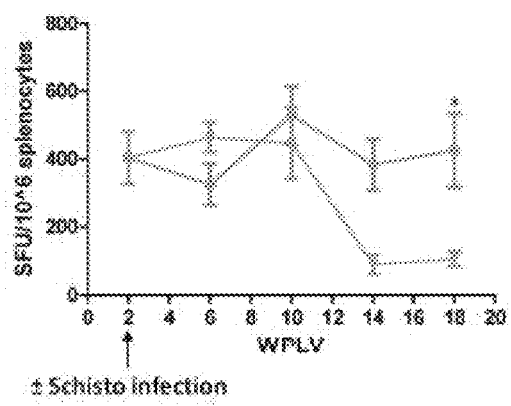
Figure 17C:
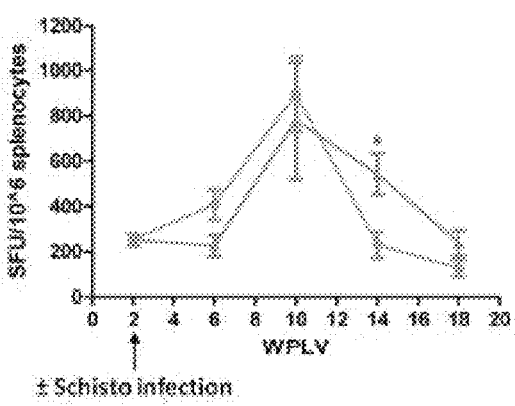

Although responses to helper peptides remain unchanged, vaccination prior to schistosome infection causes CTL responses to diminish as the immune system shifts to a Th2 bias. An outline of the experimental setup is shown (FIG. 17A). Briefly, six to eight week old female Balb/c mice were primed i.p. with 0.2 $LD_{50}$ Listeria-vector HIV-1 vaccine (Lm-gag) or left unvaccinated. Mice were boosted two weeks after the prime in an identical manner. Two wplv, mice were infected by intraperitoneal injection of 50 cercariae of *Schistosoma mansoni* (orange) or left uninfected (green). Mice were sacrificed at various times post schistosome infection and responses to immunodominant CTL (FIG. 17B) and helper (FIG. 17C) epitopes are shown. One very positive outlier was removed from each of 2 time points for uninfected mice on the CTL graph (B). *p<0.05, comparing±Schisto at each time point using t-test analysis.

DETAILED DESCRIPTION OF THE PRESENT INVENTION

In relation to initiation of Th1 and Th2 response, cytokines are regarded as key factors [Paul, W. E. et al., Cell 76 (1994) 241-251], with IL-4 representing the decisive cytokine signal for the differentiation of naive T-helper cells into Th2 cells. The initiation of a Th1 response is on the other hand controlled essentially by IL-12 and IFN-gamma, which are produced by dendritic cells and other accessory cells.

The early production of IL-4 or IL-12 and thus T-cell differentiation are controlled by exogenous and endogenous factors. Among the exogenous factors, the nature of the pathogen is particularly important. A number of pathogens preferentially stimulate a Th1, others a Th2 response [Scott, P. et al., Immunol. Today 12 (1991) 346-348]. It is well known in the art that internal parasites that suppress immune responses, skew the host immune system of human and animals to T-helper type 2 (Th2), and suppress vaccine-specific responses. Further, a failure of the Th1 arm of the immune system and an overactive Th2 arm is implicated in a wide variety of chronic illnesses. These include AIDS, CFS, candidiasis, multiple allergies, multiple chemical sensitivities (MCS), viral hepatitis, gulf war illness, cancer and other illnesses. If these two arms of the immune system could be balanced by stimulating Th1 and decreasing Th2, then many of the symptoms associated with these chronic illnesses would diminish or disappear and we would have found the answer to immune restoration and balance or the equivalent of a cure. Therefore, an object of the invention is to provide methods of driving vaccine-specific immune responses in persistent Th2 profile individuals to enable anti-infectious disease Th1-type and cytotoxic T-cell responses. It is a further object of the invention to provide methods of driving vaccine-specific immune responses in parasitically infected populations to enable anti-HIV, anti-Tuberculosis and anti-malaria immune responses.

In one embodiment, the immune response induced by the methods and compositions provided herein is a therapeutic one. In another embodiment it is a prophylactic immune response. In another embodiment, it is an enhanced immune response over methods available in the art for inducing an immune response in a subject afflicted with the conditions provided herein. In another embodiment, the immune response leads to clearance of the infectious disease afflicting the subject.

It is to be understood that the methods of the present invention may be used to treat any infectious disease, which in one embodiment, is bacterial, viral, microbial, microorganism, pathogenic, or combination thereof, infection. In another embodiment, the methods of the present invention are for inhibiting or suppressing a bacterial, viral, microbial, microorganism, pathogenic, or combination thereof, infection in a subject. In another embodiment, the present invention provides a method of eliciting a cytotoxic T-cell response against a bacterial, viral, microbial, microorganism, pathogenic, or combination thereof, infection in a subject. In another embodiment, the present invention provides a method of inducing a Th1 immune response against a bacterial, viral, microbial, microorganism, pathogenic, or combination thereof, infection in a Th1 unresponsive subject. In one embodiment, the infection is viral, which in one embodiment, is HIV. In one embodiment, the infection is bacterial, which in one embodiment, is mycobacteria, which in one embodiment, is tuberculosis. In one embodiment, the infection is eukaryotic, which in one embodiment, is *plasmodium*, which in one embodiment, is malaria.

In one embodiment, provided herein is a method of inducing a Th1 immune response in a subject having a persistent Th2 phenotypic profile, the method comprising the step of administering to the subject a therapeutically effective dose of a *Listeria* vaccine vector. In another embodiment, the *Listeria* vaccine vector expresses and secretes an antigen fused to an additional immunogenic polypeptide, thereby inducing the Th1 immune response in the subject.

In one embodiment, also provided herein is a method of inducing a Th1 immune response against an infectious disease in a subject having a persistent Th2 phenotypic profile, the method comprising the step of administering to the subject a therapeutically effective dose of a *Listeria* vaccine vector, wherein the *Listeria* vaccine vector expresses and secretes an infectious disease antigen fused to an additional immunogenic polypeptide, thereby inducing a Th1 immune response in the subject.

In one embodiment, provided herein is a method of treating an infectious disease in a subject having a persistent Th2 phenotypic profile, the method comprising the step of administering to the subject a therapeutically effective dose of a *Listeria* vaccine vector, wherein the *Listeria* vaccine vector expresses and secretes an infectious disease antigen fused to an additional immunogenic polypeptide, thereby treating the infectious disease in the subject.

In one embodiment, also provided herein is a method of treating a cancer in a subject having a persistent Th2 phenotypic profile, the method comprising the step of administering to the subject a vaccine comprising a recombinant *Listeria* strain, wherein the vaccine shifts the Th2 phenotype to a Th1 phenotype and allowing for a cell-mediated anti-cancer response to take place.

In another embodiment, the *Listeria* strain expresses and secretes a fusion protein comprising an antigen from the cancer operably linked to an additional immunogenic polypeptide. In another embodiment, the method further makes the cancer amenable to treatment with an additional treatment method. In another embodiment, the additional treatment method is surgery, chemotherapy, radiation, or a combination thereof.

In one embodiment, provided herein is a method of treating, suppressing, or inhibiting at least one tumor or cancer in a subject comprising administering a recombinant *Listeria* strain provided herein to the subject. In another embodiment, the tumor is a prostate tumor, brain tumor, lung tumor, gastrointestinal tumor, pancreatic tumor, an ovarian tumor, breast tumor, or a combination thereof. In another embodiment, the tumor is a cancer, in yet another embodiment, the cancer is a metastatic cancer. In another embodiment, the cancer is a prostate cancer, brain cancer, lung cancer, gastrointestinal cancer, pancreatic cancer, an ovarian cancer, head and neck cancer, glioma, colon cancer, breast cancer, or a combination thereof or any cancer known in the art to generate a Th2 biased immune response in the subject.

In one embodiment, the cancer antigens provided herein can be selected from but are not limited to prostate specific antigen (PSA) and prostate-specific membrane antigen (PSMA), which in one embodiment is FOLH1, HPV-E7, HPV-E6, SCCE, NY-ESO-1, PSMA, prostate stem cell antigen (PSCA), WT-1, HIV-1 Gag, CEA, LMP-1, p53, Proteinase 3, Tyrosinase related protein 2, Muc1 EGFR-III, VEGF-R or any other cancer-associated antigen or any other antigen associated with tumor immune evasion or resistance to cancer. In another embodiment, the antigen is HMW-MAA or a functional fragment thereof. In another embodiment, the cancer antigen is from a cancer known to induce a Th2 profile in a subject having the cancer.

In one embodiment, the cause of a Th2 biased response is a helminth infection, a parasitic infection, an infectious disease, a hormonal therapy, a chronic fatigue syndrome (CFS), an allergic reaction, a gulf-war related illness, multiple chemical sensitivity (MCS), a drug regimen, an autoimmune disease, chemotherapy, or any combination thereof or condition known in the art to cause a Th2 biased immune response in a subject.

In one embodiment, the present invention provides a method of inducing a Th1 immune response in a Th1 unresponsive subject having a concomitant parasitic infection or helminth infection, the method comprising administering a therapeutically effective dose of a *Listeria* vaccine vector provided herein to the subject.

In another embodiment, the present invention provides a method of inducing a Th1 immune response in a Th1 unresponsive subject having concomitant infectious disease and parasitic infections, the method comprising administering to the subject a therapeutically effective dose of a *Listeria* vaccine vector, wherein the *Listeria* vaccine vector expresses and secretes an antigen of the infectious disease.

In another embodiment, the present invention provides a method of inducing a Th1 immune response in a Th1 unresponsive subject having concomitant infectious disease and parasitic infections, the method comprising administering to the subject a therapeutically effective dose of a *Listeria* vaccine vector, wherein the *Listeria* vaccine vector expresses and secretes an antigen of the infectious disease fused to an additional immunogenic polypeptide.

In another embodiment, the present invention provides a method of inducing a Th1 immune response against an infectious disease in a Th1 unresponsive subject having a parasitic infection, the method comprising the step of administering to the parasitic-infected subject a vaccine comprising a recombinant *Listeria* strain that expresses and secretes a fusion protein comprising an infectious disease antigen and an additional immunogenic polypeptide. In another embodiment, the infectious disease is a parasitic infection.

In one embodiment, the infectious disease is one caused by, but not limited to, any one of the following pathogens: *leishmania, Entamoeba histolytica* (which causes amebiasis), *trichuris*, BCG/Tuberculosis, Malaria, *Plasmodium falciparum, plasmodium malariae, plasmodium vivax*, Rotavirus, Cholera, Diptheria-Tetanus, Pertussis, Haemophilus influenzae, Hepatitis B, Human papilloma virus, Influenza (seasonal), Influenza A (H1N1) Pandemic, Measles and Rubella, Mumps, Meningococcus A+C, Oral Polio Vaccines, mono, bi and trivalent, Pneumococcal, Rabies, Tetanus Toxoid, Yellow Fever, *Bacillus anthracis* (anthrax), *Clostridium botulinum* toxin (botulism), *Yersinia pestis* (plague), Variola major (smallpox) and other related pox viruses, *Francisella tularensis* (tularemia), Viral hemorrhagic fevers, Arenaviruses (LCM, Junin virus, Machupo virus, Guanarito virus, Lassa Fever), Bunyaviruses (Hantaviruses, Rift Valley Fever), Flaviruses (Dengue), Filoviruses (Ebola, Marburg), *Burkholderia pseudomallei, Coxiella burnetii* (Q fever), *Brucella* species (brucellosis), *Burkholderia mallei* (glanders), *Chlamydia psittaci* (Psittacosis), Ricin toxin (from *Ricinus communis*), Epsilon toxin of *Clostridium perfringens, Staphylococcus* enterotoxin B, Typhus fever (*Rickettsia prowazekii*), other Rickettsias, Food- and Waterborne Pathogens, Bacteria (Diarrheagenic *E. coli*, Pathogenic Vibrios, *Shigella* species, *Salmonella* BCG/, *Campylobacter jejuni, Yersinia enterocolitica*), Viruses (Caliciviruses, Hepatitis A, West Nile Virus, LaCrosse, California encephalitis, VEE, EEE, WEE, Japanese Encephalitis Virus, Kyasanur Forest Virus, Nipah virus, hantaviruses, Tickborne hemorrhagic fever viruses, Chikungunya virus, Crimean-Congo Hemorrhagic fever virus, Tickborne encephalitis viruses, Hepatitis B virus, Hepatitis C virus, Herpes Simplex virus (HSV), Human immunodeficiency virus (HIV), Human papillomavirus (HPV)), Protozoa (*Cryptosporidium parvum, Cyclospora cayatanensis, Giardia lamblia, Entamoeba histolytica, Toxoplasma*), Fungi (Microsporidia), Yellow fever, Tuberculosis, including drug-resistant TB, Rabies, Prions, Severe acute respiratory syndrome associated coronavirus (SARS-CoV), *Coccidioides posadasii, Coccidioides immitis*, Bacterial vaginosis, *Chlamydia trachomatis*, Cytomegalovirus, Granuloma inguinale, *Hemophilus ducreyi, Neisseria gonorrhea, Treponema pallidum, Trichomonas vaginalis*, or any other infectious disease known in the art that is not listed herein.

In one embodiment, pathogenic protozoans and helminths infections include: amebiasis; malaria; leishmaniasis; trypanosomiasis; toxoplasmosis; *pneumocystis carinii*; babesiosis; giardiasis; trichinosis; filariasis; schistosomiasis; nematodes; trematodes or flukes; and cestode (tapeworm) infections.

In another embodiment, the infectious disease is a livestock infectious disease. In another embodiment, livestock diseases can be transmitted to man and are called "zoonotic diseases." In another embodiment, these diseases include, but are not limited to, Foot and mouth disease, West Nile Virus, rabies, canine parvovirus, feline leukemia virus, equine influenza virus, infectious bovine rhinotracheitis (IBR), pseudorabies, classical swine fever (CSF), IBR, caused by bovine herpesvirus type 1 (BHV-1) infection of cattle, and pseudorabies (Aujeszky's disease) in pigs, toxoplasmosis, anthrax, vesicular stomatitis virus, *rhodococcus equi*, Tularemia, Plague (*Yersinia pestis*), *trichomonas*.

In one embodiment, the present invention provides a method of treating an infectious disease in a Th1 unresponsive subject with a parasitic infection comprising the steps of administering to the parasitic-infected subject a vaccine comprising a recombinant *Listeria* strain that expresses and secretes a fusion protein comprising an infectious disease antigen and an additional immunogenic polypeptide, thereby treating the infectious disease in the Th1 unresponsive subject. In another embodiment, the infectious disease is a parasitic infection.

In one embodiment, a "Th1 unresponsive" or "Th2 persistent" subject is one in which the Th1 immune response is defective, lacking, or repressed a result of a parasitic infection in the subject. In another embodiment the terms refer to a subject wherein a Th2 response is not exclusively present in the subject, but predominates over the Th1 response in the subject. In another embodiment, the terms refer to a subject wherein a Th2 response is exclusively present in the subject and there are no indicators (i.e. cytokines, chemokines or other known markers) of a Th1 response.

In one embodiment, the present invention provides a method of treating an infectious disease in a Th1 unresponsive subject with a parasitic infection comprising the steps of administering to the parasitic-infected subject a vaccine comprising a recombinant *Listeria* strain that expresses and secretes a fusion protein comprising an HIV antigen and an additional immunogenic polypeptide, thereby treating the infectious disease in the Th1 unresponsive subject. In another embodiment, the infectious disease is a parasitic infection.

In one embodiment, the present invention provides a method of treating a Human Immunodeficiency Virus (HIV) infection in a Th1 unresponsive subject with a parasitic infection comprising the steps of administering to the parasitic-infected subject a vaccine comprising a recombinant *Listeria* strain that expresses and secretes a fusion protein comprising an HIV antigen and an additional immunogenic polypeptide, thereby treating the HIV infection in the Th1 unresponsive subject.

In one embodiment, the present invention provides a method of suppressing an infectious disease in a Th1 unresponsive subject with a parasitic infection comprising the steps of administering to the parasitic-infected subject a vaccine comprising a recombinant *Listeria* strain that expresses and secretes a fusion protein comprising an infectious disease antigen and an additional immunogenic polypeptide, thereby suppressing the infectious disease in the Th1 unresponsive subject. In another embodiment, the infectious disease is a parasitic infection.

In another embodiment, the present invention provides a method of suppressing a Human Immunodeficiency Virus (HIV) infection in a subject with a parasitic infection comprising the step of administering to the parasitic-infected subject a vaccine comprising a recombinant *Listeria* strain that expresses and secretes a fusion protein comprising an HIV antigen and an additional immunogenic polypeptide, thereby suppressing the HIV infection in the subject.

In one embodiment, the present invention provides a method of inhibiting an infectious disease in a Th1 unresponsive subject with a parasitic infection comprising the steps of administering to the parasitic-infected subject a vaccine comprising a recombinant *Listeria* strain that expresses and secretes a fusion protein comprising an infectious disease antigen and an additional immunogenic polypeptide, thereby inhibiting the infectious disease in the Th1 unresponsive subject. In another embodiment, the infectious disease is a parasitic infection.

In another embodiment, the present invention provides a method of inhibiting a Human Immunodeficiency Virus (HIV) infection in a subject with a parasitic infection comprising the step of administering to the parasitic-infected subject a vaccine comprising a recombinant *Listeria* strain that expresses and secretes a fusion protein comprising an HIV antigen and an additional immunogenic polypeptide, thereby inhibiting the HIV infection in the subject.

In one embodiment, the present invention provides a method of eliciting a cytotoxic T-cell response to an infectious disease in a Th1 unresponsive subject with a parasitic infection comprising the steps of administering to the parasitic-infected subject a vaccine comprising a recombinant *Listeria* strain that expresses and secretes a fusion protein comprising an infectious disease antigen and an additional immunogenic polypeptide, thereby inhibiting the infectious disease in the Th1 unresponsive subject. In another embodiment, the infectious disease is a parasitic infection.

In another embodiment, the present invention provides a method of eliciting a cytotoxic T-cell response to a Human Immunodeficiency Virus (HIV) infection in a subject with a parasitic infection comprising the step of administering to the parasitic-infected subject a vaccine comprising a recombinant *Listeria* strain that expresses and secretes a fusion protein comprising an HIV antigen and an additional immunogenic polypeptide, thereby eliciting the cytotoxic T-cell response in the subject.

In one embodiment, the present invention provides a method of treating a viral infection in a Th1 unresponsive subject with a parasitic infection comprising the step of administering to the parasitic-infected subject a vaccine comprising a recombinant *Listeria* strain that expresses and secretes a fusion protein comprising an viral antigen and an additional immunogenic polypeptide, thereby treating the viral infection in the Th1 unresponsive subject.

In another embodiment, the present invention provides a method of suppressing a viral infection in a Th1 unresponsive subject with a parasitic infection comprising the step of administering to the parasitic-infected subject a vaccine comprising a recombinant *Listeria* strain that expresses and secretes a fusion protein comprising a viral antigen and an additional immunogenic polypeptide, thereby suppressing the viral infection in the Th1 unresponsive subject.

In another embodiment, the present invention provides a method of inhibiting a viral infection in a subject with a parasitic infection comprising the step of administering to the parasitic-infected subject a vaccine comprising a recombinant *Listeria* strain that expresses and secretes a fusion protein comprising an HIV antigen and an additional immunogenic polypeptide, thereby inhibiting the viral infection in the subject.

In another embodiment, the present invention provides a method of eliciting a cytotoxic T-cell response to a viral infection in a Th1 unresponsive subject with a parasitic infection comprising the step of administering to the parasitic-infected subject a vaccine comprising a recombinant *Listeria* strain that expresses and secretes a fusion protein comprising a viral antigen and an additional immunogenic polypeptide, thereby eliciting the cytotoxic T-cell response in the Th1 unresponsive subject.

In one embodiment, the present invention provides a method of treating a malaria infection in a Th1 unresponsive subject with an additional parasitic infection comprising the step of administering to the parasitic-infected subject a vaccine comprising a recombinant *Listeria* strain that expresses and secretes a fusion protein comprising a malaria antigen and an additional immunogenic polypeptide, thereby treating the malaria infection in the Th1 unresponsive subject.

In another embodiment, the present invention provides a method of suppressing a malaria infection in a Th1 unresponsive subject with an additional parasitic infection comprising the step of administering to the parasitic-infected subject a vaccine comprising a recombinant *Listeria* strain that expresses and secretes a fusion protein comprising a malaria antigen and an additional immunogenic polypeptide, thereby suppressing the malaria infection in the Th1 unresponsive subject.

In another embodiment, the present invention provides a method of inhibiting a malaria infection in a Th1 unresponsive subject with an additional parasitic infection comprising the step of administering to the parasitic-infected subject a vaccine comprising a recombinant *Listeria* strain that expresses and secretes a fusion protein comprising a malaria antigen and an additional immunogenic polypeptide, thereby inhibiting the malaria infection in the Th1 unresponsive subject.

In another embodiment, the present invention provides a method of eliciting a cytotoxic T-cell response to a malaria infection in a Th1 unresponsive subject with an additional parasitic infection comprising the step of administering to the parasitic-infected subject a vaccine comprising a recombinant *Listeria* strain that expresses and secretes a fusion protein comprising a malaria antigen and an additional immunogenic polypeptide, thereby eliciting the cytotoxic T-cell response in the Th1 unresponsive subject.

In one embodiment, administering the recombinant *Listeria* in the Th1 unresponsive subject with the parasitic infection enables the generation of a memory immune response. In another embodiment, the response is a memory T-cell response. In another embodiment, the response is a memory B-cell response.

In one embodiment, the present invention provides a method of treating a tuberculosis infection in a Th1 unresponsive subject with a parasitic infection comprising the step of administering to the parasitic-infected subject a vaccine comprising a recombinant *Listeria* strain that expresses and secretes a fusion protein comprising a tuberculosis antigen and an additional immunogenic polypeptide, thereby treating said tuberculosis infection in said Th1 unresponsive subject.

In another embodiment, the present invention provides a method of suppressing a tuberculosis infection in a Th1 unresponsive subject with a parasitic infection comprising the step of administering to the parasitic-infected subject a vaccine comprising a recombinant *Listeria* strain that expresses and secretes a fusion protein comprising a tuberculosis antigen and an additional immunogenic polypeptide, thereby suppressing said tuberculosis infection in the Th1 unresponsive subject.

In another embodiment, the present invention provides a method of inhibiting a tuberculosis infection in a Th1 unresponsive subject with a parasitic infection comprising the step of administering to the parasitic-infected subject a vaccine comprising a recombinant *Listeria* strain that expresses and secretes a fusion protein comprising a tuberculosis antigen and an additional immunogenic polypeptide, thereby inhibiting said tuberculosis infection in the Th1 unresponsive subject.

In another embodiment, the present invention provides a method of eliciting a cytotoxic T-cell response to a tuberculosis infection in a Th1 unresponsive subject with a parasitic infection comprising the step of administering to the parasitic-infected subject a vaccine comprising a recombinant *Listeria* strain that expresses and secretes a fusion protein comprising a tuberculosis antigen and an additional immunogenic polypeptide, thereby eliciting said cytotoxic T-cell response in the Th1 unresponsive subject.

In one embodiment, a vaccine or immunogenic composition of the present invention is administered alone to a subject. In another embodiment, the vaccine or immunogenic composition is administered together with another anti-parasitic therapy. Each possibility represents a separate embodiment of the present invention.

In another embodiment, methods of administering the vaccine are well known in the art and include, but are not limited to, oral administration, parenteral administration, intravenous (IV) administration, intranasal administration, or intraperitoneal (IP) administration.

In another embodiment, the additional immunogenic polypeptide is a Listeriolysin O (LLO) polypeptide, an ActA polypeptide, or a PEST sequence. In yet another embodiment, the LLO polypeptide comprises a signal sequence from a wild-type listerial protein.

In another embodiment, the recombinant *Listeria* strain is a *Listeria monocytogenes* strain.

In one embodiment, the methods of the present invention are for treating an HIV or other microbial infection. In another embodiment, the other microbial infection is tuberculosis. In another embodiment, it is malaria. In another embodiment it is hepatitis A, B or C, in another embodiment, it is influenza.

In one embodiment, the terms "treating", "therapeutic", "therapy" are used interchangeably herein and refer to therapeutic treatment, while "inhibiting" and "suppressing" refer to prophylactic or preventative measures, wherein the object is to prevent or lessen the targeted pathologic condition or disorder as described hereinabove. Thus, in one embodiment, treating may include directly affecting or curing the disease, disorder or condition and/or related symptoms, while suppressing or inhibiting may include preventing, reducing the severity of, delaying the onset of, reducing symptoms associated with the disease, disorder or condition, or a combination thereof. Thus, in one embodiment, "treating" refers inter alia to delaying progression, expediting remission, inducing remission, augmenting remission, speeding recovery, increasing efficacy of or decreasing resistance to alternative therapeutics, or a combination thereof. In one embodiment, "prophylaxis," "prophylactic," "preventing" or "inhibiting" refers, inter alia, to delaying the onset of symptoms, preventing relapse to a disease, decreasing the number or frequency of relapse episodes, increasing latency between symptomatic episodes, or a combination thereof. In one embodiment, "suppressing" refers inter alia to reducing the severity of symptoms, reducing the severity of an acute episode, reducing the number of symptoms, reducing the incidence of disease-related symptoms, reducing the latency of symptoms, ameliorating symptoms, reducing secondary symptoms, reducing secondary infections, prolonging patient survival, or a combination thereof.

In one embodiment, symptoms are primary, while in another embodiment, symptoms are secondary. In one embodiment, "primary" refers to a symptom that is a direct result of the subject viral infection, while in one embodiment, "secondary" refers to a symptom that is derived from or consequent to a primary cause. In one embodiment, the compositions and strains for use in the present invention treat primary or secondary symptoms or secondary complications related to HIV or other microbial infection.

In another embodiment, "symptoms" may be any manifestation of a disease or pathological condition, comprising inflammation, swelling, sputum, fever, pain, bleeding, itching, runny nose, coughing, headache, migraine, difficulty breathing, weakness, fatigue, drowsiness, weight loss, nausea, vomiting, constipation, diarrhea, numbness, dizziness, blurry vision, muscle twitches, convulsions, etc., or a combination thereof.

In another embodiment, the disease, disorder, or symptom is fever. In another embodiment, the disease, disorder, or symptom is headache. In another embodiment, the disease, disorder, or symptom is stiff neck. In another embodiment, the disease, disorder, or symptom is seizures. In another embodiment, the disease, disorder, or symptom is partial paralysis. In another embodiment, the disease, disorder, or symptom is stupor. In another embodiment, the disease, disorder, or symptom is coma. In another embodiment, the disease, disorder, or symptom is any other disease, disorder, or symptom known in the art that is associated with or is secondary to a pathogen-mediated encephalitis.

HIV induces a persistent and progressive infection leading, in the vast majority of cases, to the development of the acquired immunodeficiency syndrome ("AIDS"). There are at least two distinct types of HIV: HIV-1 and HIV-2. HIV infection leads to immune incompetence, opportunistic infections, neurological dysfunctions, neoplastic growth, and ultimately death. The HIV RNA genome consists of at least seven structural landmarks (LTR, TAR, RRE, PE, SLIP, CRS, and INS) and nine genes (gag, pol, and env, tat, rev, nef, vif vpr, vpu, and sometimes a tenth tev, which is a fusion of tat env and rev) encoding 19 proteins. Three of these genes, gag, pol, and env, contain information needed to make the structural proteins for new virus particles. For example, env codes for a protein called gp160 that is broken down by a viral enzyme to form gp120 and gp41. The six remaining genes, tat, rev, nef, vif, vpr, and vpu (or vpx in the case of HIV-2), are regulatory genes for proteins that control the ability of HIV to infect cells, produce new copies of virus (replicate), or cause disease. The two Tat proteins (p16 and p14) are transcriptional transactivators for the LTR promoter acting by binding the TAR RNA element. The TAR may also be processed into microRNAs that regulate the apoptosis genes ERCC1 and IER3. The Rev protein (p19) is involved in shuttling RNAs from the nucleus and the cytoplasm by binding to the RRE RNA element. The Vif protein (p23) prevents the action of APOBEC3G (a cell protein that deaminates DNA:RNA hybrids and/or interferes with the Pol protein). The Vpr protein (p14) arrests cell division at G2/M. The Nef protein (p27) down-regulates CD4 (the major viral receptor), as well as the MHC class I and class II molecules.

Nef also interacts with SH3 domains. The Vpu protein (p16) influences the release of new virus particles from infected cells. The ends of each strand of HIV RNA contain an RNA sequence called the long terminal repeat (LTR). Regions in the LTR act as switches to control production of new viruses and can be triggered by proteins from either HIV or the host cell. The Psi element is involved in viral genome packaging and recognized by Gag and Rev proteins. The SLIP element (TTTTTT) is involved in the frameshift in the Gag-Pol reading frame required to make functional Pol. http://en.wikipedia.org/wiki/HIV—cite_note-compendia-50

HIV uses a receptor-mediated pathway in the infection of host cells. HIV requires contact with two cell-surface receptors to gain entry into cells and initiate infection; CD4 is the primary receptor. CXCR4 ("X4") and CCR5 ("R5"), members of the chemokine receptor family of proteins, serve as secondary co-receptors for HIV isolates that have historically been called tropic for T cell lines or macrophages, respectively. CXCR4 or CCR5, in conjunction with CD4, form a functional cellular receptor for entry of certain strains of HIV into cells.

The HIV antigen-encoding DNA for insertion into these vectors are any that are known to be effective antigens for protection against a retrovirus. These can include both structural and non-structural proteins. The envelope, polymerase, gag, and protease are preferred proteins or sources of epitopes, but other proteins or epitopes can also be employed including those proteins encoded by non-structural genes, e.g., rev, tat, nef, vif, and vpr. For HIV, nucleic acids that can be inserted into the viral vector includes, but are not limited to, nucleic acid that can code for at least one of: HIV1gag(+pro)(IIIB), gp120(MN)(+transmembrane), nef(BRU)CTL, pol(IIIB)CTL, ELDKWA or LDKW epitopes, preferably HIV1gag(+pro)(IIIB), gp120(MN) (+transmembrane), two (2) nef(BRU)CTL and three pol (IIIB)CTL epitopes; or two ELDKWA in gp120 V3 or another region or in gp160. The two nef(BRU)CTL and three pol(IIIB) CTL epitopes are preferably CTL1, CTL2, pol1, pol2 and pol3. In the above listing, the viral strains from which the antigens are derived are noted parenthetically. HIV and its antigens, including HIV-gag are well known in the art (see for e.g. U.S. Pat. Nos. 7,790,177 and 7,786,288 incorporated herein in its entirety by reference). HIV-gag antigens contemplated for use in the methods provided herein include those known in the art that can be searched for in Genbank and similar databases, and include but are not limited to for example, accession No. ADG95996, CBI61237, CBI61236, CBI61235, CBI61234, CBI61233, CBI61232, CBI61231, CBI61230, CBI61229, CBI61228, CBI61227, CBI61226, CBI61225, CBI61224, CBI61223, CBI61222, CBI61221, CBI61220, CBI61219, CBI61218, CBI61217, CBI61216, CBI61215, CBI61214, CBI61213, CBI61212, CBI61211, CBI61210, CBI61209, CBI61208, CBI61207, CBI61206, CBI61205, CBI61204, CBI61203, CBI61202, CBI61201, CBI61200, CBI61199, CBI61198, CBI61197, CBI61196, CBI61195, CBI61194, CBI61193, CBI61192, CBI61191, CBI61190, CBI61189, CBI61188, CBI61187, CBI61186, CBI61185, CBI61184, CBI61183, CBI61182. HIV-pol antigens contemplated for use in the methods provided herein include those known in the art that can be searched for in Genbank and similar databases, and include but are not limited to for example, accession No. AAF35355, BAF32553, BAF32544, BAF32535.1, BAF32526, BAF32517, BAF32508, BAF32499, BAF32490, BAF32481, BAF32472, BAF32463, BAF32454, BAF32445, BAF32436, BAF32427, BAF32418, BAF32409, BAF32400, BAF32391, BAF32382, BAF32373, BAF32364, BAF32355, BAF32346, BAF32337, BAF32328, BAF32319, BAF32310, BAF32301. HIV-env antigens contemplated for use in the methods provided herein include those known in the art that can be searched for in Genbank and similar databases, and include but are not limited to for example, accession No. AAB09538, CAA00873, AAF35356, AAD42280, AAD42279, AAD42278, AAD42277, AAD42276, AAD42275, AAD42274, AAD42273, AAD42272, AAD42271, AAD42270, AAD42269, AAD42268, AAD42267, AAD42266, AAD42265, AAD42264, AAD42263, AAD42262, AAD42261, AAD42260, AAA53206, BAF32559, BAF32550, BAF32541, BAF32532, BAF32523.

Methods of determining the presence of an HIV infection are well known in the art and include, inter alia, detection of HIV antibodies, antigens, or nucleic acids in serum, saliva, urine, or a combination thereof. Methods of determining the severity of an HIV infection are well known in the art and include, inter alia, measurement of viral load or CD4 decline. Each method represents a separate embodiment of the present invention.

In one embodiment, the methods of the present invention comprise treating secondary complications of HIV infection. In another embodiment, the methods comprise treating opportunistic infections, neoplasms, neurologic abnormalities, or progressive immunologic deterioration. In another embodiment, the methods comprise treating acquired immunodeficiency syndrome (AIDS). In another embodiment, the methods comprise treating a decline in the number of CD4+ T lymphocytes.

In another embodiment, methods comprise treating HIV transmitted by direct sexual contact, either homosexual or heterosexual; by blood or blood products; or from an infected mother to infant, either intrapartum, perinatally, or via breast milk.

In one embodiment, the methods of the present invention may be used to treat HIV or related infections that were acquired via zoonotic transmission. In one embodiment, methods of treating infection comprise treating Clade A, B, C, D, A/E, F, G, H, J, or K. In another embodiment, the infection is mediated by HIV-1, while in another embodiment, it's mediated by HIV-2. In one embodiment, it's mediated by the M group of HIV-1, in another embodiment, it's mediated by the O group of HIV-1, while in another embodiment, it's mediated by the N group of HIV-1. In one embodiment, it's mediated by the A Glade (or subtype) of the M group of HIV-1, in another embodiment, it's mediated by the B Glade of the M group of HIV-1, in another embodiment, it's mediated by the C Glade of the M group of HIV-1, in another embodiment, it's mediated by the D Glade of the M group of HIV-1, in another embodiment, it's mediated by the A/E Glade of the M group of HIV-1, in another embodiment, it's mediated by the F Glade of the M group of HIV-1, in another embodiment, it's mediated by the G Glade of the M group of HIV-1, in another embodiment, it's mediated by the H Glade of the M group of HIV-1, in another embodiment, it's mediated by the J Glade of the M group of HIV-1, in another embodiment, it's mediated by the K Glade of the M group of HIV-1, in another embodiment, it's mediated by the A/G/I Glade of the M group of HIV-1, while in another embodiment, it's mediated by a circulating recombinant form (CRF) of any of the above clades. The classification of HIV strains into subtypes and CRFs is a complex issue and the definitions are subject to change as new discoveries are made. Hence the present invention encompasses any HIV subtype discovered or known in the art.

In one embodiment, methods of treating infection comprise treating a macrophage-tropic strain of HIV, T cell-tropic strain of HIV, or any combination thereof. In one embodiment, the methods of the present invention will treat infection mediated by a macrophage-tropic strain of HIV. In another embodiment, the compounds will treat infection mediated by a T cell-tropic strain of HIV. In another embodiment, the compounds will treat infection mediated by either a macrophage-tropic strain of HIV, a T cell-tropic, or both. In another embodiment, the mechanism of action of the methods of the present invention differ based on the tropism of HIV.

In one embodiment, the methods of the present invention may be used to treat, inhibit or suppress HIV in subjects who have been diagnosed with HIV. In another embodiment, the methods of the present invention may be used to treat, inhibit or suppress HIV in subjects who have not been diagnosed with HIV. In another embodiment, the methods of the present invention may be used to treat, inhibit or suppress HIV in subjects who have been exposed to HIV. In another embodiment, the methods of the present invention may be used to treat, inhibit or suppress HIV in subjects in the window period, which in one embodiment, is the period between exposure to HIV and the production of an immune response sufficient to detect HIV antibodies using standard HIV tests.

In one embodiment, the methods of the present invention for treating an HIV infection may be used with other methods of treating an HIV infection known in the art and may increase the efficacy of the other methods of treatment. In one embodiment, a method of treating an HIV infection is administration of an antiretroviral drug or a combination of antiretroviral drugs.

In one embodiment, the current method of treating, inhibiting or suppressing HIV is highly active antiretroviral therapy (HAART), which in one embodiment is a combination (or "cocktail") consisting of at least three drugs belonging to at least two types, or "classes," of antiretroviral agents. In one embodiment, a current method of treating, inhibiting or suppressing HIV is administering a nucleoside analogue reverse transcriptase inhibitor (NARTI or NRTI), a protease inhibitor, a non-nucleoside reverse transcriptase inhibitor (NNRTI), or a combination thereof. In another embodiment, a current method of treating, inhibiting or suppressing HIV is administering an entry inhibitor. In another embodiment, a current method of treating, inhibiting or suppressing HIV is administering an HIV vaccine.

In one embodiment, the infectious disease is leshmaniasis, and is caused by parasites of the genus *Leishmania* and is endemic in many parts of Africa, Asia and South America. It is transmitted by the sand fly or the *Phlebotimus* species. Leishmaniasis causes 3 types of disease i.e. visceral leishmaniasis (caused by *L.d.donovani, L.d.infantum, L.d chagasi*), cutaneous leishmaniasis (caused by *L. tropica, L. major, L. aethiopica, L. Mexicana*), and muco-cutaneous leishmaniasis (*L. braziliensis* complex). Several antigens *Leishmania* antigens are used to diagnose the infection and these include, but are not limited to *Leishmania* antigens (rH2A, KMP11, and the "Q" protein). Methods for diagnosis Leishmaniasis include those methods described in the art, for example in Eur J Clin Microbiol Infect Dis. 2004 December; 23 (12):899-904, and in Clinical and Diagnostic Laboratory Immunology, October 2005, p. 1164-1167, Vol. 12, No. 10, each of which are incorporated herein in their entirety.

In one embodiment, the infectious disease is Amebiasis. Amebiasis is caused by *Entamoeba histolytica*, a protozoan found worldwide. The highest prevalence of amebiasis is in developing countries where barriers between human feces and food and water supplies are inadequate. *E. histolytica* is transmitted via ingestion of the cystic form (infective stage) of the protozoa. Viable in the environment for weeks to months, cysts can be found in fecally contaminated soil, fertilizer, or water or on the contaminated hands of food handlers. Fecal-oral transmission can also occur in the setting of anal sexual practices or direct rectal inoculation through colonic irrigation devices. Excystation then occurs in the terminal ileum or colon, resulting in trophozoites (invasive form). The trophozoites can penetrate and invade the colonic mucosal barrier, leading to tissue destruction, secretory bloody diarrhea, and colitis resembling inflammatory bowel disease. In addition, the trophozoites can spread hematogenously via the portal circulation to the liver or even to more distant organs. Methods of diagnosis amebiasis include, microscopy, In vitro culture and isoenzyme analysis, antigen detection on stool samples, serology (such as detection of Gal/GalNAc lectin antigen in serum), molecular diagnoses using PCR, amebic liver abscess, further colonoscopy or sigmoidoscopy may be used for the diagnosis of amoebic colitis.

In one embodiment, the infectious disease or parasitic infection is Trichuriasis. Trichuriasis is caused by *Trichuris trichiura* or *Trichocephalus trichiuris*, which is a roundworm that causes trichuriasis when it infects a human large intestine. Trichuriasis is transmitted by the fecal-oral route, and larvae hatch in the small intestine, where they grow and molt, finally taking up residence in the large intestine. The disease can be diagnosed by detecting eggs in stool examination. Eggs will appear barrel-shaped, unembryonated, having bipolar plugs and a smooth shell. Rectal prolapse can be diagnosed easily using a defecating proctogram and is one of many methods for imaging the parasitic infection. Further, sigmoidoscopy shows characteristic white bodies of adult hanging from inflamed mucosa (coconut cake rectum).

In one embodiment, the parasitic infection or the infectious disease is *Plasmodium falciparum, Plasmodium vivax, Plasmodium ovale curtisi, Plasmodium ovale wallikeri, Plasmodium malariae, Plasmodium knowlesi, Plasmodium brasilianum, Plasmodium cynomolgi, Plasmodium cynomolgi bastianellii, Plasmodium inui, Plasmodium rhodiani, Plasmodium schwetzi, Plasmodium semiovale, Plasmodium simium*. In one embodiment, the parasitic infection is any *plasmodium* known to infect humans.

In one embodiment, the methods of the present invention may be used to treat, inhibit or suppress malaria in subjects who have been diagnosed with malaria. In another embodiment, the methods of the present invention may be used to treat, inhibit or suppress malaria in subjects who have not been diagnosed with malaria. In another embodiment, the methods of the present invention may be used to treat, inhibit or suppress malaria in subjects who have been exposed to malaria. In another embodiment, the methods of the present invention may be used to treat, inhibit or suppress malaria in subjects in the window period, which in one embodiment is the period between exposure to malaria and the production of an immune response sufficient to detect malaria antibodies using standard malaria tests.

In one embodiment, symptoms of malaria are: fever and shivering; a poor general condition, feeling unwell and having headaches like influenza infection, diarrhea, nausea and vomiting, fatigue, or a combination thereof. In another embodiment, symptoms of malaria are: increased drowsiness, leading to coma and associated failure of all the major organ systems low blood pressure (hypotension), kidney failure, possible haemorrhage (bleeding), effects on the liver (e.g. infectious jaundice), shock, coma or a combination thereof. In one embodiment, malaria is cerebral malaria. In one embodiment, malaria is Blackwater fever.

In one embodiment, malaria is diagnosed by symptomatic diagnosis, Microscopic examination of blood films, Antigen tests (which in one embodiment is *P. falciparum* glutamate dehydrogenase or *P. falciparum* lactate dehydrogenase), or PCR-based assays such as QT-NASBA. In one embodiment, malaria is diagnosed in subjects with an additional parasitic infection prior to or, in another embodiment, as a first step in, the methods of the present invention.

In one embodiment, the vaccine for use in the methods of the present invention are used along with known malaria treatments or preventative compositions, which in one embodiment, include administration of mefloquine (in one embodiment, Lariam), doxycycline, the combination of atovaquone and proguanil hydrochloride (in one embodiment, Malarone), or a combination thereof. In another embodiment, malaria treatment/prevention may include administration of quinine, quinacrine, chloroquine, primaquine, or a combination thereof.

In one embodiment, the recombinant *Listeria monocytogenes* used in the methods of the present invention comprises a malaria antigen, which in one embodiment, is any malaria antigen known in the art. In one embodiment, the malaria antigen is *Plasmodium falciparum* circumsporozoite protein (CSP) CSP and sporozoite surface protein 2 (called PfSSP; liver stage antigen 1 (LSA1), merozoite surface protein 1 (MSP-1), serine repeat antigen and AMA-1; Pfs25; schizont export protein; 19 repeats of the sporozoite surface protein [NANP]; CSP covalently bound to an immunogenic peptide, in one embodiment, purified *Pseudomonas aeruginosa* toxin or to another antigen, in one embodiment, surface antigen from Hepatitis B, or a combination thereof. In another embodiment, the malaria antigen is one or more of the antigens from the following vaccine: SPf66; recombinant (Asn-Ala-Pro15Asn-Val-Asp-Pro)2-Leu-Arg(R32LR) protein covalently bound to a purified *Pseudomonas aeruginosa* toxin; NYVAC-Pf7; [NANP]19-5.1; RTS,S, RTS,S/AS01; or a combination thereof.

In one embodiment, the infection is a bacterial infection, which in another embodiment is mycobacteria, which in one embodiment, is tuberculosis.

In one embodiment, the methods of the present invention may be used to treat, inhibit or suppress tuberculosis in subjects who have been diagnosed with tuberculosis. In another embodiment, the methods of the present invention may be used to treat, inhibit or suppress tuberculosis in subjects who have not been diagnosed with tuberculosis. In another embodiment, the methods of the present invention may be used to treat, inhibit or suppress tuberculosis in subjects who have been exposed to tuberculosis. In another embodiment, the methods of the present invention may be used to treat, inhibit or suppress tuberculosis in subjects in the window period, which in one embodiment, is the period between exposure to tuberculosis and the production of an immune response sufficient to detect tuberculosis antibodies using standard tuberculosis tests.

In one embodiment, the methods of the present invention are used in conjunction with methods of determining tuberculosis infection or after a tuberculosis diagnosis has been made. In one embodiment, tuberculosis diagnosis is from identifying the causative organism (*Mycobacterium tuberculosis*) in a clinical sample (for example, sputum or pus). In one embodiment, tuberculosis diagnosis is made using imaging (X-rays or scans); a tuberculin skin test (in one embodiment, a Mantoux test); PCR assays for the detection of bacterial DNA, interferon release assays (IGRAs) (in one embodiment, ESAT-6-responsive, or antigens 85a or 85b responsive) or a combination thereof.

In one embodiment, an attenuated live bovine tuberculosis *bacillus* is used together with the vaccine for use in the present invention. In another embodiment, *Bacillus* Calmette-Guérin (BCG) vaccine is used together with the vaccine for use in the present invention.

In one embodiment, the most commonly used diagnostic tool for tuberculosis (TB) is a simple skin test.

In another embodiment, another tuberculosis diagnostic tool is the Mantoux test, in which a small amount of a substance called PPD tuberculin is injected just below the skin of the subject's forearm. Within 48 to 72 hours, a health care professional checks the subject's arm for swelling at the injection site, indicating a reaction to the injected material. In one embodiment, a hard, raised red bump (induration) means the subject is ready to have TB infection. The size of the bump determines whether the test results are significant, based on the subject's risk factors for TB.

However, the Mantoux test isn't perfect as false-positive test suggests that a subject has TB when it is not the case. This is most likely to occur if the subject is infected with a different type of *mycobacterium* other than the one that causes tuberculosis, or if the subject has recently been vaccinated with the *bacillus* Calmette-Guerin (BCG) vaccine. This TB vaccine is seldom used in the United States, but widely used in countries with high TB infection rates. On the other hand, some people who are infected with TB—including children, older people and people with AIDS—may have a delayed or no response to the Mantoux test.

Blood tests may be used to confirm or rule out latent or active TB. These tests use sophisticated technology to measure the immune system's reaction to *Mycobacterium tuberculosis*. These tests are quicker and more accurate than is the traditional skin test. They may be useful if you're at high risk of TB infection but have a negative response to the Mantoux test, or if you received the BCG vaccine.

Having little or no reaction to the Mantoux test can mean that a subject is not infected with TB bacteria. But in some cases it's possible to have TB infection in spite of a negative test. In one embodiment, one reason for a false-negative test include recent TB infection as it can take eight to 10 weeks after a subject has been infected for the subject's body to react to a skin test. Hence a subject may need to repeat the test in a few months.

In another embodiment, another reason for false-negative is if a subject is immuno-compromised by an illness, such as AIDS, or by corticosteroid or chemotherapy drugs, given that the subject may not respond to the Mantoux test, even though you're infected with TB.

In another embodiment, another reason for false-negative results include vaccination with a live virus given that vaccines that contain a live virus, such as the measles or smallpox vaccine, can interfere with a TB skin test.

In yet another embodiment, another reason for false-negative results includes overwhelming TB disease. If the subject's body has been overwhelmed with TB bacteria, it may not be able to mount enough of a defense to respond to the skin test.

In one embodiment, another reason for false-negative results includes improper testing. Sometimes the PPD tuberculin may be injected too deeply below the surface of the subject's skin. In that case, any reaction the subject has may not be visible.

In one embodiment, if the results of a TB test are positive (referred to as "significant"), a subject may have further tests to help determine whether the subject has active TB disease and whether it is a drug-resistant strain. These tests may include chest X-ray or CT scan. In some cases, this may show white spots in your lungs where your immune system has walled off TB bacteria. In others, it may reveal a nodule or cavities in your lungs caused by active TB. In one embodiment, a computerized tomography (CT) scan, which uses cross-sectional X-ray images, may show more subtle signs of disease.

If the subject's chest X-ray shows signs of TB, the clinician may take a sample of the subject's stomach secretions or sputum. The samples are tested for TB bacteria, and the clinician can have the results of special smears in a matter of hours.

Samples may also be sent to a laboratory where they're examined under a microscope as well as placed on a special medium that encourages the growth of bacteria (culture). The bacteria that appear are then tested to see if they respond to the medications commonly used to treat TB. Because TB bacteria grow very slowly, traditional culture tests can take four to eight weeks.

In one embodiment, another test used to diagnose TB infection include the nuclear acid amplification (NAA) test. This test can detect genes associated with drug resistance in *Mycobacterium tuberculosis*. However, this test is generally available only in developed countries.

In one embodiment, a test used primarily in developing countries is called the microscopic-observation drug-susceptibility (MODS) assay. It can detect the presence of TB bacteria in sputum in as little as seven days. Additionally, the test can identify drug-resistant strains of the TB bacteria.

It is more difficult to diagnose TB in children than in adults as children may swallow sputum, rather than coughing it out, making it harder to take culture samples. And infants and young children may not react to the skin test. For these reasons, tests from an adult who is likely to have been the cause of the infection may be used to help diagnose TB in a child.

In one embodiment, *M. tuberculosis* antigens, and DNA sequences encoding such antigens, may be prepared using any of a variety of procedures. For example, soluble antigens may be isolated from *M. tuberculosis* culture filtrate by procedures known to those of ordinary skill in the art, including anion-exchange and reverse phase chromatography. Purified antigens may then be evaluated for a desired property, such as the ability to react with sera obtained from an *M. tuberculosis*-infected individual. Such screens may be performed using the representative methods described herein. Antigens may then be partially sequenced using, for example, traditional Edman chemistry. See Edman and Berg, *Eur. J. Biochem.* 80:116-132, 1967.

Antigens may also be produced recombinantly using a DNA sequence that encodes the antigen, which has been inserted into an expression vector and expressed in an appropriate host. DNA molecules encoding soluble antigens may be isolated by screening an appropriate *M. tuberculosis* expression library with anti-sera (e.g., rabbit) raised specifically against soluble *M. tuberculosis* antigens. DNA sequences encoding antigens that may or may not be soluble may be identified by screening an appropriate *M. tuberculosis* genomic or cDNA expression library with sera obtained from patients infected with *M. tuberculosis*. Such screens may generally be performed using techniques well known in the art, such as those described in Sambrook et al., *Molecular Cloning: A Laboratory Manual*, Cold Spring Harbor Laboratories, Cold Spring Harbor, N.Y., 1989.

DNA sequences encoding soluble antigens may also be obtained by screening an appropriate *M. tuberculosis* cDNA or genomic DNA library for DNA sequences that hybridize to degenerate oligonucleotides derived from partial amino acid sequences of isolated soluble antigens. Degenerate oligonucleotide sequences for use in such a screen may be designed and synthesized, and the screen may be performed, as described (for example) in Sambrook et al., *Molecular Cloning: A Laboratory Manual*, Cold Spring Harbor Laboratories, Cold Spring Harbor, N.Y. (and references cited therein). Polymerase chain reaction (PCR) may also be employed, using the above oligonucleotides in methods well known in the art, to isolate a nucleic acid probe from a cDNA or genomic library. The library screen may then be performed using the isolated probe.

In one embodiment *M. tuberculosis* antigens include any know in the art, for example, but not limited to, ESAT-6, TB10.4, CFP10, RD1-ORF5, RD1-ORF2, Rv1036, MPB64, MPT64, Ag85A, Ag85B (MPT59), Mtb39, MPB59, Ag85C, 19 kDa lipoprotein, MPT32 and alpha-crystallin, EsxG, Rv2430c, Rv2041c, or at least one T-cell epitope of any of the above mentioned antigens ((Skjot et al, 2000; Danish Patent application PA 2000 00666; Danish Patent application PA 1999 01020; U.S. patent application Ser. No. 09/0505,739; Rosenkrands et al, 1998; Nagai et al, 1991).

Due to genetic variation, different individuals may react with immune responses of varying strength to the same polypeptide. Therefore, the vaccine according to the invention may comprise several different polypeptides in order to increase the immune response. The vaccine may comprise two or more polypeptides or immunogenic portions, where all of the polypeptides are as defined above, or some but not all of the peptides may be derived from virulent mycobacteria.

In one embodiment of the present invention, "nucleic acids" refers to a string of at least two base-sugar-phosphate combinations. The term includes, in one embodiment, DNA and RNA. "Nucleotides" refers, in one embodiment, to the monomeric units of nucleic acid polymers. RNA may be, in one embodiment, in the form of a tRNA (transfer RNA), snRNA (small nuclear RNA), rRNA (ribosomal RNA), mRNA (messenger RNA), anti-sense RNA, small inhibitory RNA (siRNA), micro RNA (miRNA) and ribozymes. The use of siRNA and miRNA has been described (Caudy A A et al, Genes & Devel 16: 2491-96 and references cited therein). DNA may be in form of plasmid DNA, viral DNA, linear DNA, or chromosomal DNA or derivatives of these groups. In addition, these forms of DNA and RNA may be single, double, triple, or quadruple stranded. The term also includes, in another embodiment, artificial nucleic acids that may contain other types of backbones but the same bases. In one embodiment, the artificial nucleic acid is a PNA (peptide nucleic acid). PNA contain peptide backbones and nucleotide bases and are able to bind, in one embodiment, to both DNA and RNA molecules. In another embodiment, the nucleotide is oxetane modified. In another embodiment, the nucleotide is modified by replacement of one or more phosphodiester bonds with a phosphorothioate bond. In another embodiment, the artificial nucleic acid contains any other variant of the phosphate backbone of native nucleic acids known in the art. The use of phosphothiorate nucleic acids and PNA are known to those skilled in the art, and are described in, for example, Neilsen P E, Curr Opin Struct Biol 9:353-57; and Raz N K et al Biochem Biophys Res Commun. 297:1075-84. The production and use of nucleic acids is known to those skilled in art and is described, for example, in Molecular Cloning, (2001), Sambrook and Russell, eds. and Methods in Enzymology: Methods for molecular cloning in eukaryotic cells (2003) Purchio and G. C. Fareed. Each nucleic acid derivative represents a separate embodiment of the present invention.

Regardless of the method of preparation, the antigens described herein are "antigenic." More specifically, the antigens have the ability to react with sera obtained from an *M. tuberculosis*-infected individual. Reactivity may be evaluated using, for example, the representative ELISA assays described herein, where an absorbance reading with sera from infected individuals that is at least three standard deviations above the absorbance obtained with sera from uninfected individuals is considered positive.

Antigenic portions of *M. tuberculosis* antigens may be prepared and identified using well known techniques, such as those summarized in Paul, Fundamental Immunology, 3d ed., Raven Press, 1993, pp. 243-247 and references cited therein. Such techniques include screening polypeptide portions of the native antigen for antigenic properties. The representative ELISAs described herein may generally be employed in these screens. An antigenic portion of a polypeptide is a portion that, within such representative assays, generates a signal in such assays that is substantially similar to that generated by the full-length antigen. In other words, an antigenic portion of a *M. tuberculosis* antigen generates at least about 20%, and preferably about 100%, of the signal induced by the full-length antigen in a model ELISA as described herein.

Portions and other variants of *M. tuberculosis* antigens may be generated by synthetic or recombinant means. Synthetic polypeptides having fewer than about 100 amino acids, and generally fewer than about 50 amino acids, may be generated using techniques well known in the art. For example, such polypeptides may be synthesized using any of the commercially available solid-phase techniques, such as the Merrifield solid-phase synthesis method, where amino acids are sequentially added to a growing amino acid chain. See Merrifield, J. Am. Chem. Soc. 85:2149-2146, 1963. Equipment for automated synthesis of polypeptides is commercially available from suppliers such as Applied BioSystems, Inc., Foster City, Calif., and may be operated according to the manufacturer's instructions. Variants of a native antigen may generally be prepared using standard mutagenesis techniques, such as oligonucleotide-directed site-specific mutagenesis. Sections of the DNA sequence may also be removed using standard techniques to permit preparation of truncated polypeptides.

In one embodiment, the present invention provides a method of diagnosing a parasitic infection prior to diagnosing an infectious disease.

In one embodiment, the parasite is a helminth. In another embodiment, the helminth is a platyhelminth, which in one embodiment, is a Flatworm. In another embodiment, the platyhelminth is a Cestoda, which in one embodiment is a tapeworm. In another embodiment, the platyhelminth is a Trematode, which in one embodiment is a fluke. In another embodiment, the helminth is a Nematode, which in one embodiment is a roundworm.

In one embodiment, the fluke is a blood fluke, which in one embodiment is a *Schistosoma mansoni/japonicum/mekongi/haematobium* (Schistosomiasis) or *Trichobilharzia regenti* (Swimmer's itch), in another embodiment, the fluke is a liver fluke, which in one embodiment is *Clonorchis sinensis* (Clonorchiasis), *Fasciola hepatica/gigantica* (Fascioliasis), or *Opisthorchis*. In another embodiment, the fluke is a lung fluke, which in one embodiment is *Paragonimus westermani* (Paragonimiasis). In another embodiment, the fluke is an intestinal fluke, which in one embodiment is *Fasciolopsis buski* (Fasciolopsiasis).

In one embodiment, the cestoda is a Cyclophyllidea, which in one embodiment is *Echinococcus granulosus/Echinococcus multilocularis* (Echinococcosis), *Taenia saginata* (beef)/*Taenia asiatica/Taenia solium* (pork) (Taeniasis/Cysticercosis), or *Hymenolepis nana/Hymenolepis diminuta* (Hymenolepiasis). In another embodiment, the cestoda is a Pseudophyllidea, which in one embodiment, is *Diphyllobothrium latum* (Diphyllobothriasis), *Spirometra erinaceieuropaei* (Sparganosis), or *Diphyllobothrium mansonoides* (Sparganosis).

In one embodiment, the nematode is Secernentea, which in one embodiment is a Spirurida, Strongylida (hookworm), Ascaridida, Rhabditida, Oxyurida, Camallanina, Spirurina, Filarioidea (Filariasis), Thelazioidea, or Spiruroidea. In one embodiment, the nematode is *Dracunculus medinensis* (Dracunculiasis) *Onchocerca volvulus* (Onchocerciasis), *Loa boa* (*Loa boa* filariasis), *Mansonella* (Mansonelliasis), *Dirofilaria repens* (Dirofilariasis), Filariad species (*Wuchereria*, and *Brugia* genus, e.g., *Wuchereria bancrofti, Brugia malayi, Brugia timori*), *Gnathostoma spinigerum/Gnathostoma hispidum* (Gnathostomiasis), *Thelazia* (Thelaziasis), *Gongylonema, Ancylostoma duodenale/Ancylostoma braziliense* (Ancylostomiasis, Cutaneous larva migrans),

*Necator americanus* (Necatoriasis), *Angiostrongylus cantonensis* (Angiostrongyliasis), *Angiostrongylus costaricensis*, Metastrongylus (Metastrongylosis), *Ascaris lumbricoides* (Ascariasis), *Anisakis* (Anisakiasis), *Toxocara canis/Toxocara cati* (Visceral larva migrans/Toxocariasis), *Baylisascaris, Strongyloides stercoralis* (Strongyloidiasis), *Enterobius vermicularis* (Enterobiasis, Pinworm), *Trichinella spiralis* (Trichinosis), *Trichuris trichiura* (Trichuriasis, Whipworm), a Stongyloides species, *Capillaria philippinensis* (Intestinal capillariasis), or *Capillaria hepatica*.

In one embodiment, the Platyhelminth is, Taeniarhynchus saginatus, Taenirhynchus confusus, *Fasciolopsis* species, Echinostomes, *Hymenolopis diminuta, Dicrocoelium dendriticum*, Heterophyes, Vampirolepis nana.

In another embodiment, the parasitic infection is any known in the art to affect a subject as provided herein.

In one embodiment, parasitic infection leads to the development of two subpopulations of CD4$^+$ cells that are able to make IL-10 and inhibit CD40 agonist-initiated IL-12 production. Producing IL-10 to suppress the ability of DC to make IL-12 in response to CD40 ligation, facilitates Th2 polarization in mice infected with schistosomes. Hence, in one embodiment, parasitic infection drives immune responses towards Th2, possibly blocking effectiveness of HIV vaccines, leading to false negative results in clinical trials. In another embodiment, parasites significantly suppress the levels of specific IFN-gamma production. In another embodiment, parasites significantly suppress the levels of specific IFN-gamma production during a bacterial, viral, microbial, microorganism, pathogenic, or combination thereof, infection.

Methods for diagnosis of parasitic worm infections include microscopic examination of fecal samples, either directly in fecal smears or following concentration of ova and parasites by flotation in density media, and also in urine. For example, definitive diagnosis of schistosomiasis depends on detection of specific schistosome eggs excreted in stool and urine. This occurs from 5-13 weeks after infection and is determined by worm burden. Thick smears of feces, nucleopore filtration of urine, and formalin-ether concentration techniques for stool or urine are recommended. Collection of urine is usually recommended between noon and 2:00 pm, when excretion of ova is greatest.

Multiple examinations may be required in light or chronic infections. If infections are active, schistosome eggs contain live and mature miracidia. Studies suggest that adult human immunodeficiency virus (HIV)-1-related immunodeficiency does not impair the ability to excrete eggs in low-intensity infection with *S. haematobium, S. mansoni*, or both and that infection with HIV-1 may not have major implications for diagnosis and surveillance of schistosomiasis.

It is to be understood that tests including, but not limited to, urinalysis, liver function tests, imaging studies that further include but are not limited to chest radiography ultrasonography of the abdomen and pelvis intravenous pyelography, voiding cystourethrography, head, chest, abdominal, and spinal CT scanning and/or MRI and serological tests for antibodies to parasites are contemplated to be carried out in the present invention for the diagnosis of a parasitic infection.

Other tests include Liver biopsy, cystoscopy, and laparoscopy.

The CDC uses a combination of tests with purified adult worm antigens. The Falcon assay screening test enzyme-linked immunosorbent assay (FAST-ELISA) is 99% specific for all species and has a sensitivity of 99% for *S. mansoni* infection, 95% for *S. haematobium*, and 50% for *S. japonicum*. Because of false negative results with the FAST-ELISA, immunoblots using species-specific antigens are performed in cases of potential exposure to *S. haematobium* and *S. japonicum* infections.javascript:showcontext('active','references'): However, serologic tests cannot distinguish active from past infections.

In some endemic areas, *S. japonicum, S. mansoni*, and viral hepatitis are the most common causes of chronic liver disease. The hepatitis B surface antigen carrier state has been noted to be 4 times higher in patients with schistosomiasis, the significance of which is uncertain. Different explanations have been proposed for the association of *S. mansoni* with hepatitis B and include (1) impaired cell-mediated immunity, which reduces host resistance; (2) low socioeconomic conditions and educational levels, which increase the risk of exposure; and (3) repeated treatments in the past with intravenous or parenteral drugs or blood transfusions.

Identification of severity and staging of schistosomal disease is achieved by a combination of the investigations described above. This includes serology, abdominal and perihilar ultrasonography, body CT scanning, endoscopy, cystoscopy, laparoscopy, and histology. Acute schistosomal disease: Changes detected on ultrasonographic studies in acute schistosomiasis (Katayama fever) include focal liver hypoechogenicities that may reflect secondary abscess formation with bacterial superinfection, pleural effusions, and pericardial effusions. Enlarged lymph nodes may reveal an echodense center surrounded by an echopolar halo. Mild schistosomiasis: Laparoscopy reveals that the liver surface is mostly smooth, although multiple whitish markings and irregular wide grooves are observed with more advanced disease. Chronic schistosomiasis: Ultrasonographic features are characteristic and include echogenic thickening of the walls of portal branches and of the portal vein frequently extending to the gall bladder and ligamenta. Moderate schistosomiasis: Ultrasonography reveals areas of high echogenicity, and CT scanning reveals network patterns and lineal calcified spots. Severe schistosomiasis: Laparoscopy reveals a liver surface distorted with blocklike formations of variable size separated by grooved depressions, producing a turtle shell-like appearance. Ultrasonography reveals areas of high echogenicity, and CT scanning reveals network patterns and lineal calcified spots.

In one embodiment, the present invention provides a method of treating an infection in a subject infected with a parasite. In another embodiment, the present invention provides a method of treating an infection in a subject infected with a helminth. In one embodiment, the subject is infected with one parasite and an additional parasite for a total infection with two parasites. In another embodiment, one parasite is a helminth and the additional parasite is a protozoan parasite. In another embodiment, the protozoan parasite is malaria, *Leishmania, Toxoplasma*, or any other protozoan parasite known in the art. In one embodiment the non-parasite infection is an infectious disease. In another embodiment, the non-parasite infection is a bacterial infection. In another embodiment, the non-parasite infection is tuberculosis. In another embodiment, the non-parasite infection is a viral infection. In another embodiment, the viral infection is HIV.

In one embodiment, the helminth infection is a parasitic infection. In one embodiment, the helminth infection is a parasitic protist infection. In another embodiment, a helminth is a parasitic worm. In one embodiment, the helminth is *Schistosoma mansoni*.

In one embodiment, the vaccine for use in the methods of the present invention comprises a recombinant *Listeria monocytogenes*, in any form or embodiment provided herein. In one embodiment, the vaccine for use in the present invention consists of a recombinant *Listeria monocytogenes* of the present invention, in any form or embodiment provided herein. In another embodiment, the vaccine for use in the methods of the present invention consists essentially of a recombinant *Listeria monocytogenes* of the present invention, in any form or embodiment provided herein. In one embodiment, the term "comprise" refers to the inclusion of a recombinant *Listeria monocytogenes* in the vaccine, as well as inclusion of other vaccines or treatments that may be known in the art. In another embodiment, the term "consisting essentially of" refers to a vaccine, whose functional component is the recombinant *Listeria monocytogenes*, however, other components of the vaccine may be included that are not involved directly in the therapeutic effect of the vaccine and may, for example, refer to components which facilitate the effect of the recombinant *Listeria monocytogenes* (e.g. stabilizing, preserving, etc.). In another embodiment, the term "consisting" refers to a vaccine, which contains the recombinant *Listeria monocytogenes*.

In one embodiment, the vaccines provided herein induce antigen-specific vaccine responses toward immunodominant CTL and helper epitopes during chronic helminth infection (see FIGS. 11A & B, and Example 4 herein below). In another embodiment, varying the vaccine dose and regimen does not alter the vaccine response to the immunodominant epitope (See FIG. 12, Example 4 herein below). In another embodiment, several months after the last vaccination, responses to the immunodominant epitope by the effector CTL cells, does not differ between in response to chronic helminth infection (See FIG. 13A, Example 5, herein below).

In one embodiment, Antigen-specific CD8+ T cells are generated in the presence of Schistosome infection and persist for several months at levels comparable to uninfected (see Example 5 herein below).

In one embodiment, responses of effector cells, part of the cell-mediated immune response, are durable and unaltered by pre-existing chronic helminth infection (see Example 6 herein below).

In one embodiment, the vaccines provided herein induce immunological memory (see Example 7, herein below).

In one embodiment, *Listeria*-based vaccines provided herein induce functional effector cells in a Th2 environment.

In another embodiment, if vaccine responses by the helminth-infected subject, change, vaccine responses are restored after a second boost and/or praziquantel treatment of the helminth infection.

In another embodiment, the methods of the present invention comprise the step of administering a recombinant *Listeria monocytogenes*, in any form or embodiment as described herein. In one embodiment, the methods of the present invention consist of the step of administering a recombinant *Listeria monocytogenes* of the present invention, in any form or embodiment as described herein. In another embodiment, the methods of the present invention consist essentially of the step of administering a recombinant *Listeria monocytogenes* of the present invention, in any form or embodiment as described herein. In one embodiment, the term "comprise" refers to the inclusion of the step of administering a recombinant *Listeria monocytogenes* in the methods, as well as inclusion of other methods or treatments that may be known in the art. In another embodiment, the term "consisting essentially of" refers to a methods, whose functional component is the administration of recombinant *Listeria monocytogenes*, however, other steps of the methods may be included that are not involved directly in the therapeutic effect of the methods and may, for example, refer to steps which facilitate the effect of the administration of recombinant *Listeria monocytogenes*. In one embodiment, the term "consisting" refers to a method of administering recombinant *Listeria monocytogenes* with no additional steps.

In one embodiment, the *Listeria monocytogenes* fusion protein for use in the methods of the present invention will comprise a microbial, or infectious disease (bacteria, viral, fungal, parasitic, etc.) antigen and LLO, ActA, or a PEST sequence, in any form or embodiment as described herein. In another embodiment, the *Listeria monocytogenes* fusion protein for use in the present invention will consist of a microbial, or infectious disease (bacteria, viral, fungal, parasitic, etc.) antigen and LLO, ActA, or a PEST sequence of the present invention, in any form or embodiment as described herein. In one embodiment, the *Listeria monocytogenes* fusion protein for use in the methods of the present invention will consist essentially of a microbial, or infectious disease (bacteria, viral, fungal, parasitic, etc.) antigen and LLO, ActA, or a PEST sequence of the present invention, in any form or embodiment as described herein. In another embodiment, the term "comprise" refers to the inclusion of a microbial, or infectious disease (bacteria, viral, fungal, parasitic, etc.) antigen and LLO, ActA, or a PEST sequence in the *Listeria monocytogenes* fusion protein, as well as inclusion of other therapeutic heterologous peptides that may be known in the art. In one embodiment, the term "consisting essentially of" refers to a *Listeria monocytogenes* fusion protein, whose functional component is a microbial, or infectious disease (bacteria, viral, fungal, parasitic, etc.) antigen and LLO, ActA, or a PEST sequence, however, other heterologous sequences may be included that are not involved directly in the therapeutic effect of the *Listeria monocytogenes* fusion protein and may, for example, refer to components which facilitate the effect of the fusion protein. In another embodiment, the term "consisting" refers to a *Listeria monocytogenes* fusion protein, which contains only a microbial, or infectious disease (bacteria, viral, fungal, parasitic, etc.) antigen and LLO, ActA, or a PEST sequence.

In one embodiment, the *Listeria monocytogenes* for use in the methods of the present invention will express and secrete a microbial or infectious disease (bacteria, viral, fungal, parasitic, etc.) antigen, in any form or embodiment as described herein in addition to other heterologous, therapeutic peptides. In one embodiment, the *Listeria monocytogenes* for use in the present invention will express and secrete a microbial or viral or infectious disease (bacteria, viral, fungal, parasitic, etc.) antigen of the present invention, in any form or embodiment as described herein in addition to other heterologous, non-therapeutic peptides. In one embodiment, the *Listeria monocytogenes* for use in the methods of the present invention will express and secrete a microbial or infectious disease (bacteria, viral, fungal, parasitic, etc.) antigen of the present invention, in any form or embodiment as described herein, but without the expression or secretion of other heterologous peptides.

In one embodiment, the recombinant *Listeria monocytogenes* for use in the present invention secretes a heterologous peptide. In another embodiment, the recombinant *List-*

*eria monocytogenes* for use in the present invention expresses a heterologous peptide. In another embodiment, the recombinant *Listeria monocytogenes* for use in the present invention expresses and secretes a heterologous peptide, as described herein. In another embodiment, the heterologous peptide is derived from a bacterial, viral, microbial, microorganism, pathogenic, or combination thereof, infection.

In one embodiment, attenuated *Listeria* strains, such as LM delta-actA mutant (Brundage et al, 1993, Proc. Natl. Acad. Sci., USA, 90:11890-11894), *L. monocytogenes* delta-plcA (Camilli et al, 1991, J. Exp. Med., 173:751-754), or delta-ActA, delta INL-b (Brockstedt et 5 al, 2004, PNAS, 101:13832-13837) are used in the present invention. In another embodiment, attenuated *Listeria* strains are constructed by introducing one or more attenuating mutations, as will be understood by one of average skill in the art when equipped with the disclosure herein. Examples of such strains include, but are not limited to *Listeria* strains auxotrophic for aromatic amino acids (Alexander et al, 1993, Infection and Immunity 10 61:2245-2248) and mutant for the formation of lipoteichoic acids (Abachin et al, 2002, Mol. Microbiol. 43:1-14) and those attenuated by a lack of a virulence gene. In another embodiment, the recombinant *Listeria* provided herein lacks an ActA gene.

In one embodiment, the recombinant *Listeria monocytogenes* vaccine provided herein overcomes helminth-induced suppression of Th1-mediated response to induce an infectious disease-specific cell mediated immune response. In another embodiment, the recombinant *Listeria monocytogenes* vaccine provided herein skews the immune response in a helminth-infected subject from Th2 to Th1. In another embodiment, administration of a *Listeria* vector-HIV-1 gag vaccine, developed to a subject chronically infected with the helminth parasite *Schistosoma mansoni*, drives significant immune responses to HIV-1 gag CTL and T helper epitopes. In another embodiment, *Listeria* vector vaccines are capable of driving vaccine-specific immune responses in helminth infected populations.

In another embodiment, anthelmintic drugs and/or antibiotics are used in conjunction with the vaccine for use in the methods of the present invention. In one embodiment, the anthelmintic drugs are albendazole, benzimidazole, imidothiazole/morantel, macrocyclic lactones, Ivermectin, rafoxanide. In one embodiment, the antibiotics are rifampicin, isoniazid, or a combination thereof.

The vaccine combination of the invention typically includes as one of the vaccines a nucleic acid vaccine, preferably DNA. Nucleic acid vaccines as defined herein, typically plasmid expression vectors, are not encapsidated in a viral particle. The nucleic acid vaccine is directly introduced into the cells of the individual receiving the vaccine regimen. This approach is described, for instance, in Wolff et. al., Science 247:1465 (1990) as well as U.S. Pat. Nos. 5,580,859; 5,589,466; 5,804,566; 5,739,118; 5,736,524; 5,679,647; and WO 98/04720. Examples of DNA-based delivery technologies include, "naked DNA", facilitated (bupivicaine, polymers, peptide-mediated) delivery, and cationic lipid complexes or liposomes. The nucleic acids can be administered using ballistic delivery as described, for instance, in U.S. Pat. No. 5,204,253 or pressure (see, e.g., U.S. Pat. No. 5,922,687). Using this technique, particles comprised solely of DNA are administered, or in an alternative embodiment, the DNA can be adhered to particles, such as gold particles, for administration.

As is well known in the art, a large number of factors can influence the efficiency of expression of antigen genes and/or the immunogenicity of DNA vaccines. Examples of such factors include the reproducibility of inoculation, construction of the plasmid vector, choice of the promoter used to drive antigen gene expression and stability of the inserted gene in the plasmid.

Any of the conventional vectors used for expression in eukaryotic cells may be used for directly introducing DNA into tissue. Expression vectors containing regulatory elements from eukaryotic viruses are typically used in eukaryotic expression vectors, e.g., SV40 CMB vectors. Other exemplary eukaryotic vectors include pMSG, pAV009/A+, pMTO10/A+, pMAMneo-5, and any other vector allowing expression of proteins under the direction of such promoters as the SV40 early promoter, SV40 later promoter, metallothionein promoter, human cytomegalovirus promoter, murine mammary tumor virus promoter, Rous sarcoma virus promoter, polyhedrin promoter, or other promoters shown effective for expression in eukaryotic cells.

Therapeutic quantities of plasmid DNA can be produced for example, by fermentation in *E. coli*, followed by purification. Aliquots from the working cell bank are used to inoculate growth medium, and grown to saturation in shaker flasks or a bioreactor according to well known techniques. Plasmid DNA can be purified using standard bioseparation technologies such as solid phase anion-exchange resins. If required, supercoiled DNA can be isolated from the open circular and linear forms using gel electrophoresis or other methods.

Recombinant polypeptides containing portions and/or variants of a native antigen may be readily prepared from a DNA sequence encoding the polypeptide using a variety of techniques well known to those of ordinary skill in the art. For example, supernatants from suitable host/vector systems, which secrete recombinant protein into culture media, may be first concentrated using a commercially available filter. Following concentration, the concentrate may be applied to a suitable purification matrix such as an affinity matrix or an ion exchange resin. Finally, one or more reverse phase HPLC steps can be employed to further purify a recombinant protein.

Protein and/or peptide homology for any amino acid sequence listed herein is determined, in one embodiment, by methods well described in the art, including immunoblot analysis, or via computer algorithm analysis of amino acid sequences, utilizing any of a number of software packages available, via established methods. Some of these packages may include the FASTA, BLAST, MPsrch or Scanps packages, and may employ the use of the Smith and Waterman algorithms, and/or global/local or BLOCKS alignments for analysis, for example. Each method of determining homology represents a separate embodiment of the present invention.

Any of a variety of expression vectors known to those of ordinary skill in the art may be employed to express recombinant polypeptides as described herein. Expression may be achieved in any appropriate host cell that has been transformed or transfected with an expression vector containing a DNA molecule that encodes a recombinant polypeptide. Suitable host cells include prokaryotes, yeast and higher eukaryotic cells. Preferably, the host cells employed are *E. coli*, yeast or a mammalian cell line, such as COS or CHO. The DNA sequences expressed in this manner may encode naturally occurring antigens, portions of naturally occurring antigens, or other variants thereof.

In general, regardless of the method of preparation, the polypeptides disclosed herein are prepared in substantially pure form. Preferably, the polypeptides are at least about 80% pure, more preferably at least about 90% pure and most preferably at least about 99% pure. For use in the methods described herein, however, such substantially pure polypeptides may be combined.

In one embodiment, the vaccines of the present invention comprise an adjuvant, while in another embodiment, the vaccines do not comprise an adjuvant. The term "Adjuvant" refers, in another embodiment, to compounds that, when administered to an individual or tested in vitro, increase the immune response to an antigen in the individual or test system to which the antigen is administered. In another embodiment, an immune adjuvant enhances an immune response to an antigen that is weakly immunogenic when administered alone, i.e., inducing no or weak antibody titers or cell-mediated immune response. In another embodiment, the adjuvant increases antibody titers to the antigen. In another embodiment, the adjuvant lowers the dose of the antigen effective to achieve an immune response in the individual.

The adjuvant utilized in methods and compositions of the present invention is, in another embodiment, a CpG-containing nucleotide sequence. In another embodiment, the adjuvant is a CpG-containing oligonucleotide. In another embodiment, the adjuvant is a CpG-containing oligodeoxynucleotide (CpG ODN). In another embodiment, the adjuvant is ODN 1826. In another embodiment, the adjuvant is an aluminum salt adjuvant. In another embodiment, the aluminum salt adjuvant is an alum-precipitated vaccine. In another embodiment, the aluminum salt adjuvant is an alum-adsorbed vaccine. Aluminum-salt adjuvants are well known in the art and are described, for example, in Harlow, E. and D. Lane (1988; Antibodies: A Laboratory Manual Cold Spring Harbor Laboratory) and Nicklas, W. (1992; Aluminum salts. Research in Immunology 143:489-493).

In another embodiment, the adjuvant is a Montanide ISA adjuvant. In another embodiment, the adjuvant is a trimer of complement component C3d. In another embodiment, the trimer is covalently linked to the protein immunogen. In another embodiment, the adjuvant is MF59. In another embodiment, the adjuvant is a granulocyte/macrophage colony-stimulating factor (GM-CSF) protein. In another embodiment, the adjuvant is a mixture comprising a GM-CSF protein. In another embodiment, the adjuvant is a nucleotide molecule encoding GM-CSF. In another embodiment, the adjuvant is a mixture comprising a nucleotide molecule encoding GM-CSF. In another embodiment, the adjuvant is saponin QS21. In another embodiment, the adjuvant is a mixture comprising saponin QS21. In another embodiment, the adjuvant is monophosphoryl lipid A (MPL). In another embodiment, the adjuvant is a mixture comprising MPL. In another embodiment, the adjuvant is SBAS2. In another embodiment, the adjuvant is a mixture comprising SBAS2. In another embodiment, the adjuvant is an unmethylated CpG-containing oligonucleotide. In another embodiment, the adjuvant is a mixture comprising an unmethylated CpG-containing oligonucleotide. In another embodiment, the adjuvant is an immune-stimulating cytokine. In another embodiment, the adjuvant is a mixture comprising an immune-stimulating cytokine. In another embodiment, the adjuvant is a nucleotide molecule encoding an immune-stimulating cytokine. In another embodiment, the adjuvant is a mixture comprising a nucleotide molecule encoding an immune-stimulating cytokine. In another embodiment, the adjuvant is a mixture comprising a quill glycoside. In another embodiment, the adjuvant is a mixture comprising a bacterial mitogen. In another embodiment, the adjuvant is a mixture comprising a bacterial toxin. In another embodiment, the adjuvant is a mixture comprising any other adjuvant known in the art. In another embodiment, the adjuvant is a mixture of 2 of the above adjuvants. In another embodiment, the adjuvant is a mixture of 3 of the above adjuvants. In another embodiment, the adjuvant is a mixture of more than three of the above adjuvants.

In another embodiment, the methods of the present invention further comprise the step of administering to the subject a booster vaccination. In one embodiment, the booster vaccination follows a single priming vaccination. In another embodiment, a single booster vaccination is administered after the priming vaccinations. In another embodiment, two booster vaccinations are administered after the priming vaccinations. In another embodiment, three booster vaccinations are administered after the priming vaccinations. In one embodiment, the period between a prime and a boost vaccine is experimentally determined by the skilled artisan. In another embodiment, the period between a prime and a boost vaccine is 1 week, in another embodiment it is 2 weeks, in another embodiment, it is 3 weeks, in another embodiment, it is 4 weeks, in another embodiment, it is 5 weeks, in another embodiment it is 6-8 weeks, in yet another embodiment, the boost vaccine is administered 8-10 weeks after the prime vaccine.

In another embodiment, the booster vaccination comprises the use of an alternate form of a vaccine different to that of the priming vaccine. In another embodiment, the different or alternate form of the vaccine is a DNA vaccine encoding the fusion protein, a recombinant polypeptide comprising said fusion protein, a viral vector or a live recombinant *Listeria* vaccine vector. In another embodiment, the viral vector is an adenoviral vector.

Heterologous "prime boost" strategies have been effective for enhancing immune responses and protection against numerous pathogens. Schneider et al., Immunol. Rev. 170: 29-38 (1999); Robinson, H. L., Nat. Rev. Immunol. 2:239-50 (2002); Gonzalo, R. M. et al., Vaccine 20:1226-31 (2002); Tanghe, A., Infect. Immun. 69:3041-7 (2001). Providing antigen in different forms in the prime and the boost injections appears to maximize the immune response to the antigen. DNA vaccine priming followed by boosting with protein in adjuvant or by viral vector delivery of DNA encoding antigen appears to be the most effective way of improving antigen specific antibody and CD4+ T-cell responses or CD8+ T-cell responses respectively. Shiver J. W. et al., Nature 415: 331-5 (2002); Gilbert, S. C. et al., Vaccine 20:1039-45 (2002); Billaut-Mulot, O. et al., Vaccine 19:95-102 (2000); Sin, J. I. et al., DNA Cell Biol. 18:771-9 (1999). Recent data from monkey vaccination studies suggests that adding CRL1005 poloxamer (12 kDa, 5% POE), to DNA encoding the HIV gag antigen enhances T-cell responses when monkeys are vaccinated with an HIV gag DNA prime followed by a boost with an adenoviral vector expressing HIV gag (Ad5-gag). The cellular immune responses for a DNA/poloxamer prime followed by an Ad5-gag boost were greater than the responses induced with a DNA (without poloxamer) prime followed by Ad5-gag boost or for Ad5-gag only. Shiver, J. W. et al. Nature 415:331-5 (2002). U.S. Patent Appl. Publication No. US 2002/0165172 A1 describes simultaneous administration of a vector construct encoding an immunogenic portion of an antigen and a protein comprising the immunogenic portion of an antigen such that an immune response is generated. The document is limited to hepatitis B antigens and HIV antigens. Moreover, U.S. Pat. No. 6,500,432 is directed to methods of enhancing an immune response of nucleic acid vaccination by simultaneous administration of a polynucleotide and polypeptide of interest. According to the patent, simultaneous administration means administration of the polynucleotide and the polypeptide during the same immune response, preferably within 0-10 or 3-7 days of each other. The antigens contemplated by the patent include, among others, those of Hepatitis (all forms), HSV, HIV, CMV, EBV, RSV, VZV, HPV, polio, influenza, parasites (e.g., from the genus *Plasmodium*), and pathogenic bacteria (including but not limited to *M. tuberculosis, M. leprae, Chlamydia, Shigella, B. burgdorferi*, enterotoxigenic *E. coli, S. typhosa, H. pylori, V. cholerae, B. pertussis*, etc.). All of the above references are herein incorporated by reference in their entireties.

In another embodiment, the nucleic acid molecule of the methods and compositions of the present invention is operably linked to a promoter/regulatory sequence. In another embodiment, the first open reading frame of methods and compositions of the present invention is operably linked to a promoter/regulatory sequence. In another embodiment, the second open reading frame of methods and compositions of the present invention is operably linked to a promoter/regulatory sequence. In another embodiment, each of the open reading frames are operably linked to a promoter/regulatory sequence. Each possibility represents a separate embodiment of the present invention.

The skilled artisan, when equipped with the present disclosure and the methods provided herein, will readily understand that different transcriptional promoters, terminators, carrier vectors or specific gene sequences (e.g. those in commercially available cloning vectors) can be used successfully in methods and compositions of the present invention. As is contemplated in the present invention, these functionalities are provided in, for example, the commercially available vectors known as the pUC series. In another embodiment, non-essential DNA sequences (e.g. antibiotic resistance genes) are removed. Each possibility represents a separate embodiment of the present invention. In another embodiment, a commercially available plasmid is used in the present invention that can be constructed using methods well known in the art.

Another embodiment is a plasmid such as pCR2.1 (Invitrogen, La Jolla, Calif.), which is a prokaryotic expression vector with a prokaryotic origin of replication and promoter/regulatory elements to facilitate expression in a prokaryotic organism. In another embodiment, extraneous nucleotide sequences are removed to decrease the size of the plasmid and increase the size of the cassette that can be placed therein.

Such methods are well known in the art, and are described in, for example, Sambrook et al. (1989, Molecular Cloning: A Laboratory Manual, Cold Spring Harbor Laboratory Press, New York) and Ausubei et al. (1997, Current Protocols in Molecular Biology, Green & Wiley, New York).

In one embodiment, antibiotic resistance genes are used in the conventional selection and cloning processes commonly employed in molecular biology and vaccine preparation. Antibiotic resistance genes contemplated in the present invention include, but are not limited to, gene products that confer resistance to ampicillin, penicillin, methicillin, streptomycin, erythromycin, kanamycin, tetracycline, chloramphenicol (CAT), neomycin, hygromycin, gentamicin and others well known in the art. Each gene represents a separate embodiment of the present invention.

Methods for transforming bacteria are well known in the art, and include calcium-chloride competent cell-based methods, electroporation methods, bacteriophage-mediated transduction, chemical, and physical transformation techniques (de Boer et al, 1989, Cell 56:641-649; Miller et al, 1995, FASEB J., 9:190-199; Sambrook et al. 1989, Molecular Cloning: A Laboratory Manual, Cold Spring Harbor Laboratory, New York; Ausubel et al., 1997, Current Protocols in Molecular Biology, John Wiley & Sons, New York; Gerhardt et al., eds., 1994, Methods for General and Molecular Bacteriology, American Society for Microbiology, Washington, D.C.; Miller, 1992, A Short Course in Bacterial Genetics, Cold Spring Harbor Laboratory Press, Cold Spring Harbor, N.Y.) In another embodiment, the *Listeria* vaccine strain of the present invention is transformed by electroporation. Each method represents a separate embodiment of the present invention.

In another embodiment, conjugation is used to introduce genetic material and/or plasmids into bacteria. Methods for conjugation are well known in the art, and are described, for example, in Nikodinovic J et al. (A second generation snp-derived *Escherichia coli-Streptomyces* shuttle expression vector that is generally transferable by conjugation. Plasmid. 2006 November; 56(3):223-7) and Auchtung J M et al (Regulation of a *Bacillus subtilis* mobile genetic element by intercellular signaling and the global DNA damage response. Proc Natl Acad Sci USA. 2005 Aug. 30; 102 (35):12554-9). Each method represents a separate embodiment of the present invention.

"Transforming," in one embodiment, is used identically with the term "transfecting," and refers to engineering a bacterial cell to take up a plasmid or other heterologous DNA molecule. In another embodiment, "transforming" refers to engineering a bacterial cell to express a gene of a plasmid or other heterologous DNA molecule. Each possibility represents a separate embodiment of the present invention.

Plasmids and other expression vectors useful in the present invention are described elsewhere herein, and can include such features as a promoter/regulatory sequence, an origin of replication for gram negative and gram positive bacteria, an isolated nucleic acid encoding a fusion protein and an isolated nucleic acid encoding an amino acid metabolism gene. Further, an isolated nucleic acid encoding a fusion protein and an amino acid metabolism gene will have a promoter suitable for driving expression of such an isolated nucleic acid. Promoters useful for driving expression in a bacterial system are well known in the art, and include bacteriophage lambda, the bla promoter of the beta-lactamase gene of pBR322, and the CAT promoter of the chloramphenicol acetyl transferase gene of pBR325. Further examples of prokaryotic promoters include the major right and left promoters of 5 bacteriophage lambda (PL and PR), the trp, recA, lacZ, laI, and gal promoters of *E. coli*, the alpha-amylase (Ulmanen et al, 1985. J. Bacteriol. 162:176-182) and the S28-specific promoters of *B. subtilis* (Gilman et al, 1984 Gene 32:11-20), the promoters of the bacteriophages of *Bacillus* (Gryczan, 1982, In: The Molecular Biology of the Bacilli, Academic Press, Inc., New York), and *Streptomyces* promoters (Ward et al, 1986, Mol. Gen. Genet. 203:468-478). Additional prokaryotic promoters contemplated in the present invention are reviewed in, for example, Glick (1987, J. Ind. Microbiol. 1:277-282); Cenatiempo, (1986, Biochimie, 68:505-516); and Gottesman, (1984, Ann. Rev. Genet. 18:415-442). Further examples of promoter/regulatory elements contemplated in the present invention include, but are not limited to the Listerial prfA promoter, the Listerial hly promoter, the Listerial p60 promoter and the Listerial ActA promoter (GenBank Acc. No. NC_003210) or fragments thereof.

In another embodiment, a plasmid of methods and compositions of the present invention comprises a gene encoding a fusion protein. In another embodiment, subsequences are cloned and the appropriate subsequences cleaved using appropriate restriction enzymes. The fragments are then, in another embodiment, ligated to produce the desired DNA sequence. In another embodiment, DNA encoding the antigen is produced using DNA amplification methods, for example polymerase chain reaction (PCR). First, the segments of the native DNA on either side of the new terminus are amplified separately. The 5' end of the one amplified sequence encodes the peptide linker, while the 3' end of the other amplified sequence also encodes the peptide linker. Since the 5' end of the first fragment is complementary to the 3' end of the second fragment, the two fragments (after partial purification, e.g. on LMP agarose) can be used as an overlapping template in a third PCR reaction. The amplified sequence will contain codons, the segment on the carboxy side of the opening site (now forming the amino sequence), the linker, and the sequence on the amino side of the opening site (now forming the carboxyl sequence). The antigen is ligated into a plasmid. Each method represents a separate embodiment of the present invention.

In another embodiment, the present invention further comprises a phage based chromosomal integration system for clinical applications. In another embodiment, in order to avoid a "phage curing step," a phage integration system based on PSA is used (Lauer, et al., 2002 J Bacteriol, 184:4177-4186). This requires, in another embodiment, continuous selection by antibiotics to maintain the integrated gene. Thus, in another embodiment, the current invention enables the establishment of a phage based chromosomal integration system that does not require selection with antibiotics. Instead, an auxotrophic host strain is complemented.

The recombinant proteins of the present invention are synthesized, in another embodiment, using recombinant DNA methodology. This involves, in one embodiment, creating a DNA sequence that encodes the fusion protein, placing the DNA in an expression cassette, such as the plasmid of the present invention, under the control of a particular promoter/regulatory element, and expressing the protein. DNA encoding the fusion protein (e.g. non-hemolytic LLO/antigen) of the present invention is prepared, in another embodiment, by any suitable method, including, for example, cloning and restriction of appropriate sequences or direct chemical synthesis by methods such as the phosphotriester method of Narang et al. (1979, Meth. Enzymol. 68: 90-99); the phosphodiester method of Brown et al. (1979, Meth. Enzymol 68: 109-151); the diethylphosphoramidite method of Beaucage et al. (1981, Tetra. Lett., 22: 15 1859-1862); and the solid support method of U.S. Pat. No. 4,458,066.

In another embodiment, chemical synthesis is used to produce a single stranded oligonucleotide. This single stranded oligonucleotide is converted, in various embodiments, into double stranded DNA by hybridization with a complementary sequence, or by polymerization with a DNA polymerase using the single strand as a template. One of skill in the art would recognize that while chemical synthesis of DNA is limited to sequences of about 100 bases, longer sequences can be obtained by the ligation of shorter sequences. In another embodiment, subsequences are cloned and the appropriate subsequences cleaved using appropriate restriction enzymes. The fragments are then be ligated to produce the desired DNA sequence.

In another embodiment, DNA encoding the fusion protein or the recombinant protein of the present invention is cloned using DNA amplification methods such as polymerase chain reaction (PCR). Thus, the gene for non-hemolytic LLO is PCR amplified, using a sense primer comprising a suitable restriction site and an antisense primer comprising another restriction site, e.g. a non-identical restriction site to facilitate cloning. The same is repeated for the isolated nucleic acid encoding an antigen. Ligation of the non-hemolytic LLO and antigen sequences and insertion into a plasmid or vector produces a vector encoding non-hemolytic LLO joined to a terminus of the antigen. The two molecules are joined either directly or by a short spacer introduced by the restriction site.

In another embodiment, the molecules are separated by a peptide spacer consisting of one or more amino acids, generally the spacer will have no specific biological activity other than to join the proteins or to preserve some minimum distance or other spatial relationship between them. In another embodiment, the constituent amino acids of the spacer are selected to influence some property of the molecule such as the folding, net charge, or hydrophobicity. In another embodiment, the nucleic acid sequences encoding the fusion or recombinant proteins are transformed into a variety of host cells, including *E. coli*, other bacterial hosts, such as *Listeria*, yeast, and various higher eukaryotic cells such as the COS, CHO and HeLa cells lines and myeloma cell lines. The recombinant fusion protein gene will be operably linked to appropriate expression control sequences for each host. Promoter/regulatory sequences are described in detail elsewhere herein. In another embodiment, the plasmid further comprises additional promoter regulatory elements, as well as a ribosome binding site and a transcription termination signal. For eukaryotic cells, the control sequences will include a promoter and an enhancer derived from e.g. immunoglobulin genes, SV40, cytomegalovirus, etc., and a polyadenylation sequence. In another embodiment, the sequences include splice donor and acceptor sequences.

In one embodiment, the term "operably linked" refers to a juxtaposition wherein the components so described are in a relationship permitting them to function in their intended manner. A control sequence "operably linked" to a coding sequence is ligated in such a way that expression of the coding sequence is achieved under conditions compatible with the control sequences.

In another embodiment, in order to select for an auxotrophic bacteria comprising the plasmid, transformed auxotrophic bacteria are grown on a media that will select for expression of the amino acid metabolism gene. In another embodiment, a bacteria auxotrophic for D-glutamic acid synthesis is transformed with a plasmid comprising a gene for D-glutamic acid synthesis, and the auxotrophic bacteria grow in the absence of D-glutamic acid, whereas auxotrophic bacteria that have not been transformed with the plasmid, or are not expressing the plasmid encoding a protein for D-glutamic acid synthesis, do not grow. In another embodiment, a bacterium auxotrophic for D-alanine synthesis will grow in the absence of D-alanine when transformed and expressing the plasmid of the present invention if the plasmid comprises an isolated nucleic acid encoding an amino acid metabolism enzyme for D-alanine synthesis. Such methods for making appropriate media comprising or lacking necessary growth factors, supplements, amino acids, vitamins, antibiotics, and the like are well known in the art, and are available commercially (Becton-Dickinson, Franklin Lakes, N.J.). Each method represents a separate embodiment of the present invention.

In another embodiment, once the auxotrophic bacteria comprising the plasmid of the present invention have been selected on appropriate media, the bacteria are propagated in the presence of a selective pressure. Such propagation comprises growing the bacteria in media without the auxotrophic factor. The presence of the plasmid expressing an amino acid metabolism enzyme in the auxotrophic bacteria ensures that the plasmid will replicate along with the bacteria, thus continually selecting for bacteria harboring the plasmid. The skilled artisan, when equipped with the present disclosure and methods herein will be readily able to scale-up the production of the Listeria vaccine vector by adjusting the volume of the media in which the auxotrophic bacteria comprising the plasmid are growing.

The skilled artisan will appreciate that, in another embodiment, other auxotroph strains and complementation systems are adopted for the use with this invention.

In one embodiment, the Listeria vaccine vector provided herein is a recombinant Listeria strain, wherein in another embodiment it is a recombinant Listeria monocytogenes strain. In another embodiment, the recombinant Listeria strain is an auxotrophic Listeria strain. In another embodiment, the recombinant Listeria strain o is a dal/dat mutant. In another embodiment, the recombinant Listeria strain of comprises an episomal expression vector comprising a metabolic enzyme that complements the auxotrophy of said auxotrophic Listeria strain. In another embodiment, the recombinant Listeria strain comprises an amino acid metabolism enzyme. In another embodiment, the metabolic enzyme catalyzes a formation of an amino acid used for a cell wall synthesis in said recombinant Listeria strain. In another embodiment, the metabolic enzyme is an alanine racemase enzyme. In another embodiment, the metabolic enzyme is a D-amino acid transferase enzyme.

In one embodiment, the recombinant Listeria strain provided herein been passaged through an animal host.

In another embodiment, the vaccines and immunogenic compositions utilized in any of the methods described above have any of the characteristics of vaccines and immunogenic compositions of the present invention. Each characteristic represents a separate embodiment of the present invention.

Various embodiments of dosage ranges are contemplated by this invention. In one embodiment, in the case of vaccine vectors, the dosage is in the range of 0.4 $LD_{50}$/dose. In another embodiment, the dosage is from about 0.4-4.9 $LD_{50}$/dose. In another embodiment the dosage is from about 0.5-0.59 $LD_{50}$/dose. In another embodiment the dosage is from about 0.6-0.69 $LD_{50}$/dose. In another embodiment the dosage is from about 0.7-0.79 $LD_{50}$/dose. In another embodiment the dosage is about 0.8 $LD_{50}$/dose. In another embodiment, the dosage is 0.4 $LD_{50}$/dose to 0.8 of the $LD_{50}$/dose.

In another embodiment, the dosage is $10^7$ bacteria/dose. In another embodiment, the dosage is $1.5 \times 10^7$ bacteria/dose. In another embodiment, the dosage is $2 \times 10^7$ bacteria/dose. In another embodiment, the dosage is $3 \times 10^7$ bacteria/dose. In another embodiment, the dosage is $4 \times 10^7$ bacteria/dose. In another embodiment, the dosage is $6 \times 10^7$ bacteria/dose. In another embodiment, the dosage is $8 \times 10^7$ bacteria/dose. In another embodiment, the dosage is $1 \times 10^8$ bacteria/dose. In another embodiment, the dosage is $1.5 \times 10^8$ bacteria/dose. In another embodiment, the dosage is $2 \times 10^8$ bacteria/dose. In another embodiment, the dosage is $3 \times 10^8$ bacteria/dose. In another embodiment, the dosage is $4 \times 10^8$ bacteria/dose. In another embodiment, the dosage is $6 \times 10^8$ bacteria/dose. In another embodiment, the dosage is $8 \times 10^8$ bacteria/dose. In another embodiment, the dosage is $1 \times 10^9$ bacteria/dose. In another embodiment, the dosage is $1.5 \times 10^9$ bacteria/dose. In another embodiment, the dosage is $2 \times 10^9$ bacteria/dose. In another embodiment, the dosage is $3 \times 10^9$ bacteria/dose. In another embodiment, the dosage is $5 \times 10^9$ bacteria/dose. In another embodiment, the dosage is $6 \times 10^9$ bacteria/dose. In another embodiment, the dosage is $8 \times 10^9$ bacteria/dose. In another embodiment, the dosage is $1 \times 10^{10}$ bacteria/dose. In another embodiment, the dosage is $1.5 \times 10^{10}$ bacteria/dose. In another embodiment, the dosage is $2 \times 10^{10}$ bacteria/dose. In another embodiment, the dosage is $3 \times 10^{10}$ bacteria/dose. In another embodiment, the dosage is $5 \times 10^{10}$ bacteria/dose. In another embodiment, the dosage is $6 \times 10^{10}$ bacteria/dose. In another embodiment, the dosage is $8 \times 10^{10}$ bacteria/dose. In another embodiment, the dosage is $8 \times 10^9$ bacteria/dose. In another embodiment, the dosage is $1 \times 10^{11}$ bacteria/dose. In another embodiment, the dosage is $1.5 \times 10^{11}$ bacteria/dose. In another embodiment, the dosage is $2 \times 10^{11}$ bacteria/dose. In another embodiment, the dosage is $3 \times 10^{11}$ bacteria/dose. In another embodiment, the dosage is $5 \times 10^{11}$ bacteria/dose. In another embodiment, the dosage is $6 \times 10^{11}$ bacteria/dose. In another embodiment, the dosage is $8 \times 10^{11}$ bacteria/dose. Each possibility represents a separate embodiment of the present invention.

In another embodiment, the present invention provides a kit comprising a reagent utilized in performing a method of the present invention. In another embodiment, the present invention provides a kit comprising a composition, tool, or instrument of the present invention.

The pharmaceutical compositions containing vaccines and compositions of the present invention are, in another embodiment, administered to a subject by any method known to a person skilled in the art, such as parenterally, paracancerally, transmucosally, transdermally, intramuscularly, intravenously, intra-dermally, subcutaneously, intraperitonealy, intra-ventricularly, intra-cranially, intra-vaginally or intra-tumorally.

In another embodiment of the methods and compositions provided herein, the vaccines or compositions are administered orally, and are thus formulated in a form suitable for oral administration, i.e. as a solid or a liquid preparation. Suitable solid oral formulations include tablets, capsules, pills, granules, pellets and the like. Suitable liquid oral formulations include solutions, suspensions, dispersions, emulsions, oils and the like. In another embodiment of the present invention, the active ingredient is formulated in a capsule. In accordance with this embodiment, the compositions of the present invention comprise, in addition to the active compound and the inert carrier or diluent, a hard gelating capsule.

In another embodiment, the vaccines or compositions are administered by intravenous, intra-arterial, or intra-muscular injection of a liquid preparation. Suitable liquid formulations include solutions, suspensions, dispersions, emulsions, oils and the like. In one embodiment, the pharmaceutical compositions are administered intravenously and are thus formulated in a form suitable for intravenous administration. In another embodiment, the pharmaceutical compositions are administered intra-arterially and are thus formulated in a form suitable for intra-arterial administration. In another embodiment, the pharmaceutical compositions are administered intra-muscularly and are thus formulated in a form suitable for intra-muscular administration.

The term "therapeutically effective dose" or "therapeutic effective amount" means a dose that produces the desired effect for which it is administered. The exact dose will be ascertainable by one skilled in the art using known techniques.

The term "subject" or "patient" refers a human at risk of having or actually having HIV, tuberculosis, malaria or any other infectious disease as provided herein. It also refers to a human having or at the risk of having a parasitic infection. The term "subject" does not exclude an individual that is normal in all respects. Moreover, the terms "subject," "host," "patient," and "individual" are used interchangeably herein to refer to any mammalian subject for whom diagnosis or therapy is desired, particularly humans. Other subjects may include cattle, dogs, cats, guinea pigs, rabbits, rats, mice, horses, and so on.

The term "about" as used herein means in quantitative terms plus or minus 5%, or in another embodiment plus or minus 10%, or in another embodiment plus or minus 15%, or in another embodiment plus or minus 20%.

The following examples are presented in order to more fully illustrate the preferred embodiments of the invention. They should in no way be construed, however, as limiting the broad scope of the invention.

EXAMPLES

Materials and Methods

Parasites and Mice

Female Balb/c mice (Harlan) were infected with 35-50 infectious cercariae of Schistosoma mansoni by intraperitoneal (i.p.) injection. For Schistosome-infected mice, the helminth infection was verified by the presence of anti-egg and/or anti-worm antibodies by ELISA in sera collected at 10 weeks post-infection.

Bacterial Strains

Lm-Gag refers to a recombinant strain of *L. monocytogenes*, which carries a copy of the HIV-1 strain HXB gag gene stably integrated into the listerial chromosome and which secretes the gag gene product as determined by Western blotting. The strain was grown in brain/heart infusion (BHI) medium (Difco, Detroit, Mich.).

Vaccination of Mice

Female Balb/c mice were primed i.p. with 0.2 (or 0.1, as indicated) $LD_{50}$ *Listeria*-vector HIV-1 vaccine (Lm-gag, from Y. Paterson, University of Pennsylvania), control *Listeria*-vector HPV vaccine (Lm-E7, from Y. Paterson, University of Pennsylvania) or left unvaccinated. Mice were boosted two weeks after the prime in an identical manner.

Analysis of T-Cell Responses

Two weeks after the final immunization, mice were sacrificed, spleens were collected from individual mice and splenocytes were prepared using standard methodology. In brief, splenocytes were cultured in 24-well plates with Ag at 37° C. in 1 ml of RPMI 1640 supplemented with 10% FBS, 100 U/ml penicillin, 100 mg/ml streptomycin, 2 mM L-glutamine, and 50 mM 2-ME. After 3 days, supernatants of duplicate cultures were collected and stored at 22° C. until samples were tested for cytokines by ELISA.

For cytokine analysis by ELISA, splenocytes were harvested and plated at 1.5 million cells per well in 48-well plates in the presence of media, SEA or conA (as a positive control). After incubation for 72 hours, supernatants were harvested and analyzed for cytokine level by ELISA (BD). For antigen-specific IFN-γ ELISpot, splenocytes were harvested and plated at 300K and 150K cells per well in IFN-γ ELISpot plates in the presence of media, specific CTL peptide, irrelevant peptide, specific helper peptide or conA (as a positive control). After incubation for 20 hours, ELISpots (BD) were performed and spots counted by the Immunospot analyzer (C.T.L.). Number of spots per million splenocytes were graphed.

Splenocytes were counted using a Coulter Counter, Z1 (Beckman Coulter Inc., Fullerton, Calif., USA). The frequency of IFN-γ producing CD8+ T cells after re-stimulation with gag-CTL, gag-helper, medium, an irrelevant antigen, and con A (positive control) was determined using a standard TN-γ-based ELISPOT assay.

Briefly, IFN-γ was detected using the mAb R46-A2 at 5 mg/ml and polyclonal rabbit anti-IFN-γ used at an optimal dilution (kindly provided by Dr. Phillip Scott, University of Pennsylvania, Philadelphia, Pa.). The levels of IFN-γ were calculated by comparison with a standard curve using murine rIFN-γ. Plates were developed using a peroxidase-conjugated goat anti-rabbit IgG Ab (IFN-γ). Plates were then read at 405 nm. The lower limit of detection for the assays was 30 pg/ml.

ELISA

At 2 weeks post last vaccination (wplv), splenocytes were harvested and plated at 1.5 million cells per well in 48-well plates in the presence of media, 25 μg/ml Schistosome soluble egg antigen (SEA) or 1 μg/ml concanavalin A (conA, as a positive control). After incubation for 72 hours, supernatants were harvested and analyzed for levels of IFN-γ, IL-4 and IL-10 by ELISA (Becton Dickinson), according to manufacturer's protocol.

ELISpot

Two wplv, splenocytes were harvested and plated at 300K and 150K cells per well in IFN-γ ELISpot plates (Becton Dickinson). The splenocytes were re-stimulated in the presence of media, 20 μM specific CTL peptide (H2-Kd-restricted, AMQMLKETI (Seq. ID. No. 1) from HIV-1 IIIB gag protein), 20 μM irrelevant peptide (H2-Kd-restricted, TYQRTRALV (Seq. ID. No. 2) from influenza nucleoprotein), 20 μM specific helper peptide (H2-d-restricted, NPPIPVGEIYKRWIILGLNK (Seq. ID. No. 3) from HIV-1 IIIB gag protein) or 1 μg/ml con A (as a positive control). Peptides were synthesized by Biosynthesis, Inc at greater than 95% purity. After incubation for 20 hours, ELISpots were performed according to manufacturer's instructions, counted using an Immunospot analyzer (C.T.L.), and graphed as number of spots per million splenocytes for the CTL and helper immunodominant epitopes.

Flow cytometry.

Splenocytes were stained with gag-tetramer (H2-Kd+ AMQMLKETI (Seq. ID. No. 1), Beckman Coulter) and anti-CD8, anti-CD62L and anti-CD197 antibodies (Becton Dickinson). Live cells (as indicated by using a LIVE/DEAD fixable dye, Invitrogen) were acquired and analyzed using an LSRII flow cytometer running FACSDiva (Becton Dickinson).

In Vivo Cytotoxic T Lymphocyte (CTL) Assay.

Target cells (splenocytes from naïve, syngeneic mice) were fluorescently labeled green (Vybrant CFDA SE Cell Tracer Kit, Invitrogen) or purple (CellTrace Violet Cell Proliferation Kit, Invitrogen), according to manufacturer's instructions. Cells were washed and then pulsed for 2 hours with 20 μM specific CTL or irrelevant peptide, respectively. Targets were mixed and one million cells were injected intravenously per vaccinated animal. After overnight (20 h) in vivo killing, splenocytes were collected and analyzed by flow cytometry for target recovery. Samples with >100 targets recovered are plotted.

Statistical Analysis

For pooled data, t test (two tailed, unpaired, unequal variance) was employed to determine if the original vaccine (0.2 Lm-gag P+B in a healthy mouse) differed from any of the vaccination strategies in the Schisto infected mouse. Values for both CTL and helper epitopes were compared and the p values are listed in Table 1.

Example 1

Vaccine Efficacy in a Model of Chronic Helminth Infection

Figure 1:
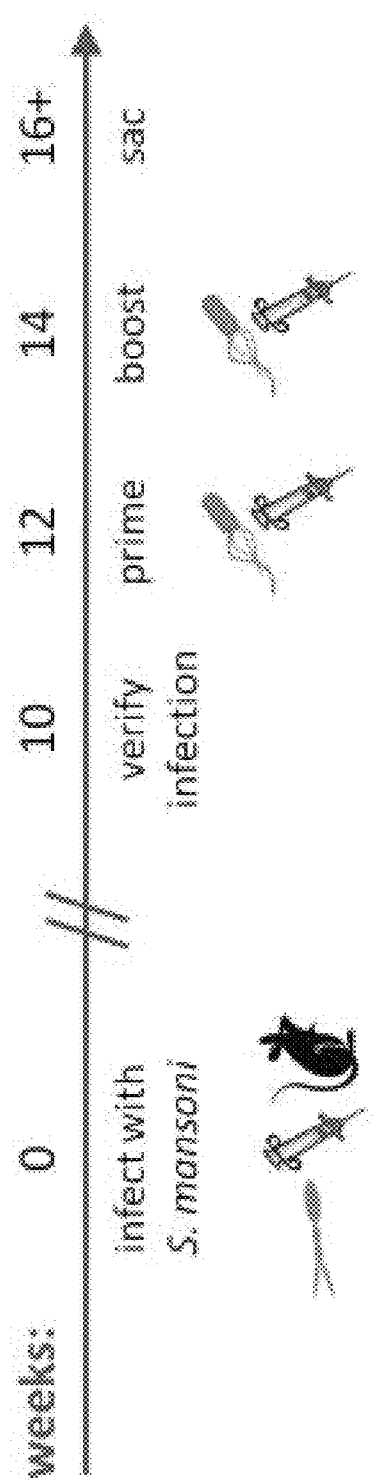
FIG. 1 shows an experimental outline in which Six to eight week old female Balb/c mice were either left naïve or infected by intraperitoneal injection of 50 cercariae of *Schistosoma mansoni*. Infection was verified at 10 weeks by ELISA for circulating antibodies against Schistosome soluble egg antigens (SEA). Twelve weeks post-infection, mice were primed i.p. with 0.2 (or 0.1) $LD_{50}$ *Listeria*-vector HIV-1 vaccine (Lm-gag) or control *Listeria*-vector HPV vaccine (Lm-E7) or left unvaccinated. Mice were boosted two weeks after the prime in an identical manner. Vaccine responses were evaluated two or more weeks after the last vaccination (wplv), as indicated.
Figure 2:
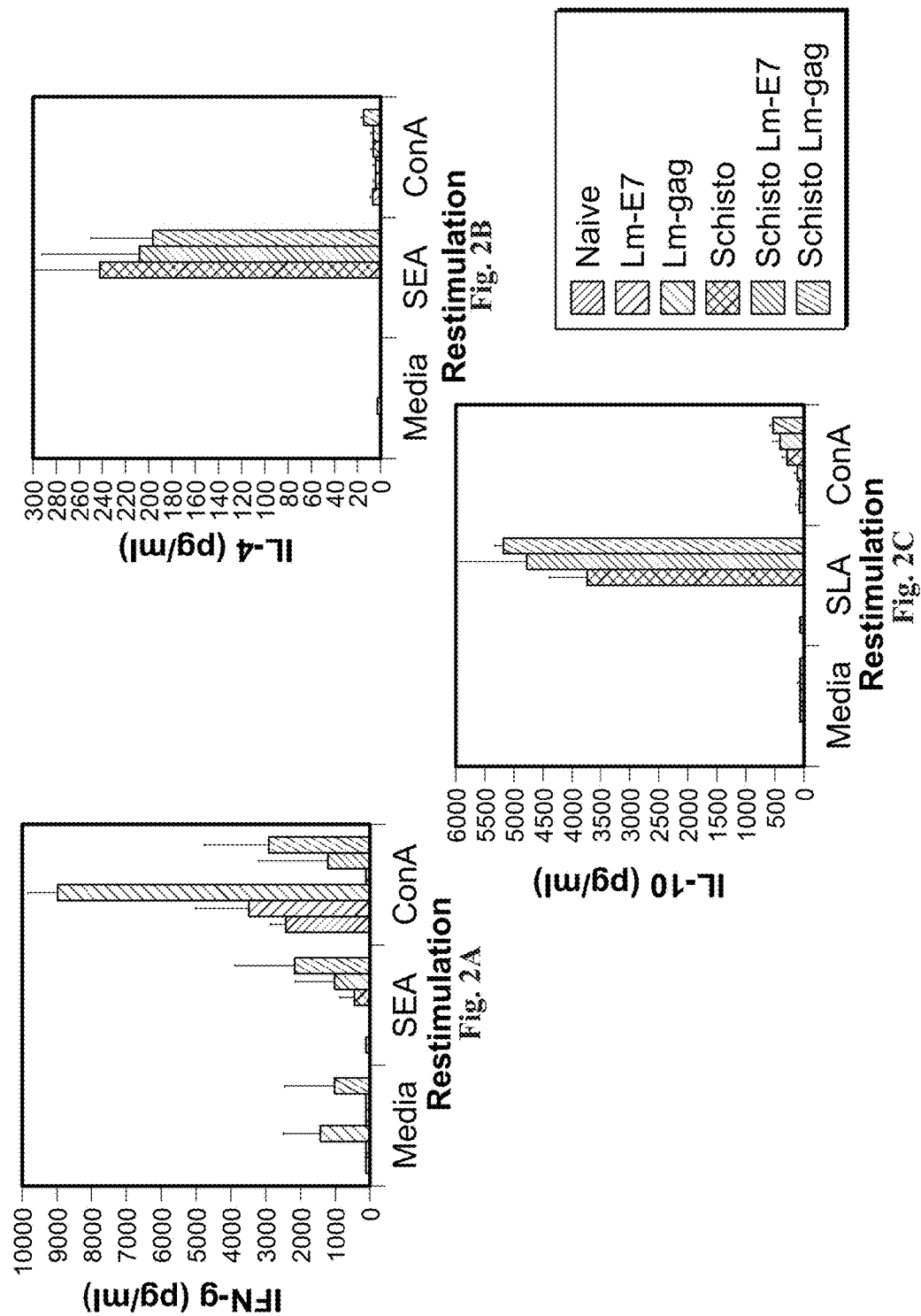
FIGS. 2A-C show verification of host Th2-biasing in Schistosome-infected and vaccinated mice. Helminth-infected, *Listeria* HIV-1-vaccinated mice are Th2 biased and immune suppressed, as indicated by a reduction in IFN-gamma production and increases in levels of IL-4 and IL-10. Ten to twelve weeks post-infection, mice were vaccinated. At 2 wplv, splenocytes were harvested and plated at 1.5 million cells per well in 48-well plates in the presence of media, SEA or concanavalin A (as a positive control). After incubation for 72 hours, supernatants were harvested and analyzed for levels of IFN-g (FIG. 2A), IL-4 (FIG. 2B) and IL-10 (FIG. 2C) by ELISA (BD). Pooled data from two replicate experiments are shown.

A chronic *Schistosoma mansoni* infection is established in mice as a model of chronic helminth infection prior to vaccination with the *Listeria*-vector vaccines (FIG. 1). A hallmark of chronic helminth infection is Th2 biasing of the immune system, which is observed in the chronic schistosomiasis model used throughout this study (FIG. 2). Helminth-infected, *Listeria* HIV-1-vaccinated mice are Th2 biased and immune suppressed, as indicated by a reduction in IFN-γ production and increases in levels of IL-4 and IL-10 when comparing groups with and without helminth infection.

Example 2

Figure 3:
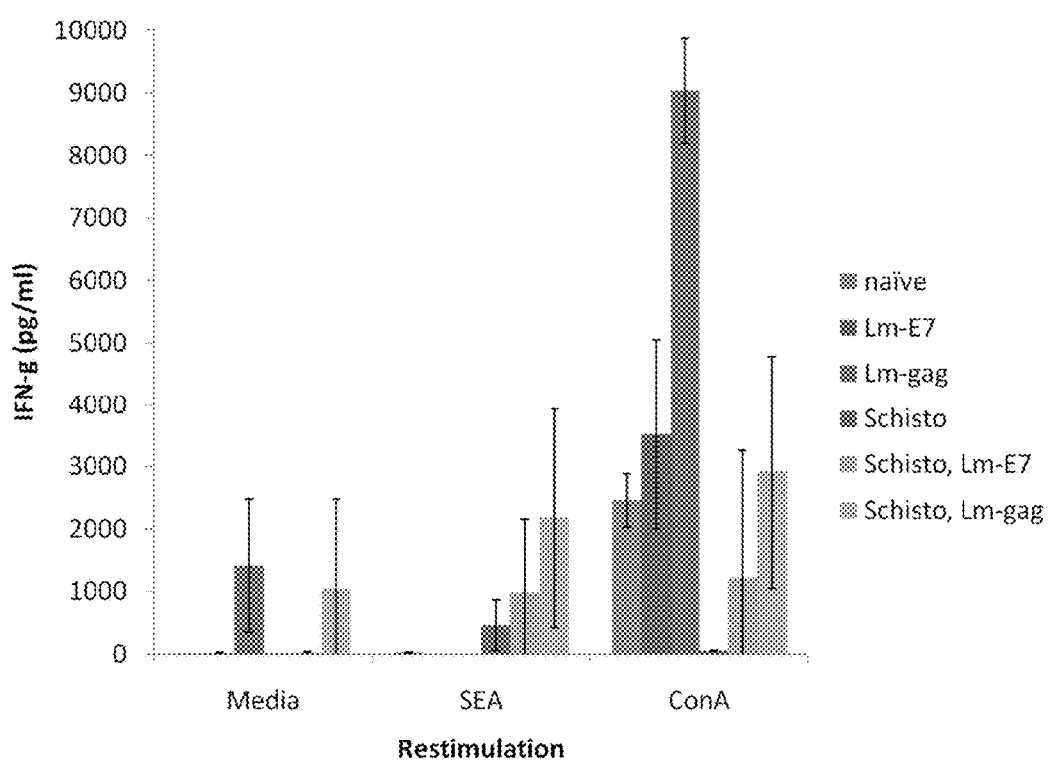
FIG. 3 shows IFN-γ production is reduced in *S. mansoni* infected mice.
Figure 4:
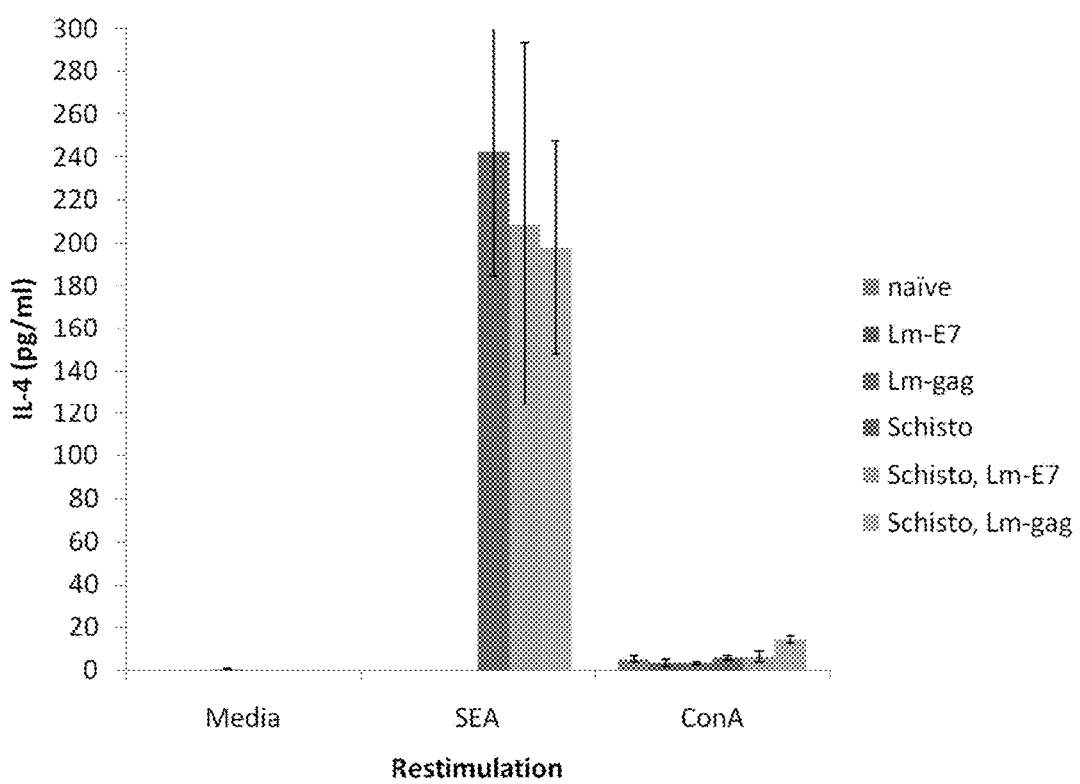
FIG. 4 shows IL-4 levels are increased in mice with chronic schistosomiasis.
Figure 5:
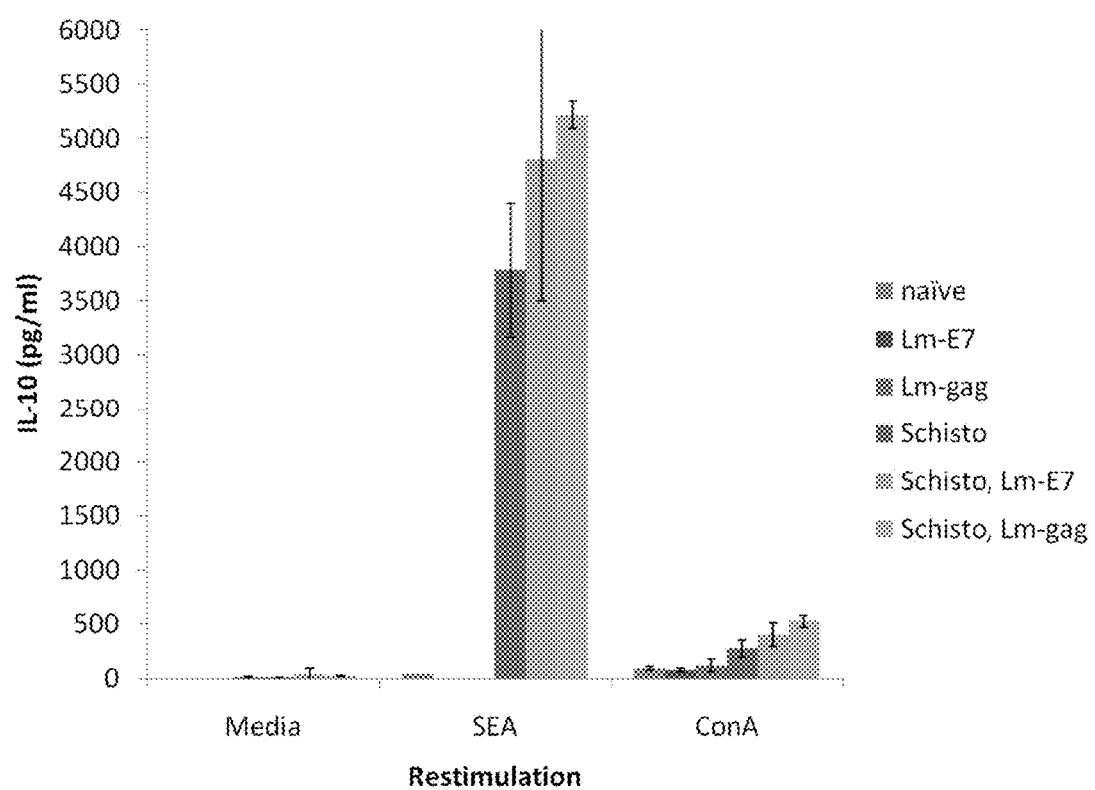
FIG. 5 shows IL-10 production is increased in mice infected with *S. mansoni*.
Figure 6:
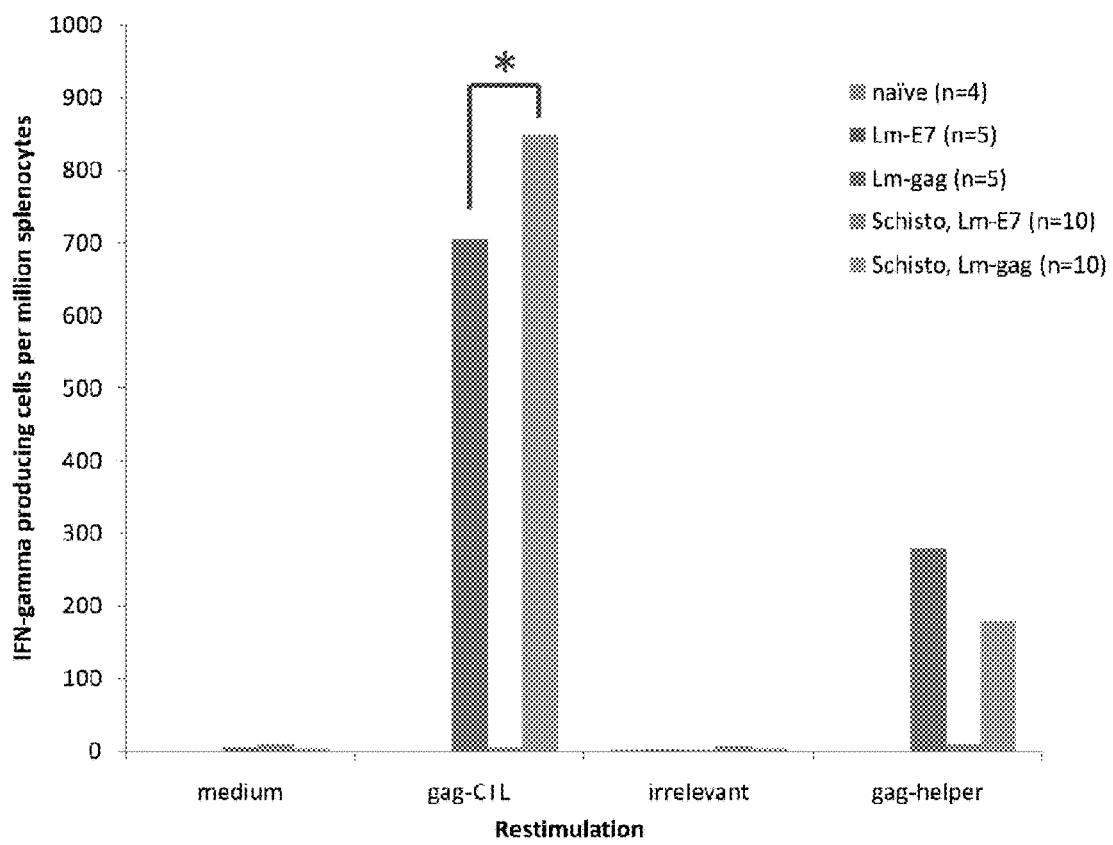
FIG. 6 shows Schistosome infection does not alter the antigen-specific vaccine responses toward immunodominant CTL and helper epitopes.

*Listeria* Vectors are Capable of Driving a Th1 T-Cell Immune Response Despite Helminth Infection-Mediated Suppression of Th1 T-Cell Immune Responses Despite systemic biasing toward Th2, as evidenced by a reduced IFN-γ response (FIG. 3) and an increase in IL-4 and IL-10 production (FIGS. 4 and 5, respectively), antigen-specific production of IFN-γ remains unchanged (FIG. 6), indicating this vaccine can produce a functional cell-mediated immune response in the presence of a Th2 environment. This observation suggests that *Listeria* vector vaccines are capable of driving vaccine-specific immune responses in helminth-infected populations. Further, *Listeria* vectors should be considered in the development of new generation HIV-1, malaria or TB vaccines to be administered to populations in sub-Saharan Africa where helminth infection is highly prevalent.

Example 3

Administration of a *Listeria* Vector-HIV-1 Gag Vaccine to *S. mansoni*-Infected Mice Drives Significant Immune Responses to HIV-1 Gag CTL and T Helper Epitopes Both a single i.p. vaccination with 0.2 LD50 of Lm-gag or a prime-boost vaccination protocol with 0.1 LD50 of Lm-gag elicits significant immune responses to HIV-1 gag CTL and T helper epitopes similar to the immune responses in non-*S. mansoni*-infected mice vaccinated with a prime-boost vaccination protocol with 0.1 LD50 of Lm-gag (FIG. 7).

In addition, oral administration of 100 LD50 but not 10 LD50 of Lm-gag in a prime-boost protocol elicited immune responses to gag-helper (but not gag-CTL) similar to the response elicited in i.p. Lm-gag-vaccinated mice and in oral Lm-gag-vaccinated mice that were not infected with *S. mansoni* (FIG. 8).

Figure 8:
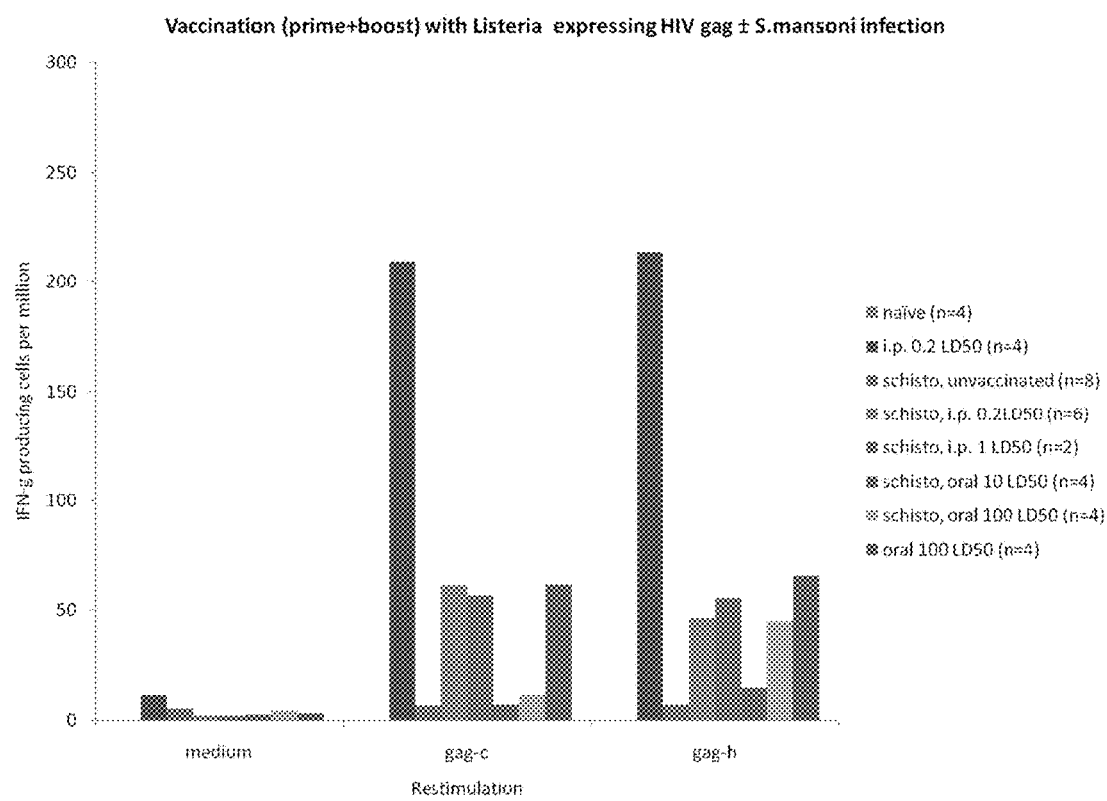
FIG. 8 demonstrates that oral as well as i.p. administration of a *Listeria* vector-HIV-1 gag vaccine to mice chronically infected with the helminth parasite *Schistosoma mansoni*, drives significant immune responses to HIV-1 gag CTL and T helper epitopes in a prime boost protocol.
Figure 9:
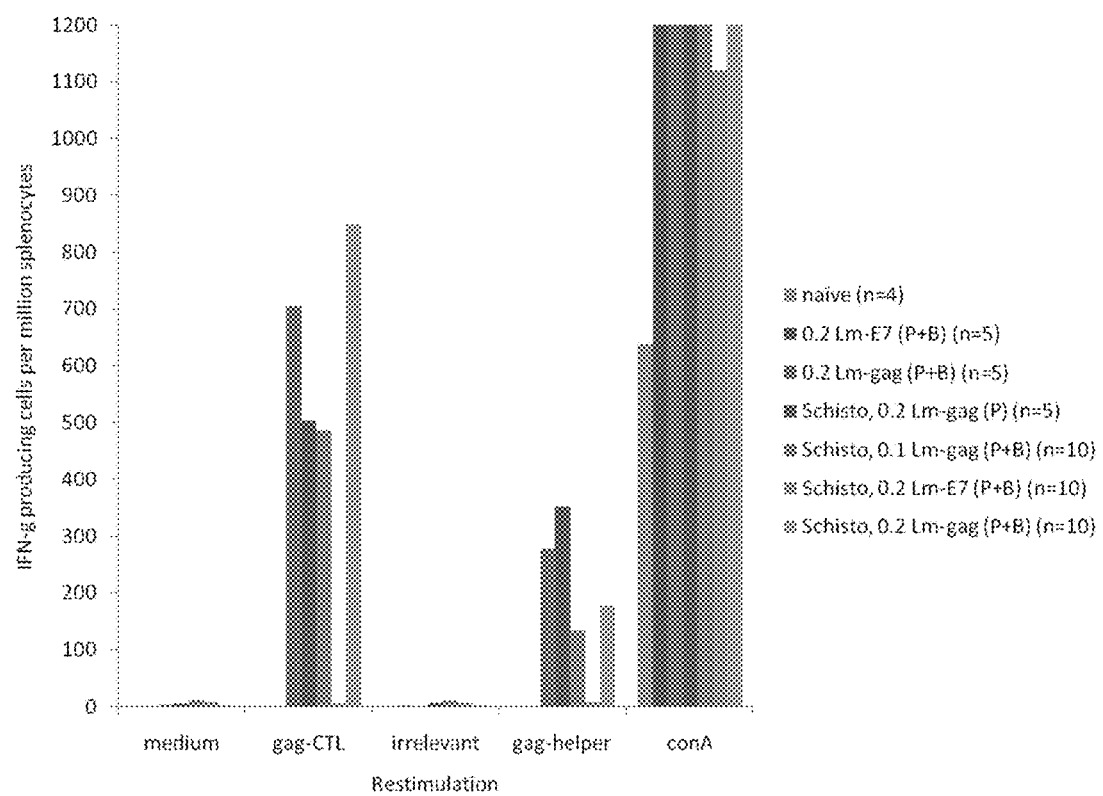
FIG. 9 presents data showing that the administration of a *Listeria* vector-HIV-1 gag vaccine to mice chronically infected with the helminth parasite *Schistosoma mansoni*, drives significant and specific immune responses to HIV-1 gag CTL and T helper epitopes but not to an irrelevant antigen. All groups showed significant immune response to conA, which served as a positive control.
Figure 10:
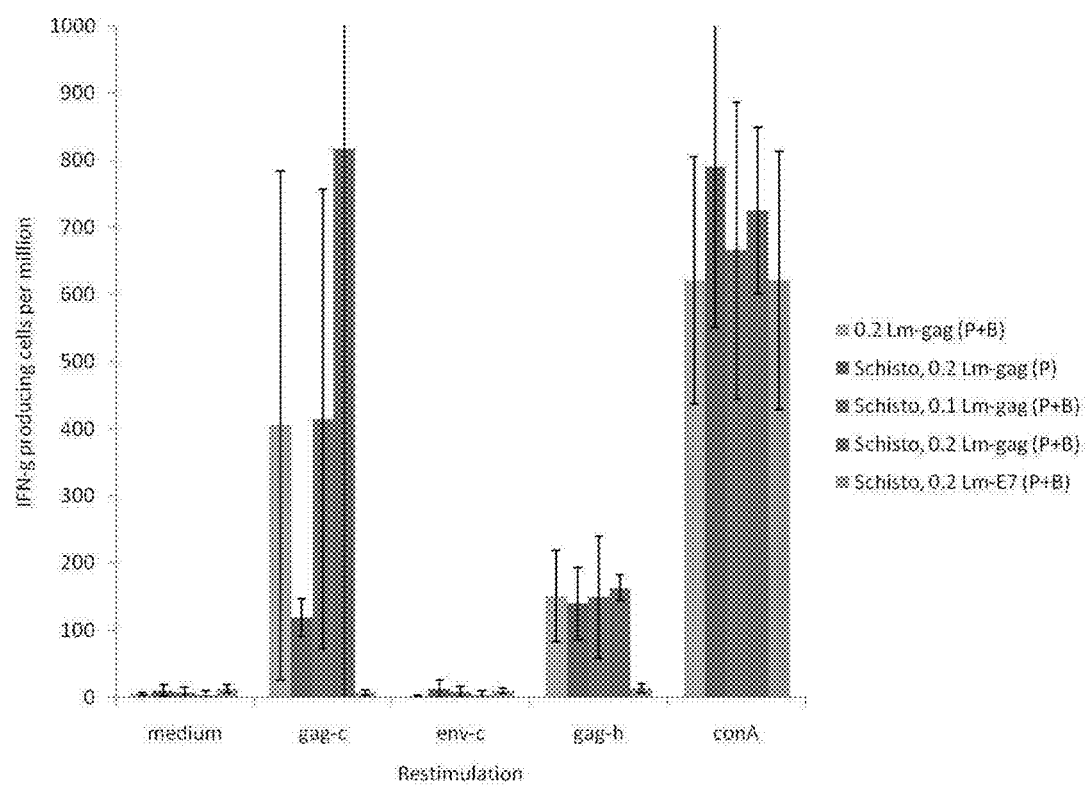
FIG. 10 presents data showing that the administration of a *Listeria* vector-HIV-1 gag vaccine to mice chronically infected with the helminth parasite *Schistosoma mansoni*, drives significant and specific immune responses to HIV-1 gag CTL and T helper epitopes but not to medium (negative control) nor to an env-c peptide. All groups showed significant immune response to conA, which served as a positive control.

All groups demonstrated strong immune responses to conA (positive control) and no groups demonstrated immune response to medium or an irrelevant antigen (FIG. 8). In addition, mice vaccinated in a prime-boost protocol with Lm-E7 (comprising a Human Papilloma Virus E7 antigen instead of HIV-gag) did not demonstrate an immune response upon re-stimulation with gag-CTL or gag-helper, as expected (FIG. 9).

Therefore, administration of a *Listeria* vector-HIV-1 gag vaccine to mice chronically infected with the helminth parasite *Schistosoma mansoni*, drives significant immune responses to HIV-1 gag CTL and T helper epitopes as is further demonstrated below. This observation suggests that *Listeria* vector vaccines are capable of driving vaccine-specific immune responses in helminth-infected populations. This opens up the possibility of using *Listeria* vectors to develop new generation HIV-1, malaria or TB vaccines to be administered to populations in sub-Saharan Africa where helminth infection is highly prevalent.

TABLE 1

Statistical analysis. P-values of the vaccination strategies in the Schisto-infected mouse.

|  | gag-CTL | gag-helper |
| --- | --- | --- |
| 0.2 Lm-gag (P) | 0.54 | 0.63 |
| 0.1 Lm-gag (P + B) | 0.48 | 0.12 |
| 0.2 Lm-gag (P + B) | 0.75 | 0.32 |

Example 4

*Listeria*-Vector HIV Vaccines Function in the Context of Helminth Infection

Figure 11A:
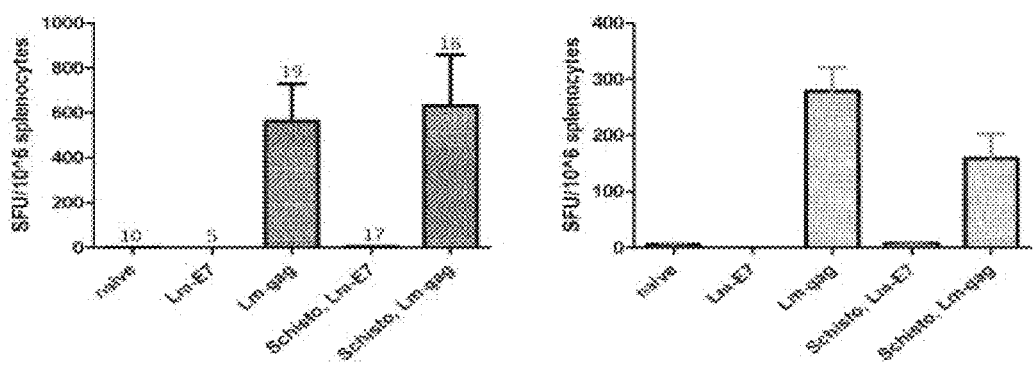
FIGS. 11A-B show a *Listeria* vector HIV-1 vaccine that induces antigen-specific vaccine responses toward immunodominant CTL and helper epitopes during chronic helminth infection. Two wplv, splenocytes were harvested and plated at 300K and 150K cells per well in IFN-γ ELISpot plates in the presence of media, specific CTL peptide, irrelevant peptide, specific helper peptide or con A (as a positive control). After incubation for 20 hours, ELISpots (BD) were performed, counted using an Immunospot analyzer (C.T.L.), and graphed as number of spots per million splenocytes for CTL (blue) or helper (red) immunodominant epitopes. Splenocytes were unresponsive to media and the irrelevant peptide, NP for all groups, however, responded to the positive control conA (data not shown). Data is inclusive of three independent experiments. Mean±SEM (FIG. 11A) or individual data points (FIG. 11B) were plotted. Total numbers of animals per group are shown above the bars (top left). No significant difference ($p<0.05$) was observed when comparing Lm-gag±Schistosomiasis using t-test analysis.
Figure 11B:
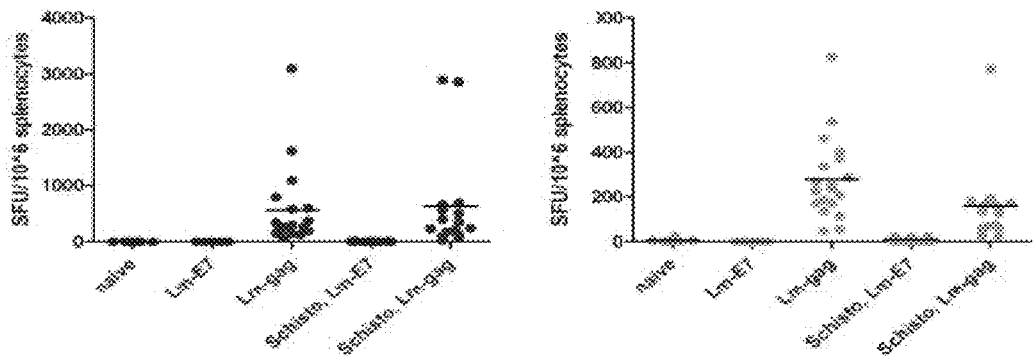

As shown in FIG. 11, *Listeria* vector HIV-1 vaccine induces antigen-specific vaccine responses toward immunodominant CTL (FIG. 11A) and helper (FIG. 11B) epitopes during chronic helminth infection. Splenocytes were unresponsive to media and the irrelevant peptide (NP) for all groups, however, all mice responded to the positive control conA. Data is inclusive of three independent experiments and the total numbers of animals per group (5-19) are shown (FIG. 11, top left). When comparing the 2 responsive groups (Lm-gag±Schistosomiasis), no significant difference was observed.

Figure 12A:
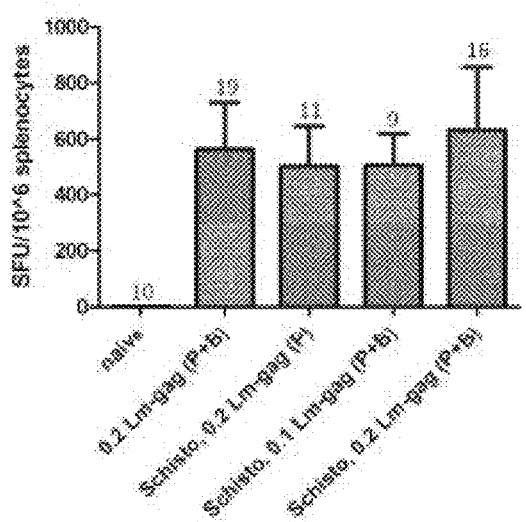
FIGS. 12A-B show varying the vaccine dose and regimen does not alter the vaccine response to the immunodominant epitope. Experimental details are similar to FIGS. 1 and 3, with differences described herein. For vaccination of animals with chronic Schistosomiasis, the vaccine dose was lowered to 0.1 $LD_{50}$ (noted as 0.1) or the schedule was altered to eliminate the boost, resulting in a prime-only vaccine strategy (noted as P, for prime only). Reponses against the CTL (FIG. 12A) or helper (FIG. 12B) epitopes are graphed as mean±SEM. Total numbers of animals per group are shown above the bars on the CTL graph. Among responses to the CTL epitope (FIG. 12A), no significant differences between responsive groups were observed. *$p<0.05$, **$p<0.01$ when comparing responding groups using t-test analysis.
Figure 12B:
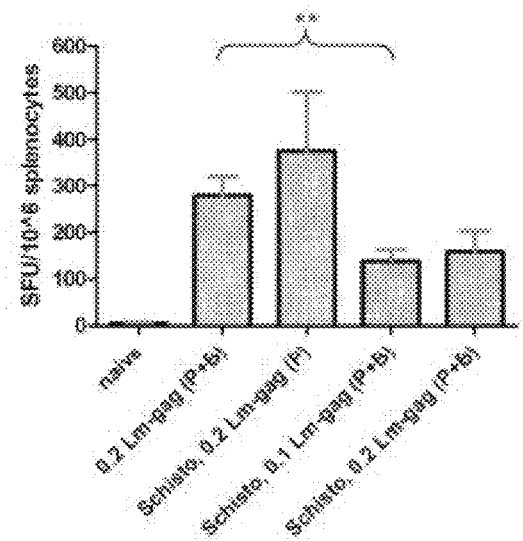

Varying the vaccine dose and regimen does not alter the vaccine response to the immunodominant epitope (FIG. 12). For vaccination of animals with chronic Schistosomiasis, the vaccine dose was lowered to 0.1 $LD_{50}$ (noted as 0.1) or the schedule was altered to eliminate the boost, resulting in a prime-only vaccine strategy (noted as P, for prime only). No significant differences were observed when comparing the response to the CTL epitope among the responsive (non-control) groups.

Example 5

Responses of Effector Cells, Part of the Cell-Mediated Immune Response, are Durable and Unaltered by Pre-Existing Chronic Helminth Infection Several months after the last vaccination, responses to the immunodominant epitope by the effector CTL cells (FIG. 13A), does not differ between in response to chronic helminth infection. Mice were sacrificed at various times post last vaccination and responses of uninfected or schistosome-infected mice to immunodominant CTL (FIG. 13A) and helper (FIG. 13B) epitopes were analyzed. Within the effector cell responses to the immunodominant CTL epitope (FIG. 13A), no significant differences were found when comparing each time point±Schistosomiasis, indicating the effector cell response to the vaccine is unchanged over time between the groups. For Th1 responses to the helper epitope (FIG. 13B), there are differences when comparing±Schistosomiasis at each time point, but these differences are not relevant to a functional vaccine memory response.

Example 6

Figure 14A:
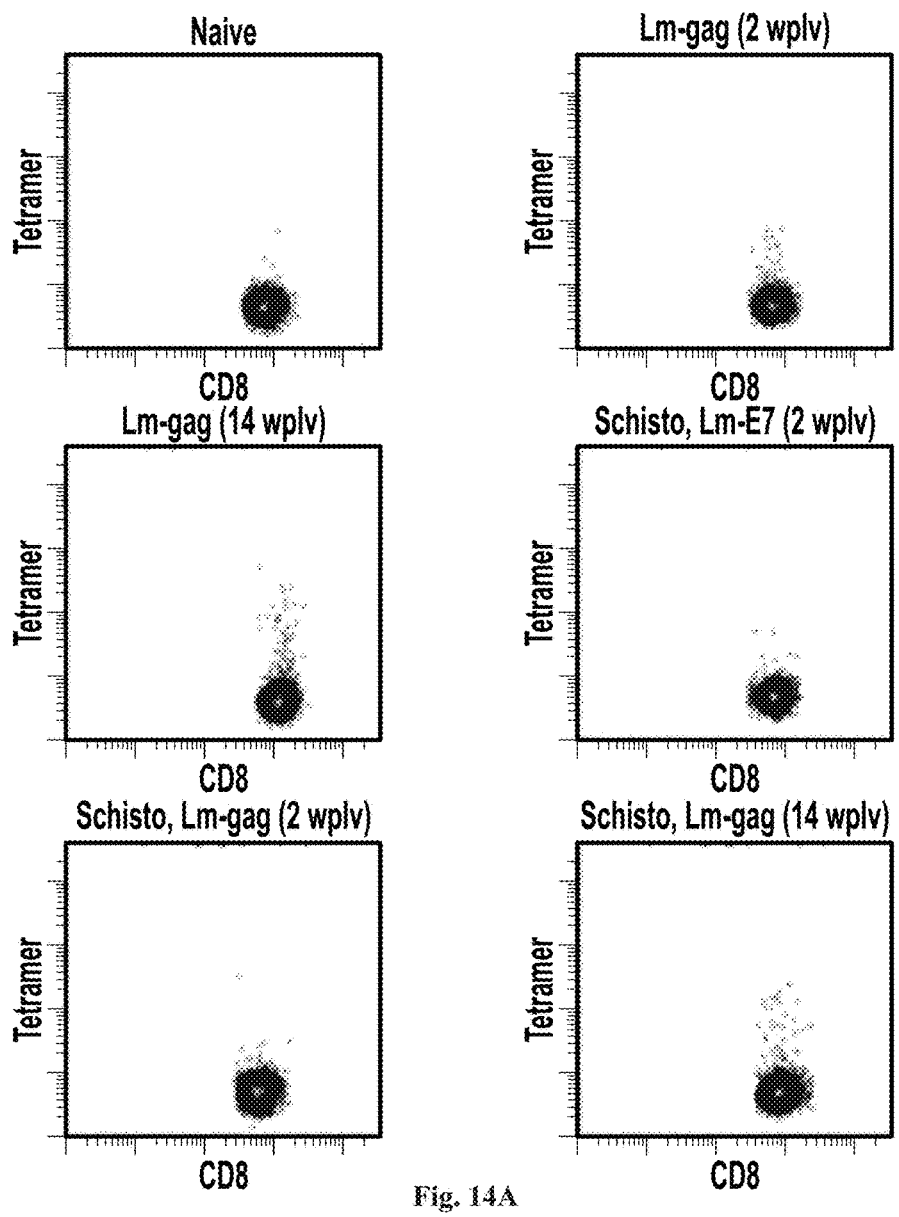
FIGS. 14A-B. Antigen-specific CD8+ T cells are generated in the presence of Schistosome infection and persist for several months at levels comparable to uninfected. To verify the IFN-gamma responses seen in the ELISpot results arise from antigen-specific CD8+ T cells, splenocytes, at 2 (circles) and 14 (squares) wplv, were analyzed by flow cytometry for molecular specificity to vaccine epitopes. Splenocytes were stained with CD8 and gag-tetramer and live cells were acquired and analyzed for tetramer positive staining within the CD8+ population. Representative data is shown (FIG. 14A) and individual data points are plotted (FIG. 14B). No significant differences ($p<0.05$) were found when comparing between groups within a given time point, however, $p<0.01$ and *$p<0.001$, when comparing within vaccination groups using t-test analysis.
Figure 14B:
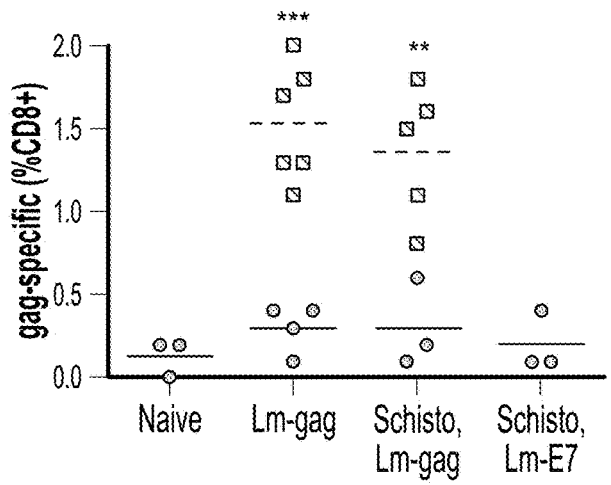

Antigen-Specific CD8+ T Cells are Generated in the Presence of Schistosome Infection and Persist for Several Months at Levels Comparable to Uninfected To verify the IFN-gamma responses seen in the ELISpot results arise from antigen-specific CD8+ T cells, splenocytes were analyzed by flow cytometry for molecular specificity of the TCR to vaccine epitopes presented by the MHC molecule. Briefly, splenocytes were stained with an anti-CD8 antibody and gag-tetramer and live cells were acquired and analyzed for tetramer positive staining within the CD8+ population (FIG. 14). No significant differences were found when comparing between groups within a given time point, however, differences were observed within the same group when comparing the two different time points.

Example 7

Listeria HIV-1 Vaccine Induces Immunological Memory

Figure 15:
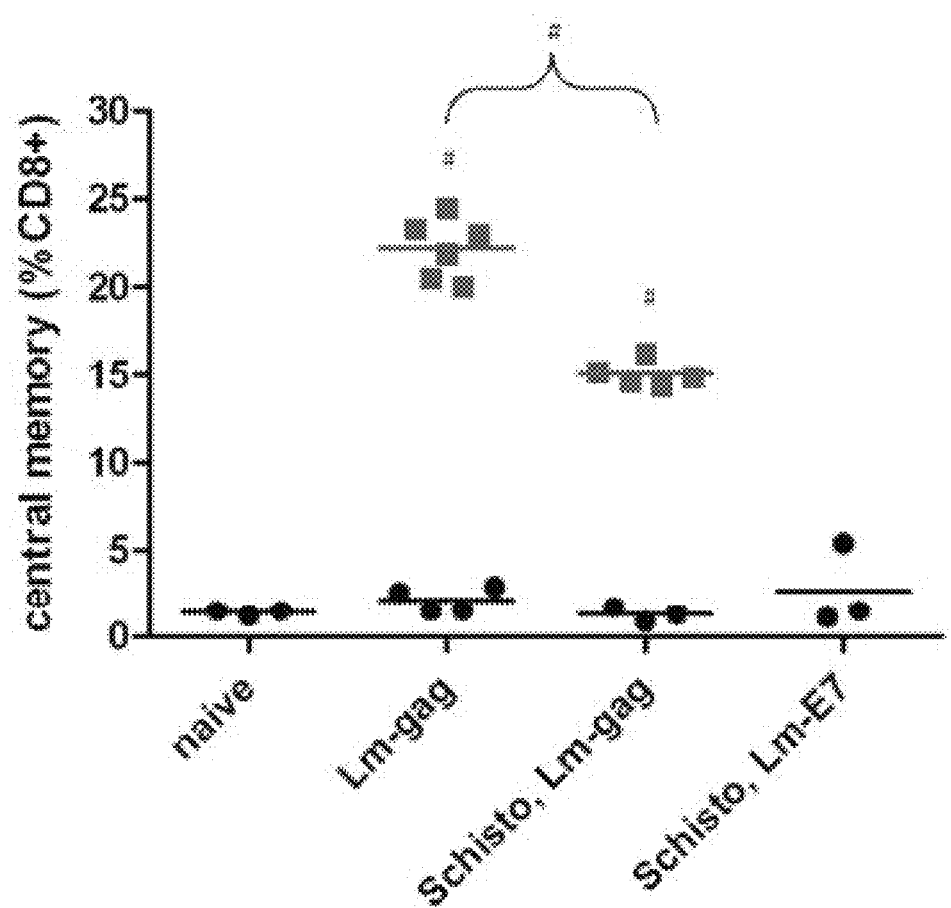
FIG. 15 shows that HIV-1 vaccine induces immunological memory. Central memory T cells are increased several months post vaccination, at which time there is a difference in the schistosome-infected group. At 2 (circles) and 14 (squares) wplv, splenocytes are analyzed by flow cytometry for immunological memory. Splenocytes were stained with CD62L, CD197, CD8 and gag-tetramer. Live cells were acquired and analyzed for central memory (CD62L+ CD197+), effector memory (CD62L−CD197−), and molecular specificity (CD8+tetramer+). Since CD44 wasn't used, the effector memory compartment also contains effectors cells and therefore, isn't plotted with these results. However, all tetramer+ cells at 14 wplv were central memory (data not shown). Individual data points are plotted. #$p<0.0001$, when comparing between or within groups using t-test analysis.

Splenocytes were analyzed by flow cytometry for immunological memory (FIG. 15). Briefly, splenocytes were stained with gag-tetramer and anti-CD8, anti-CD62L and anti-CD197 antibodies. Live cells were acquired and analyzed for central memory (CD62L+CD197+), effector memory (CD62L-CD197-), and molecular specificity (CD8+tetramer+). Since CD44 wasn't used as a marker, the effector memory compartment also contains effectors cells and therefore, isn't plotted with these results. However, all tetramer+ cells at 14 wplv were central memory. Central memory T cells are increased several months post vaccination, at which time there is a difference in the schistosome-infected group.

Example 8

Listeria HIV-1 Vaccine Induces Functional Effector Cells in a Th2 Environment

Figure 16A:
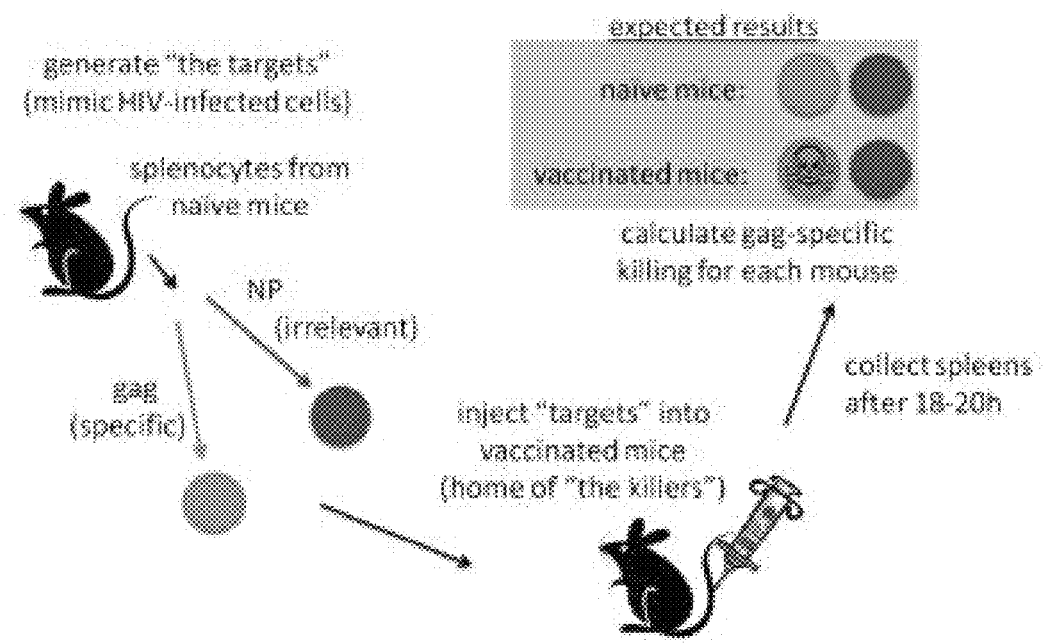
FIGS. 16A-B show that HIV-1 vaccine induces functional effector cells in a Th2 environment. To assay for effector cell function, an in vivo CTL assay was performed. Briefly, one million target cells (pulsed with specific or irrelevant peptide, stained green or violet, respectively) were injected intravenously into vaccinated animals. After overnight in vivo killing, splenocytes were collected and analyzed by flow cytometry for target recovery.
Figure 16B:
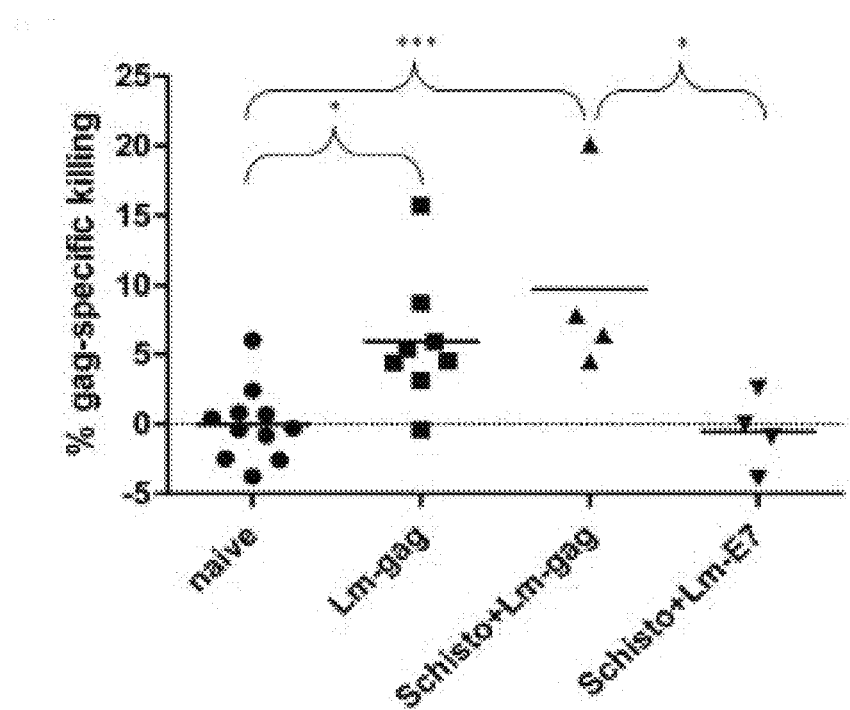

To assay for effector cell function, an in vivo CTL assay was performed. Briefly, one million target cells (pulsed with specific or irrelevant peptide, stained green or violet, respectively) were injected intravenously into vaccinated animals (FIG. 16A). After overnight in vivo killing, splenocytes were collected, analyzed by flow cytometry for target recovery and gag-specific killing was calculated (FIG. 16B). No significant difference was observed between Lm-gag vaccinated groups with and without chronic Schistosomiasis, indicating the vaccine response is as effective in helminth-infected mice as the uninfected mice.

Example 9

Established Listeria HIV-1 Vaccine Responses are Altered by Subsequent Schistosome Infection Having shown that immune responses are unaltered by pre-existing helminth infection, it was important to determine if vaccine responses would be altered if the helminth infection occurred after vaccination. To address this, the timeline of the experiment was altered to vaccinate prior to chronic helminth infection (FIG. 17A). Mice were sacrificed at various times post schistosome infection and responses to immunodominant CTL (FIG. 17B) and helper (FIG. 17C) epitopes were analyzed. Although responses to helper peptides remain unchanged, vaccination prior to schistosome infection causes CTL responses to diminish as the immune system shifts to a Th2 bias. However, vaccine responses by the schistosome-infected mice are restored after a second boost and/or praziquantel treatment of the helminth infection. Further, the Listeria vector vaccine generates a memory response.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. A method of treating an infectious disease in a subject having a Th2 phenotypic profile, the method comprising the step of administering to said subject a therapeutically effective dose of a *Listeria* vaccine vector, wherein said *Listeria* vaccine vector expresses and secretes an antigen fused to an additional immunogenic polypeptide or a signal sequence thereof, wherein said antigen is an infectious disease antigen, wherein said Th2 phenotypic profile is parasite-induced, and wherein said administering produces a Th1 cell-mediated immune response in said subject.

2. The method of claim 1, wherein said parasite is a helminth, or a protozoan parasite.

3. The method of claim 2, wherein said helminth is *Schistosoma mansoni*.

4. The method of claim 2, wherein said protozoan parasite is malaria, *leishmania*, toxoplasma.

5. The method of claim 1, wherein said additional polypeptide is a non-hemolytic Listeriolysin O (LLO) polypeptide, an ActA polypeptide, or a PEST sequence.

6. The method of claim 1, wherein said subject is human.

7. The method of claim 1, wherein said antigen is an HIV antigen, a malaria antigen, or a tuberculosis antigen.

8. The method of claim 7, wherein said antigen elicits an immune response to HIV-1 gag cytotoxic T lymphocyte or to HIV-1 gag T helper epitopes.

9. The method of claim 7, wherein said HIV antigen is HIV-gag, pol, env, protease, rev, tat, nef, vif, or vpr.

10. The method of claim 7, wherein said malaria antigen is circumsprozoite protein (CSP), sporozoite surface protein 2 (PfSSP), liver stage antigen 1 (LSA1), merozoite surface protein 1 (MSP-1), serine repeat antigen and AMA-1, Pfs25, schizont export protein, 19 repeats of the sprozoite surface protein (NANP), SPf66, recombinant (Asn-Ala-Pro15Asn-Val-Asp-Pro)2-Leu-Arg(R32LR) protein covalently bound to a purified *Pseudomonas aeruginosa* toxin, NYVAC-Pf7, (NANP)19-5.1, (RTS,S, RTS,S/AS01), or a combination thereof.

11. The method of claim 7, wherein said tuberculosis antigen is ESAT-6, TB10.4, CFP10, RD1-ORF5, RD1-ORF2, Rv1036, MPB64, MPT64, Ag85A, Ag85B (MPT59), Mtb39, MPB59, Ag85C, 19 kDa lipoprotein, MPT32 and alpha-crystallin, EsxG, Rv2430c, Rv2041c, or at least on T-cell epitope of any of the above.

12. The method of claim 1, further comprising the step of administering a booster vaccination.

13. The method of claim 12, wherein said booster vaccination comprises a DNA vaccine encoding said antigen fused to an additional immunogenic polypeptide or a signal sequence thereof, a recombinant polypeptide comprising said antigen fused to an additional immunogenic polypeptide or a signal sequence thereof, a viral vector encoding said antigen fused to an additional immunogenic polypeptide or a signal sequence thereof or a live recombinant *Listeria* vaccine vector.

14. The method of claim 1, wherein said Th1 immune response is a cytotoxic T-cell response or a memory T-cell response.

15. The method of claim 1, wherein said *Listeria* vaccine vector is a recombinant auxotrophic dal/dat mutant *Listeria* strain.

16. The method of claim 1, wherein said *Listeria* vaccine vector comprises an actA gene mutation.

17. The method of claim 1, wherein said *Listeria* vaccine vector comprises an inlB gene mutation.

18. The method of claim 1, wherein said *Listeria* vaccine vector comprises an actA and inlB gene mutation.

19. The method of claim 1, wherein said immune response is against an infectious disease in said subject.

20. The method of claim 1, wherein said infectious disease is amebiasis, an HIV infection, a malaria infection, a *leishmania* infection, a *trichuris* infection, or a tuberculosis infection.

21. The method of claim 1, wherein said subject having a Th2 phenotypic profile is Th1 unresponsive.

22. The method of claim 21, wherein Th1 response indicators in said subject are reduced or absent.

23. The method of claim 1, wherein said subject having a Th2 phenotypic profile is Th2 biased and immune suppressed prior to treatment with said *Listeria* vaccine vector.

24. The method of claim 23, wherein said subject having a Th2 phenotypic profile has a reduction in IFN-gamma production, an elevation in the level of IL-4, or an elevation in the level of IL-10, prior to treatment with said *Listeria* vaccine vector.

* * * * *